US011248004B2

(12) United States Patent
Lee et al.

(10) Patent No.: US 11,248,004 B2
(45) Date of Patent: Feb. 15, 2022

(54) SUBSTITUTED ISOQUINOLINES AS ROCK KINASE INHIBITORS

(71) Applicant: Cervello Therapeutics LLC, Malvern, PA (US)

(72) Inventors: Matthew Randolph Lee, Del Mar, CA (US); Anthony Joseph Varano, Jr., Berwyn, PA (US); Thomas P. Bobinski, San Diego, CA (US)

(73) Assignee: Cervello Therapeutics, LLC., Malvern, PA (US)

( * ) Notice: Subject to any disclaimer, the term of this patent is extended or adjusted under 35 U.S.C. 154(b) by 0 days.

(21) Appl. No.: 16/867,162

(22) Filed: May 5, 2020

(65) Prior Publication Data

US 2020/0262844 A1    Aug. 20, 2020

Related U.S. Application Data

(63) Continuation-in-part of application No. 16/676,044, filed on Nov. 6, 2019, now Pat. No. 10,745,381.

(60) Provisional application No. 62/756,202, filed on Nov. 6, 2018.

(51) Int. Cl.
| | | |
|---|---|---|
| *A61K 31/4725* | (2006.01) | |
| *C07D 217/22* | (2006.01) | |
| *C07D 498/08* | (2006.01) | |
| *C07D 401/12* | (2006.01) | |
| *C07D 405/14* | (2006.01) | |
| *C07D 471/04* | (2006.01) | |
| *C07D 403/12* | (2006.01) | |

(52) U.S. Cl.
CPC ......... *C07D 498/08* (2013.01); *C07D 401/12* (2013.01); *C07D 403/12* (2013.01); *C07D 405/14* (2013.01); *C07D 471/04* (2013.01)

(58) Field of Classification Search
CPC .......................... A61K 31/4725; C07D 217/22
USPC ........................................... 514/309; 546/141
See application file for complete search history.

(56) References Cited

U.S. PATENT DOCUMENTS

| | | |
|---|---|---|
| 8,648,069 B2 | 2/2014 | Akritopoulou-Zanze et al. |
| 10,106,525 B2 | 10/2018 | Rosen et al. |
| 2003/0171341 A1 | 9/2003 | Sun et al. |
| 2004/0266755 A1 | 12/2004 | Islam et al. |
| 2009/0306053 A1 | 12/2009 | Hidaka et al. |
| 2017/0037050 A1 | 2/2017 | Wu et al. |
| 2017/0137385 A1 | 5/2017 | Chimenti et al. |
| 2017/0246181 A1 | 8/2017 | Rosen et al. |
| 2019/0308953 A1 | 10/2019 | Poyurovsky et al. |

FOREIGN PATENT DOCUMENTS

| | | |
|---|---|---|
| WO | 2018009622 A1 | 1/2018 |
| WO | 2018009625 A1 | 1/2018 |
| WO | 2018009627 A1 | 1/2018 |
| WO | 2019014300 A1 | 1/2019 |
| WO | 2019014303 A1 | 1/2019 |
| WO | 2019014304 A1 | 1/2019 |
| WO | 2019014308 A1 | 1/2019 |

OTHER PUBLICATIONS

Defert et al., "Rho kinase inhibitors: a patent review (2014-2016)", Expert Opinion on Therapeutic Patents, 2017, vol. 27, No. 4, 507-515.
Green et al., "Design, Synthesis, and Structure—Activity Relationships of Pyridine-Based Rho Kinase (ROCK) Inhibitors", J. Med. Chem. 58:5028-5037 (2015).
Bandarage et al., "ROCK inhibitors 3: Design, synthesis and structure-activity relationships of 7-azaindole-based Rho kinase (ROCK) inhibitors", Bioorganic & Medicinal Chemistry Letters 28 (2018) 2622-2626.
International Search Report and Written Opinion for PCT Application No. PCT/US19/59992 dated Mar. 2, 2020.
International Search Report and Written Opinion for corresponding PCT Application No. PCT/US20/31428 dated Jul. 30, 2020.

*Primary Examiner* — Douglas M Willis
(74) *Attorney, Agent, or Firm* — Wood, Phillips, Katz, Clark & Mortimer

(57) ABSTRACT

The present invention relates to indoline-based compounds that inhibit Rho-associated protein kinase (ROCK) activity. In particular, the present invention relates to compounds, pharmaceutical compositions and methods of use, such as methods of inhibiting ROCK activity and methods for treating, for example cerebral cavernous malformation syndrome (CCM) and cardiovascular diseases using the compounds and pharmaceutical compositions of the present invention.

17 Claims, No Drawings

SUBSTITUTED ISOQUINOLINES AS ROCK KINASE INHIBITORS

FIELD OF THE INVENTION

The present invention relates to compounds that are Rho-associated protein kinases (ROCK) inhibitors. In particular, the present invention relates to compounds that selectively inhibit the activity of ROCK, pharmaceutical compositions comprising the compounds and methods of use therefor.

BACKGROUND OF THE INVENTION

ROCK is a critical RhoA effector involved in regulation of multiple cellular signaling pathways through phosphorylation of multiple substrates, including myosin light chain (MLC), LIM Kinase, MYPT1, and CPI-17. ROCK substrates are involved in smooth muscle contractility, vascular permeability, actin filament organization, cell adhesion, cell migration, growth control and cytokinesis. The direct involvement of ROCK in smooth muscle contractility results from increased phosphorylation of both MLC, which increases contractility upon phosphorylation, and MLC-phosphatase, which is inhibited upon phosphorylation, thereby further increaser MLC phosphorylation ROCK activation, thus, results in increased smooth muscle contractility.

Literature reports suggest a link between ROCK activity and numerous cardiovascular diseases associated with vasotonic dysfunction, including hypertension, atherosclerosis, ischemic stroke, coronary vasospasm, cerebral vasospasm, angina, erectile dysfunction, and renal disease and also a link with other smooth muscle hyper-reactivity, such as glaucoma and asthma.

Cerebral cavernous malformation (CCM) syndrome is a disease associated with defective endothelial junctions predominantly in the brain predisposing patients to a lifetime risk of seizures, hemorrhagic stroke, and other neurological deficits. Cerebral cavernous malformations (CCMs) are vascular malformations mostly found within the central nervous system, e.g., brain stem and spinal cord, that can occur in sporadic or autosomal dominant inherited forms, the latter of which map to three loci, KRIT-1/CCM1, MGC4607/OSM/CCM2, and PDCD10/CCM3 (e.g., see Glading et al., (2007) J. Cell Biol. 179:247-254).

CCM1, CCM2 and CCM3 proteins each interact with a number of proteins, including Rap1, a RhoA-GTPase. Rap1 plays a role in regulating the actin cytoskeleton by stimulating the formation of actin fibers. Inactivating mutations in CCM1, CCM2 or CCM3 are sufficient to induce CCM vascular lesions by inhibiting endothelial cell vessel-like tube formation and extracellular matrix invasion leading to weakened junctions between cells and increased leakage from blood vessels. The loss of expression of the CCM1, -2, or -3 proteins causes a marked overexpression and increased activation of Rap1. Increased Rap1 activation is associated with increased Rho kinase-dependent (ROCK) phosphorylation, and short hairpin RNA knockdown of ROCK rescued endothelial cells from CCM pathology (e.g., see Borikova et al., (2010) J. Biol. Chem. 285:11760-11764).

CCM patients unfortunately have limited treatment options and there are no approved drugs in the United States for treating CCM. Fasudil hydrochloride, an isoquinoline sulfonamide derivative, is a potent ROCK inhibitor that has been approved outside the United States for treating cerebral vasospasm after subarachnoid hemorrhage and symptoms of cerebral ischemia. Fasudil has been used off-label by physicians to treat CCM, presumably by inhibiting ROCK kinase activity; however, Fasudil, which shows poor selectivity over other AGC-family kinases, also exhibits a number of serious toxic side effects and drawbacks including mandated short-course treatments, low oral bioavailability, cell toxicity and blood pressure fluctuations (e.g., see Xin et al., (2015) BioSci Rep. 35: 1-13).

There is a serious unmet medical need to treat patients having CCM, and more broadly for numerous other diseases involving elevated smooth muscle contractility, such as cardiovascular disease, with prevailing evidence pointing towards selective ROCK kinase inhibitors as a likely source for pharmacological therapeutic intervention. In conjunction, there is a need to develop new ROCK kinase inhibitors that have improved treatment times, improved oral bioavailability, reduced cell toxicity and reduced off-target activity, particularly over the AGC-family kinase members.

BRIEF SUMMARY OF THE INVENTION

The present inventors recognized a need to develop new ROCK kinase inhibitors that demonstrate improved cellular potency, kinome selectivity, efficacy, stability and safety. The compounds and compositions of the present invention advantageously overcome one or more of these shortcomings by providing potent, selective and orally active ROCK inhibitors.

In one aspect of the invention, compounds are provided that inhibit ROCK kinase activity. In certain embodiments, the compounds are represented by formula (Ia), formula (Ib), formula (IIa) or formula (IIb):

Formula (I)

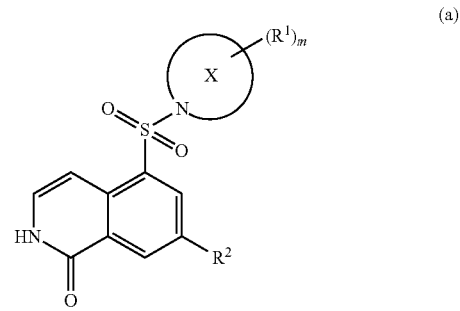

(a)

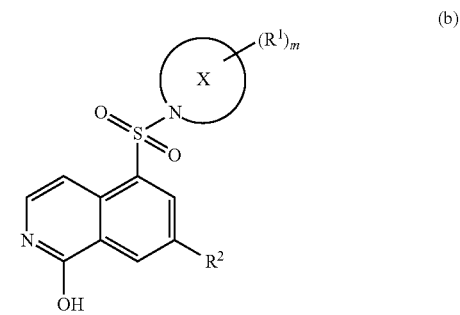

(b)

Formula (II)

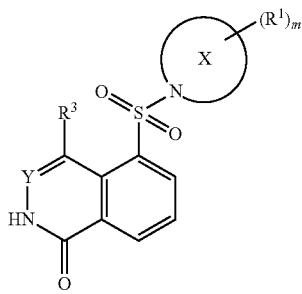

(a)

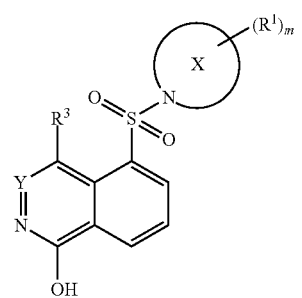

(b)

or a pharmaceutically acceptable salt thereof:
wherein:
X is a partially saturated aza-containing heteroaryl;
Y is N or CH;
each $R^1$ is cyano, hydroxyl, hydroxyalkyl, halogen, haloalkyl, alkoxy, Q-$C_1$-$C_3$ alkyl, —N($R^4$)$_2$, —N$R^4$C(O)C1-C3 alkyl or cycloalkyl;
Q is a bond, O or N;
each $R^2$ is hydrogen or halogen;
each $R^3$ is hydrogen, halogen or $C_1$-$C_3$ alkyl;
each $R^4$ is hydrogen or $C_1$-$C_3$ alkyl; and
m is 0, 1, 2 or 3.

In another aspect of the invention, pharmaceutical compositions are provided comprising a therapeutically effective amount of a compound of formula (Ia), formula (Ib), formula (IIa) or formula (IIb) and pharmaceutically acceptable excipients, salts, solvates, carriers and/or diluents.

In yet another aspect, the present invention is directed to a method of treating a cardiovascular disease associated with increased vasotension comprising administering a therapeutically effective amount of a compound of formula (Ia), formula (Ib), formula (IIa) or formula (IIb) or pharmaceutical composition thereof to a patient in need thereof. In one embodiment, the cardiovascular disease is hypertension, atherosclerosis, ischemic stroke, coronary vasospasm, cerebral vasospasm, angina and erectile dysfunction.

In yet another aspect, the present invention is directed to a method of treating diseases involving elevated non-vascular smooth muscle contractility comprising administering a therapeutically effective amount of a compound of formula (Ia), formula (Ib), formula (IIa) or formula (IIb) or pharmaceutical composition thereof to a patient in need thereof. In one embodiment, the disease involving elevated non-vascular smooth muscle contractility asthma and glaucoma.

In yet another aspect of the invention, methods for inhibiting ROCK activity in a cell comprising contacting the cell with a compound of formula (Ia), formula (Ib), formula (IIa) or formula (IIb) are provided. Also provided are methods for treating CCM in a patient comprising administering a therapeutically effective amount of a compound of formula (Ia), formula (Ib), formula (IIa) or formula (IIb) or pharmaceutical composition thereof to a patient in need thereof.

DETAILED DESCRIPTION OF THE INVENTION

The present invention relates to ROCK kinase inhibitors. In particular, the present invention relates to compounds that selectively inhibit the activity of a ROCK kinase, pharmaceutical compositions comprising a therapeutically effective amount of the compounds, and methods of use therefor, such as methods for treating cerebral cavernous malformation syndrome (CCM) and cardiovascular diseases.

Definitions

Unless defined otherwise, all technical and scientific terms used herein have the same meaning as is commonly understood by one skilled in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. All atoms are understood to have their normal number of valences for bond formation (i.e., 4 for carbon, 3 for N, 2 for O, and 2, 4, or 6 for S, depending on the oxidation state of the S).

As used herein, a "ROCK kinase" refers to a member of the Rho-associated protein kinase ("ROCK") family including ROCK1 and ROCK2 kinases.

As used herein, an "ROCK inhibitor" refers to compounds of the present invention that are represented by formulae (I) or (II) as described herein. These compounds are capable of negatively modulating or inhibiting all or a portion of the enzymatic activity of a ROCK kinase.

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "cyano" refers to —CN.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

As used herein, the term "heteroaryl" refers to a group having 5 to 14 ring atoms, preferably 5, 6, 10, 13 or 14 ring atoms; having 6, 10, or 14 π electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "aza-containing heteroaryl" refers to a heteroaryl group that contains a nitrogen atom in place of a carbon atom in a monocyclic, bicyclic, polycyclic or fused group having 5 to 14 ring atoms, preferably 5, 6, 10, 13 or 14 ring atoms; having 6, 10, or 14 it electrons shared in a cyclic array. "Aza-containing heteroaryl" also includes fused multicyclic (e.g., bicyclic) ring systems in which one or more of the fused rings is non-aromatic, provided that at least one ring is aromatic and at least one ring contains an N.

Exemplary aza-containing heteroaryl groups include, but are not limited to, indolizinyl, indolyl, isoindolyl, 3H-indolyl, indolinyl, indazolyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazimyl, phenothiazinyl, phenoxazinyl, 2H-pyrrolyl, pyrrolyl, 2-pyrrolinyl, 3-pyrrolinyl, oxazolyl, thiazolyl, imidazolyl, 2-imidazolinyl, pyrazolyl, 2-pyrazolinyl, isoxazolyl, isothiazolyl, 1,2,3-oxadiazolyl, 1,2,3-triazolyl, 1,3,4-thiadiazolyl, pyridyl, pyridazinyl, pyrimidinyl, and 1,3,5-triazinyl.

The term "haloalkyl" refers to an alkyl chain in which one or more hydrogens have been replaced by a halogen. Exemplary haloalkyls are trifluoromethyl, difluoromethyl, flurochloromethyl, and fluoromethyl.

The term "halogen" or "halo" as employed herein refers to chlorine, bromine, fluorine, or iodine.

The term "hydroxyl" refers to —OH.

The term "hydroxyalkyl" refers to -alkyl-OH.

As used herein, "an effective amount" of a compound is an amount that is sufficient to negatively modulate or inhibit the activity of a ROCK kinase.

As used herein, a "therapeutically effective amount" of a compound is an amount that is sufficient to ameliorate or in some manner reduce a symptom or stop or reverse progression of a condition, e.g., CCM, or negatively modulate or inhibit the activity of a ROCK kinase. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, amelioration of the symptoms of a particular disorder by administration of a particular compound or pharmaceutical composition refers to any lessening, whether permanent or temporary, lasting or transient, that can be attributed to or associated with administration of the composition.

Compounds

In one aspect of the invention, compounds are provided represented by formula (Ia), formula (Ib), formula (IIa) or formula (IIb):

Formula (I)

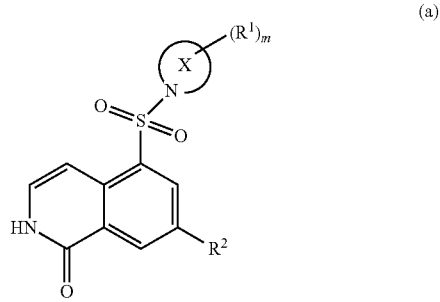

(a)

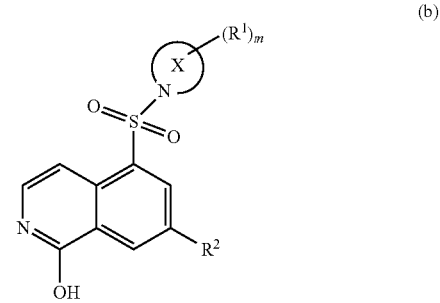

(b)

Formula (II)

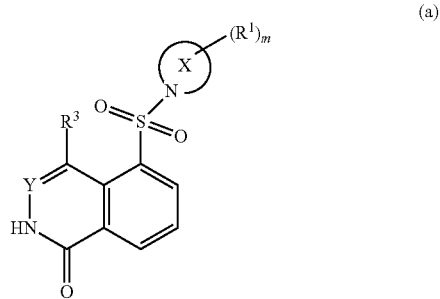

(a)

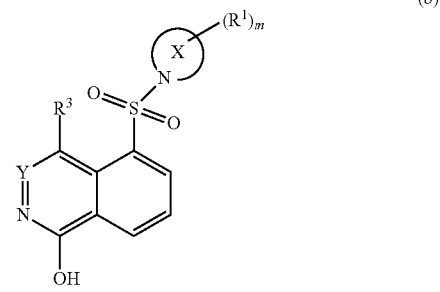

(b)

or a pharmaceutically acceptable salt thereof:
wherein:
X is a partially saturated aza-containing heteroaryl;
Y is N or CH;
each $R^1$ is cyano, hydroxyl, hydroxyalkyl, halogen, haloalkyl, alkoxy, Q-$C_1$-$C_3$ alkyl, —N($R^4$)$_2$, —N$R^4$C(O)C1-C3 alkyl or cycloalkyl;
Q is a bond, O or N;
each $R^2$ is hydrogen or halogen;

each $R^3$ is hydrogen, halogen or $C_1$-$C_3$ alkyl;
each $R^4$ is hydrogen or $C_1$-$C_3$ alkyl; and
m is 0, 1, 2 or 3.

In one aspect of the invention, X is an aza-containing heteroaryl selected from indolizinyl, indolyl, isoindolyl, 3H-indolyl, indolinyl, indazolyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazimyl, phenothiazinyl, phenoxazinyl, 2H-pyrrolyl, pyrrolyl, 2-pyrrolinyl, 3-pyrrolinyl, oxazolyl, thiazolyl, imidazolyl, 2-imidazolinyl, pyrazolyl, 2-pyrazolinyl, isoxazolyl, isothiazolyl, 1,2,3-oxadiazolyl, 1,2,3-triazolyl, 1,3,4-thiadiazolyl, pyridyl, pyridazinyl, pyrimidinyl, and 1,3,5-triazinyl. In one embodiment, X is an $R^1$-substituted indolin-1-yl.

In one embodiment, X is:

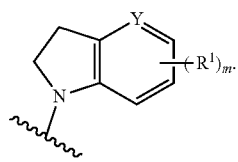

wherein m, Y and $R^1$ are as defined herein.

In one embodiment, m is one and $R^1$ is cyano, hydroxyl, hydroxyalkyl, halogen, haloalkyl, alkoxy, Q-$C_1$-$C_3$ alkyl, —N($R^4$)$_2$, —NR$^4$C(O)C1-C3 alkyl or cycloalkyl.

In one embodiment, $R^1$ is cyano. In one embodiment, $R^1$ is hydroxyl. In one embodiment, $R^1$ is halogen. In one embodiment, the halogen is chlorine or fluorine. In one embodiment, $R^1$ is haloalkyl. In one embodiment, the haloalkyl is trifluoromethyl. In one embodiment, $R^1$ is Q-$C_1$-$C_3$ alkyl. In one embodiment, Q is a bond and the $C_1$-$C_3$ alkyl is methyl, ethyl or isopropyl. In one embodiment, $R^1$ is Q-$C_1$-$C_3$ alkyl, wherein Q is O and the $C_1$-$C_3$ alkyl is methyl, ethyl or isopropyl. In one embodiment, $R^1$ is Q-$C_1$-$C_3$ alkyl, wherein Q is N and the $C_1$-$C_3$ alkyl is methyl, ethyl or isopropyl. In one embodiment, $R^1$ is hydroxyalkyl, wherein the hydroxyalkyl is hydroxymethyl. In one embodiment, $R^1$ is alkoxy. In one embodiment, the alkoxy is methoxy. In one embodiment, $R^1$ is the —N($R^4$)$_2$. In one embodiment, each $R^4$ group is hydrogen. In one embodiment, each $R^4$ group is $C_1$-$C_3$ alkyl. In one embodiment, $R^1$ is —NR$^4$C(O)C1-C3 alkyl. In one embodiment, the $R^4$ group is hydrogen and the $C_1$-$C_3$ alkyl is methyl. In one embodiment, $R^1$ is cycloalkyl, wherein the cycloalkyl is cyclopropyl.

In one embodiment, m is two and each $R^1$ is independently cyano, hydroxyl, hydroxyalkyl, halogen, haloalkyl, alkoxy, Q-$C_1$-$C_3$ alkyl, —N($R^4$)$_2$, —NR$^4$C(O)C1-C3 alkyl or cycloalkyl. In certain embodiments, each $R^1$ is halogen. In one embodiment, one $R^1$ is cyano and the other $R^1$ is hydroxyl, hydroxyalkyl, halogen, haloalkyl, alkoxy, Q-$C_1$-$C_3$ alkyl, —N($R^4$)$_2$, —NR$^4$C(O)C1-C3 alkyl or cycloalkyl.

In one embodiment, X is:

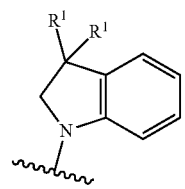

wherein each $R^1$ is hydrogen or methyl. In one embodiment, each $R^1$ is methyl.

In one embodiment, $R^2$ is halogen. In certain embodiments, the halogen is chlorine.

In one embodiment, $R^3$ is halogen or $C_1$-$C_3$ alkyl. In certain embodiments, the halogen is fluorine. In other embodiments, $R^3$ is $C_1$-$C_3$ alkyl, wherein the $C_1$-$C_3$ alkyl is methyl.

In certain embodiments, compounds of formula (Ia), formula (Ib), formula (IIa) or formula (IIb) are:

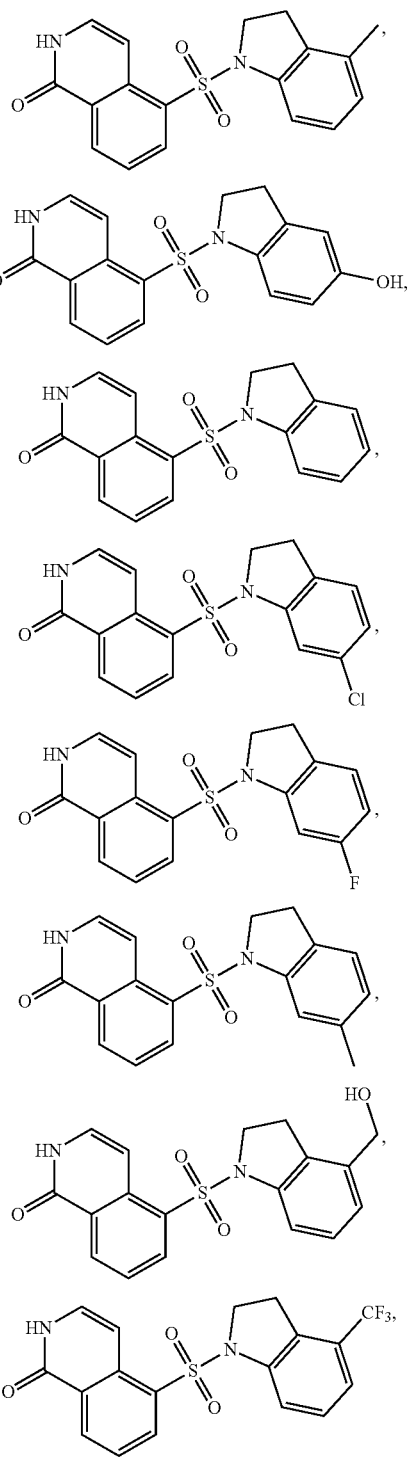

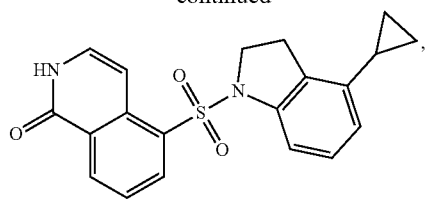
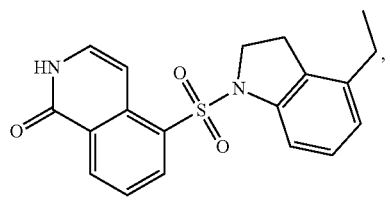
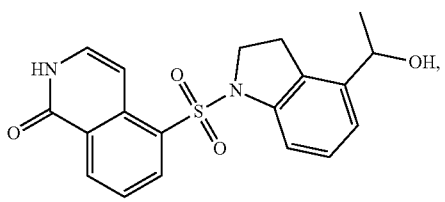
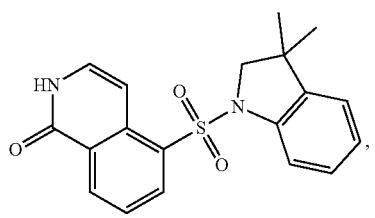
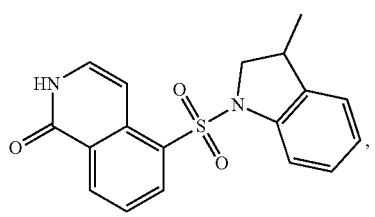
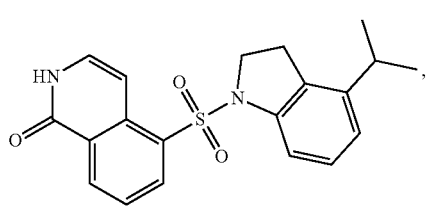
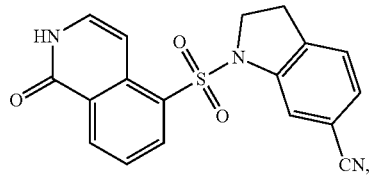
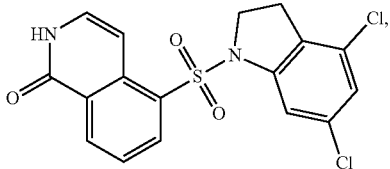
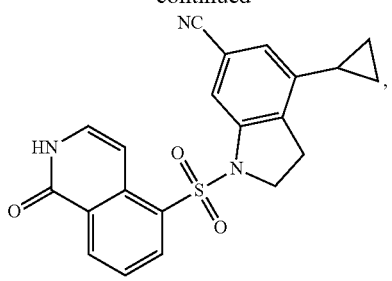
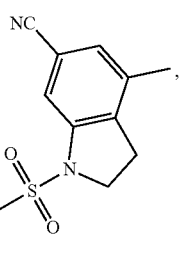
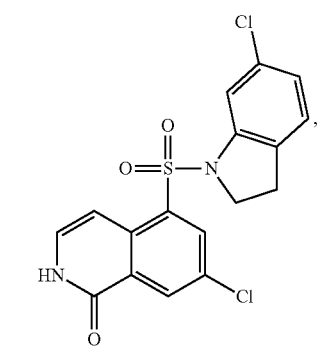
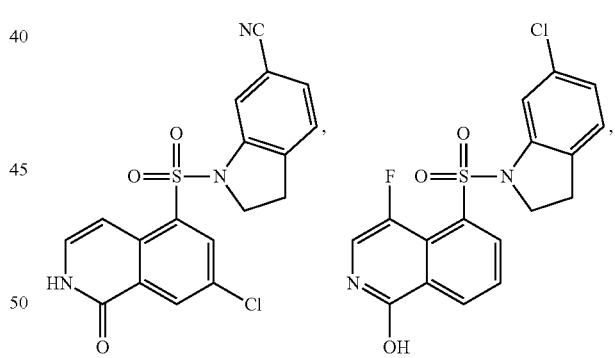
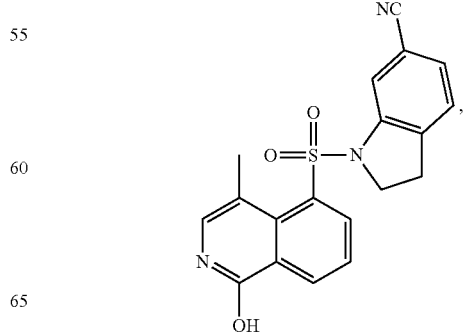

-continued
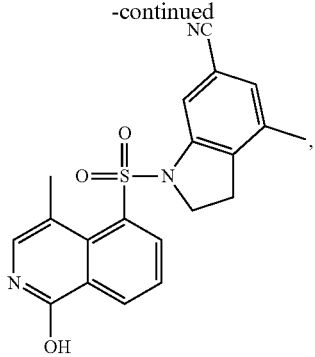
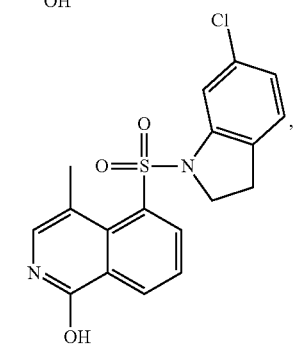
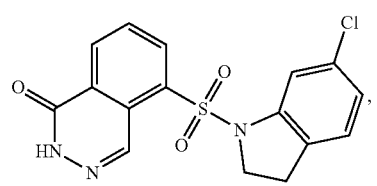
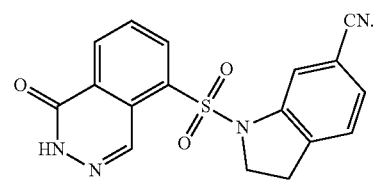
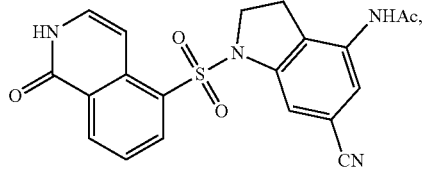
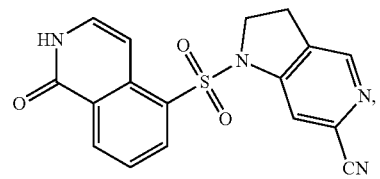
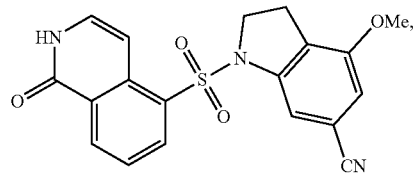
-continued
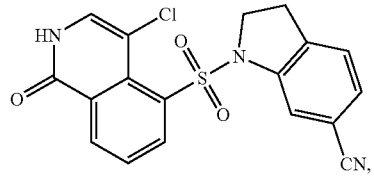
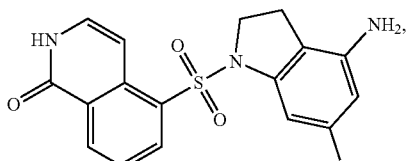
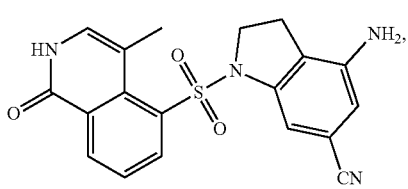
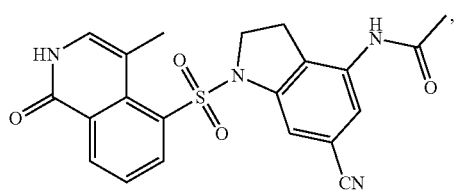
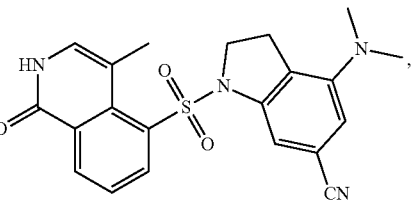
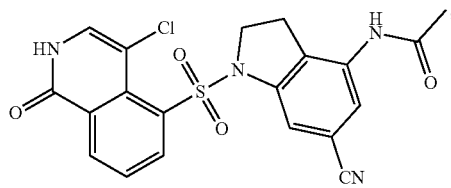
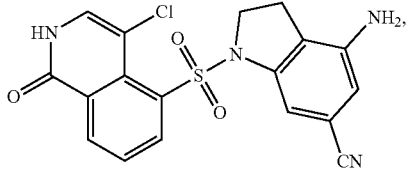
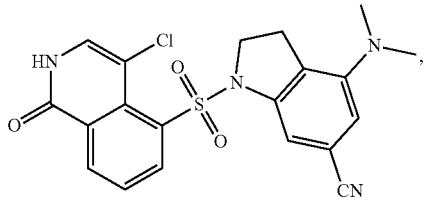
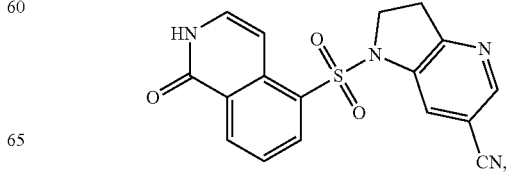

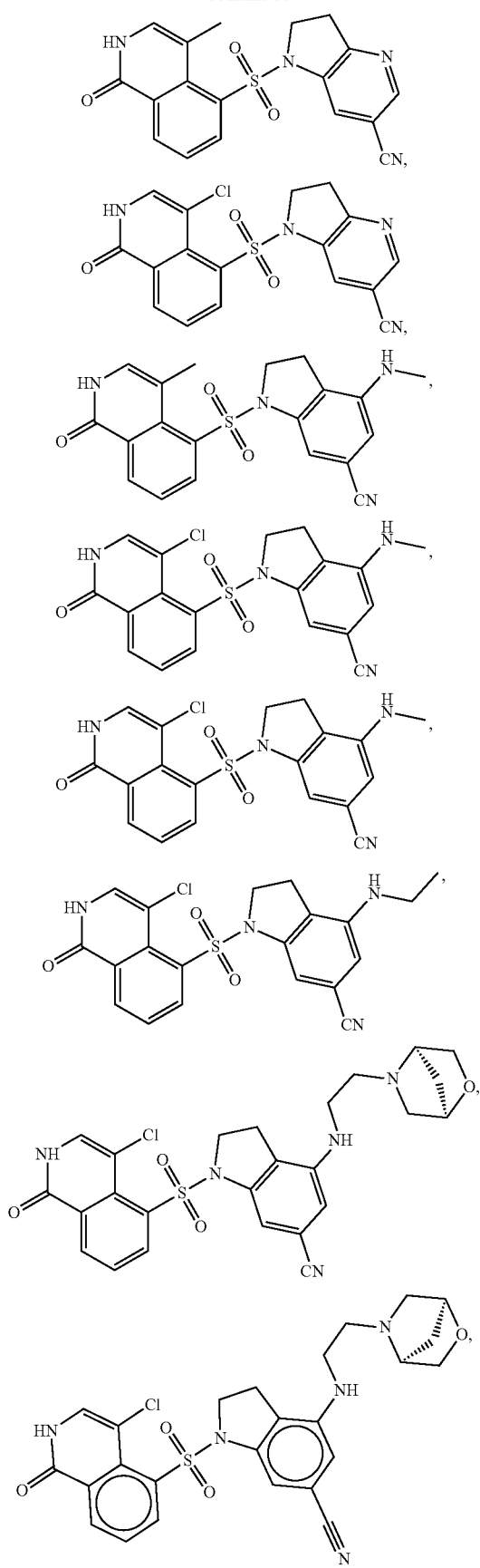
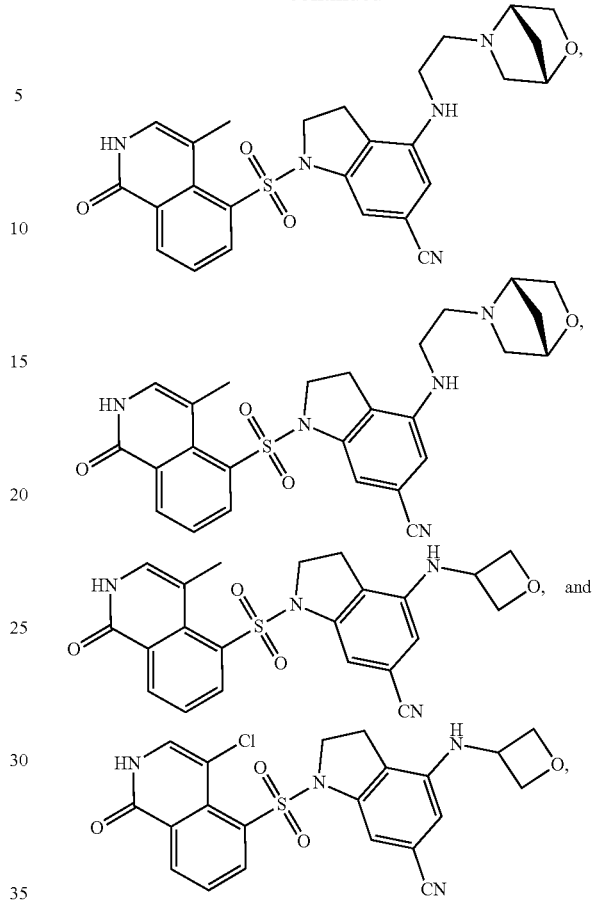

and pharmaceutically acceptable salts of the foregoing compounds.

The compounds of formula (Ia), formula (Ib), formula (IIa) or formula (IIb) may be formulated into pharmaceutical compositions.

The compounds disclosed herein include all pharmaceutically acceptable isotopically-labelled compounds, in which one or more atoms of the compounds disclosed herein are replaced by atoms having the same atomic number and an atomic mass or mass number different from the atomic mass or mass number usually found in nature. Examples of isotopes that can be incorporated into the compounds disclosed herein include isotopes of hydrogen, carbon, nitrogen, oxygen, phosphorous, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{31}$P, $^{32}$P, $^{35}$S, $^{18}$F, $^{36}$Cl, $^{123}$I, and $^{125}$I. Such radiolabeled compounds could be useful to help determine or measure the effectiveness of the compounds, for example, by characterizing binding affinities and kinetics of binding to ROCK and other modes of action. Certain compounds of the disclosure, when labelled with radioactive isotopes, such as tritium, $^3$H, and carbon-14, $^{14}$C, could also be useful in characterizing drug distribution and in vivo tissue expression of ROCK.

When labelled with heavier isotopes such as deuterium, $^2$H, compounds disclosed herein may exhibit therapeutic advantages such as greater metabolic stability, resulting in longer in-vivo half-lives, which in turn could reduce the therapeutic dosing requirements.

In order to better characterize substrate receptor occupancy or tissue expression in live specimens statically or longitudinally, replacing atoms of compounds disclosed herein with positron emitting isotopes, such as $^{11}$C, $^{14}$F, $^{15}$O and $^{13}$N, may allow for enabling Positron Emission Tomography (PET) studies.

Isotopically-labeled compounds as disclosed herein can be prepared by conventional techniques known to those skilled in the art or by processes that are analogous to those described in the associated examples and schemes using an appropriate isotopically-labeled reagent in place of the non-labeled reagent previously employed.

Some of the compounds disclosed herein may exist as stereoisomers. The compounds disclosed herein include all stereoisomers, both as pure individual stereoisomer preparations as well as preparations enriched of each, and both the racemic mixtures of such stereoisomers and the individual diasteromers and enantiomers that may be separated according to methods known to those skilled in the art. Additionally, the compounds disclosed herein include all individual tautomeric sates of the compounds and mixtures thereof.

Pharmaceutical Compositions

In another aspect, the invention provides pharmaceutical compositions comprising a ROCK kinase inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, subcutaneous, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalene-disulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting ROCK activity in a cell, comprising contacting the cell in which inhibition of ROCK activity is desired with a therapeutically effective amount of a compound of formula (Ia), formula (Ib), formula (IIa) or formula (IIb), pharmaceutically acceptable salts thereof or pharmaceutical compositions containing the compound or pharmaceutically acceptable salt thereof.

The compositions and methods provided herein are deemed particularly useful for inhibiting ROCK activity in a cell. In one embodiment, a cell in which inhibition of ROCK activity is desired is contacted with an effective amount of a compound of formula (Ia), formula (Ib), formula (IIa) or formula (IIb) to negatively modulate the activity of a ROCK kinase. In other embodiments, a therapeutically effective amount of pharmaceutically acceptable salt or pharmaceutical compositions containing the compound of formula (Ia), formula (Ib), formula (IIa) or formula (IIb) may be used. In certain embodiments, the contacting the cell with an effective amount or a therapeutically effective amount of a compound of formula (Ia), formula (Ib), formula (IIa) or formula (IIb) occurs in vivo. In certain embodiments, the contacting the cell with an effective amount or a therapeutically effective amount of a compound of formula (Ia), formula (Ib), formula (IIa) or formula (IIb) occurs in vitro. In one embodiment, the therapeutically effective amount of the compound of formula (Ia), formula (Ib), formula (IIa) or formula (IIb) is between about 0.01 to 300 mg/kg per day. In one embodiment, the therapeutically effective amount of the compound of formula (Ia), formula (Ib), formula (IIa) or formula (IIb) is between about 0.1 to 100 mg/kg per day.

In one embodiment, the compound of formula (Ia), formula (Ib), formula (IIa) or formula (IIb) preferentially inhibits the activity of ROCK2 kinase over ROCK1 kinase. In another embodiment, the compound of formula (Ia), formula (Ib), formula (IIa) or formula (IIb) inhibits the activity of ROCK2 kinase and ROCK1 kinase to a similar degree. In one embodiment, the therapeutically effective amount of the compound of formula (Ia), formula (Ib), formula (IIa) or formula (IIb) is between about 0.01 to 300 mg/kg per day. In one embodiment, the therapeutically effective amount of the compound of formula (Ia), formula (Ib), formula (IIa) or formula (IIb) is between about 0.1 to 100 mg/kg per day.

In one embodiment, methods of for treating a patient having cerebral cavernous malformation syndrome (CCM), comprising administering to the patient a therapeutically effective amount of a compound of formula (Ia), formula (Ib), formula (IIa) or formula (IIb), or a pharmaceutically acceptable salt thereof, alone or combined with a pharmaceutically acceptable carrier, excipient or diluents are provided.

In another embodiment, methods of treating a cardiovascular disease associated with increased vasotension comprising administering a therapeutically effective amount of a compound of formula (Ia), formula (Ib), formula (IIa) or formula (IIb) or pharmaceutical composition thereof to a patient in need thereof are provided. In one embodiment, the cardiovascular disease is hypertension, atherosclerosis, ischemic stroke, coronary vasospasm, cerebral vasospasm, angina and erectile dysfunction.

In embodiment, methods of treating diseases involving elevated non-vascular smooth muscle contractility comprising administering a therapeutically effective amount of a compound of formula (Ia), formula (Ib), formula (IIa) or formula (IIb) or pharmaceutical composition thereof to a patient in need thereof are provided. In one embodiment, the disease involving elevated non-vascular smooth muscle contractility asthma and glaucoma.

By negatively modulating the activity of ROCK, particularly in cases for cells overexpressing the ROCK enzyme or autosomal dominant mutations that activate the ROCK enzyme, the methods are designed to modulate the activity of ROCK, in some embodiments, to inhibit the formation of new CCMs and/or reduce or eradicate existing CCMs in treated patients or treat certain cardiovascular diseases or diseases involving elevated non-vascular smooth muscle contractility. The cells/patient may be contacted in a single dose or multiple doses in accordance with a particular treatment regimen to effect the desired negative modulation of ROCK. For example, the size and number of CCMs may be monitored using well known methods, including CT scans or MRI scans, to assess the effectiveness of treatment and dosages may be adjusted accordingly by the attending medical practitioner.

The concentration and route of administration to the patient may vary depending on the severity of the disease. The compounds, pharmaceutically acceptable salts thereof and pharmaceutical compositions comprising such compounds and salts also may be co-administered with other compounds or used in combination with other treatments, such as surgical intervention, either as an adjuvant prior to surgery or post-operatively. The degree of ROCK kinase inhibition may be monitored in the patient using well known assay methods, including those in Example A, to access the effectiveness of treatment, along with other cranial imaging techniques and instrumentation, such as CT-scans, MRIs, X-rays, etc. and dosages may be adjusted accordingly by the attending medical practitioner.

Reaction Schemes and Examples

The compounds of the present invention may be prepared using commercially available reagents using the synthetic methods and reaction schemes described herein, or using other reagents and conventional methods well known to those skilled in the art.

For instance, compounds of the present invention may be prepared according to the general reaction schemes I, II, and III.

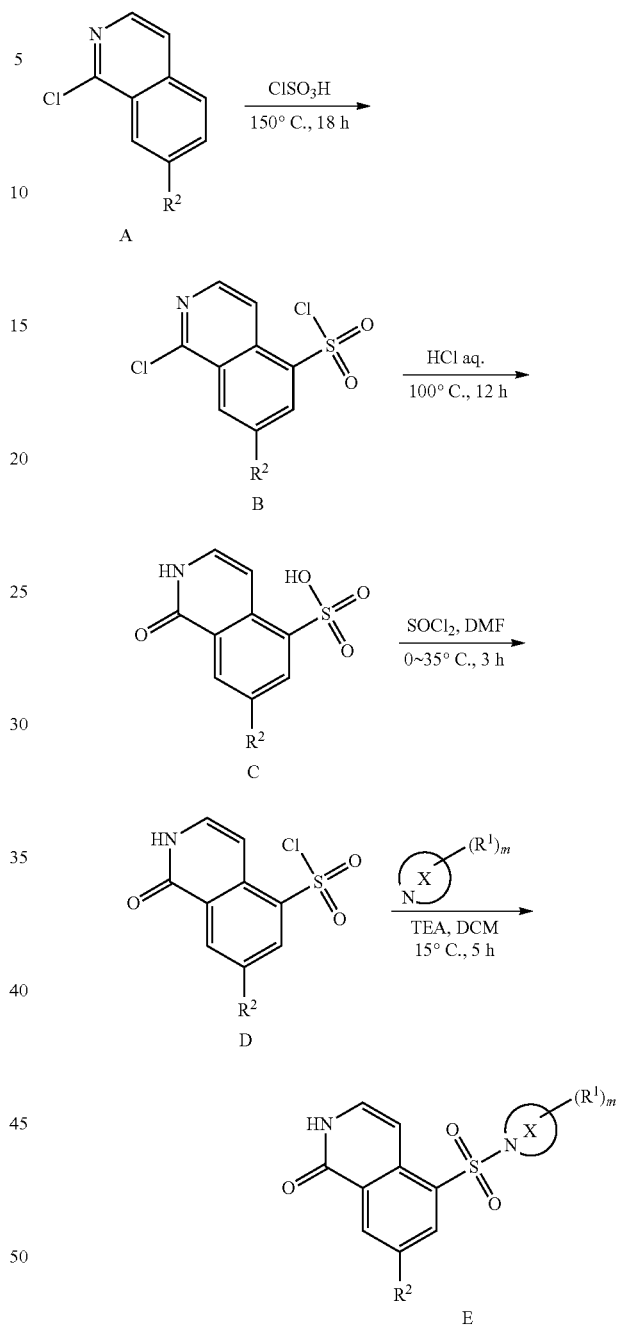

Scheme I

Scheme I illustrates the preparation of compounds of formula (I) of the present invention. An $R^2$-substituted haloisoquinoline A undergoes aromatic electrophilic substitution reaction with sulfurochloridic acid under elevated temperature to afford halosulfonated intermediate B (Step 1). Reaction of halosulfonated intermediate B under acidic conditions, e.g., HCl, and elevated temperature affords sulfonic acid substituted isoquinolinone C (Step 2). The sulfonic acid is converted to the sulfonyl chloride typically using sulfuryl chloride in DMF at reduced temperatures (Step 3). The addition of $R^1$-substituted aza-containing heteroaryl X typically proceeds under basic conditions using an appropriate base such as TEA in a solvent such as DCM to afford compounds E of formula (I) (Step 4).

Scheme II

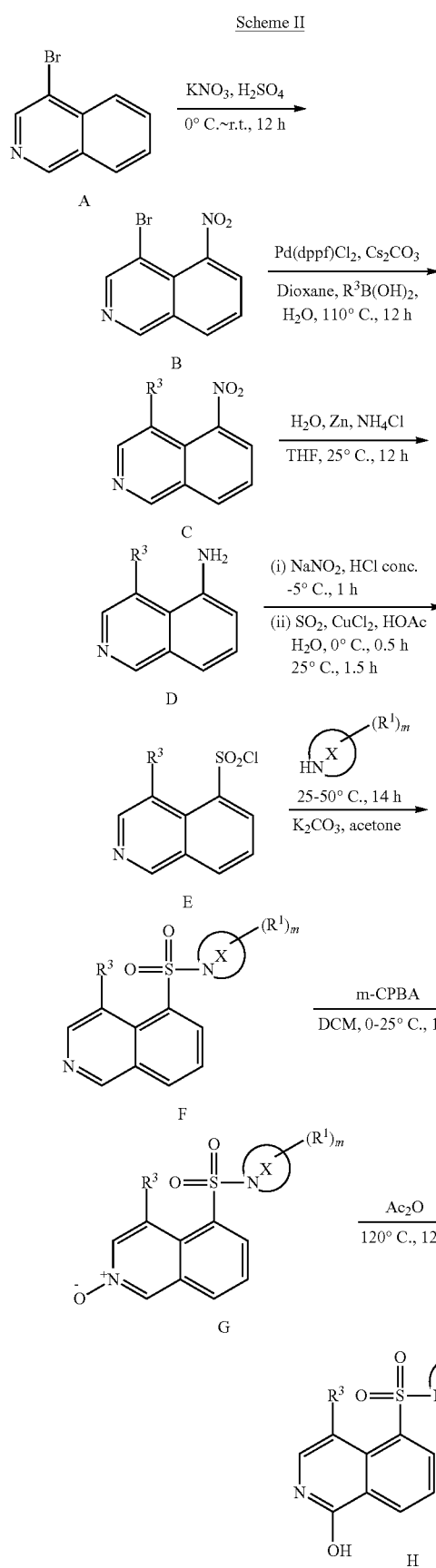

Scheme II illustrates the preparation of compounds of formula (II) of the present invention, wherein $R^3$ is $C_1$-$C_3$ alkyl. Nitration of halo-substituted isoquinoline A is carried out using nitric acid in the presence of sulfuric acid under reduced temperatures, e.g., 0° C. to produce nitro-substituted compound B. Boronic acid $R^3B(OH)_2$ is coupled to intermediate B via a Suzuki reaction using an appropriate palladium catalyst, e.g., Pd(dddf)Cl$_2$, in the presence of a suitable base, e.g., CsCO$_3$ in dioxane, to generate $R^3$-substituted compound C. Nitro-containing compound C is reduced to the amine D. Amine D is reacted with sodium nitrite under acidic conditions and then treated with CuCl$_2$ and SO$_2$ to give sulfonyl chloride E. The addition of $R^1$-substituted aza-containing heteroaryl X typically proceeds under basic conditions using an appropriate base such as TEA in a solvent such as DCM to afford compounds F. Reaction with m-CPBA gives N-oxide G. Treating N-oxide G with acetic anhydride with heating gives the acetate that undergoes spontaneous 2,3-sigmatropic rearrangement. Deprotection of the acetate provides 1-oxo compound H.

Scheme III

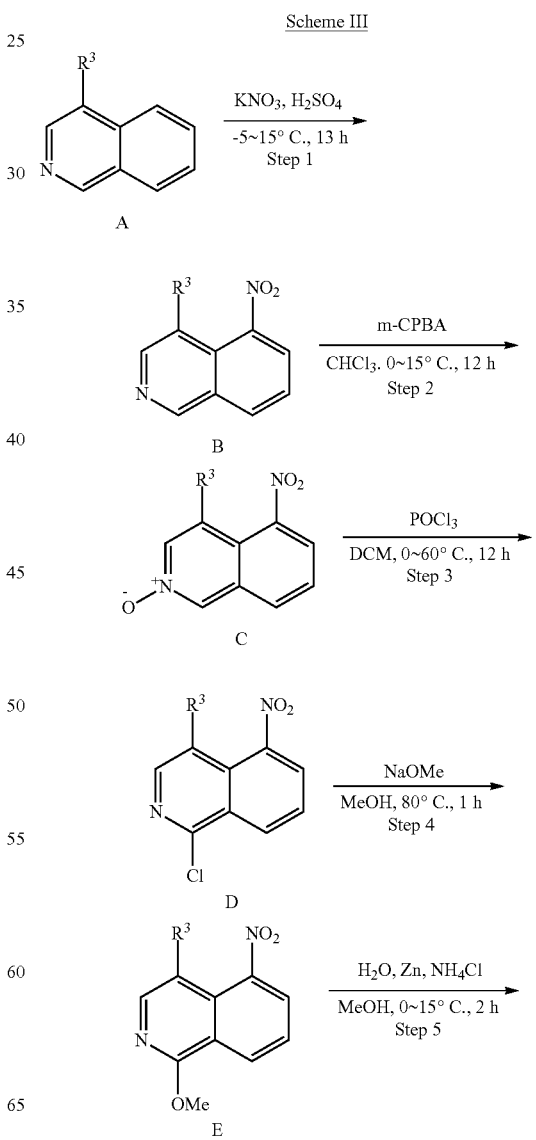

21

-continued

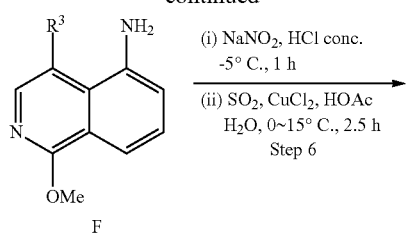

F (i) NaNO₂, HCl conc.
-5° C., 1 h
(ii) SO₂, CuCl₂, HOAc
H₂O, 0~15° C., 2.5 h
Step 6

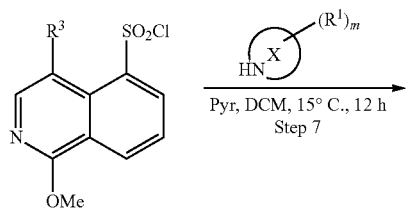

G $(R^1)_m$ $\underset{\text{Step 7}}{\xrightarrow{\text{Pyr, DCM, 15° C., 12 h}}}$

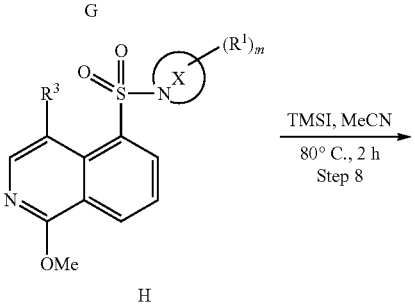

H $\underset{\text{Step 8}}{\xrightarrow{\text{TMSI, MeCN}\atop\text{80° C., 2 h}}}$

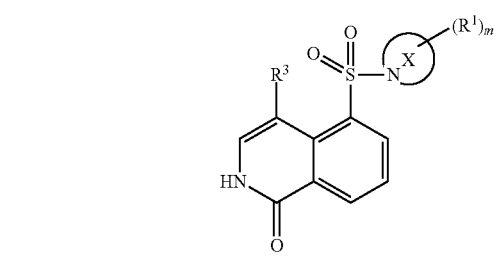

I

Scheme III illustrates the preparation of compounds of formula (II) of the present invention, wherein $R^3$ is halogen. 4-Haloisoquinoline A is nitrated, for example with with $H_2SO_4$ and $KNO_3$ to furnish nitro haloisoquinoline compound B. Nitroisoquinoline B is treated with oxidant, for example m-CPBA to provide N-oxide C which is further reacted with a chlorinating agent such as $POCl_3$ to afford dihaloisoquinoline compound D. Compound D undergoes SNAr substitution with an oxygen nucleophile for example sodium methoxide to give methoxyisoquinoline compound E. Compound E was reduced, for example with Zn to isoquinolinamine compound F. Compound F was subjected to Sanmeyer reaction conditions for example with $NaNO_2$, HCl, $SO_2$ and CuCl to impart isoquinolinesulfonyl chloride compound G. The addition of $R^1$-substituted aza-containing heteroaryl X to compound G typically proceeds under basic conditions for example pyridine in a solvent such as DCM to afford sulfonamide compound H. Compound H was deprotected for example with trimethylsilyl iodide to cede isoquinolinone compound I of Formula II.

The following Examples are intended to illustrate further certain embodiments of the invention and are not intended to limit the scope of the invention.

22

Example 1

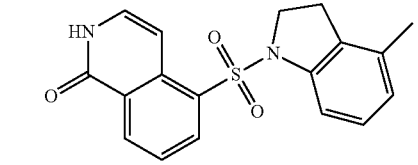 [SMILES: Cc1cccc2c1CCN2S(=O)(=O)c1cccc2c(=O)[nH]ccc12]

5-((4-Methylindolin-1-yl)sulfonyl)isoquinolin-1(2H)-one

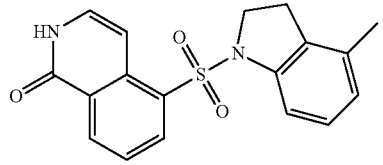

1-1

$\xrightarrow{\text{ClSO}_3\text{H}\atop\text{150° C., 18 h}}$

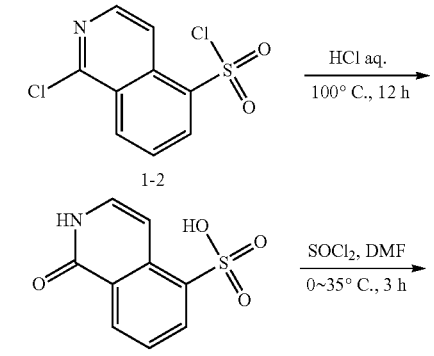

1-2

$\xrightarrow{\text{HCl aq.}\atop\text{100° C., 12 h}}$

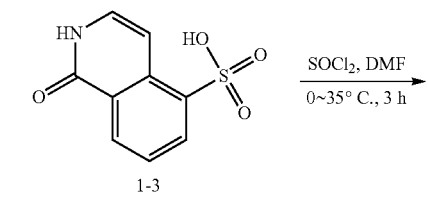

1-3

$\xrightarrow{\text{SOCl}_2\text{, DMF}\atop\text{0~35° C., 3 h}}$

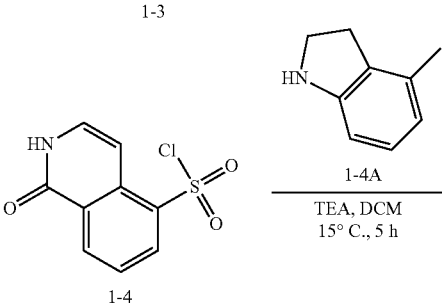

1-4

$\xrightarrow[\text{TEA, DCM}\atop\text{15° C., 5 h}]{\text{1-4A}}$

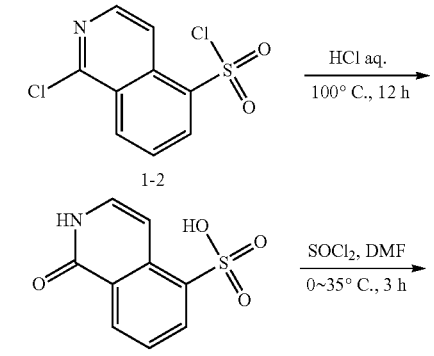

EXAMPLE 1

Compound 1-2: A solution of 1-chloroisoquinoline (5 g, 30.5 mmol) in sulfurochloridic acid (50 mL, 750.9 mmol) was stirred at 150° C. for 12 h under an $N_2$ atmosphere. The reaction mixture was quenched by adding ice and then was diluted with $H_2O$ (300 mL) and extracted with DCM (100 mL×3). The combined organic layers were washed with saturated brine (300 mL), dried over anhydrous $Na_2SO_4$, filtered and concentrated under reduced pressure to give a residue. The residue was purified by column chromatography (SiO$_2$, petroleum ether:ethyl acetate=0:1 to 10:1). Compound 1-2, 1-chloroisoquinoline-5-sulfonyl chloride (19.1 g, 72.9 mmol, 47.7% yield), was obtained as a yellow solid.

Compound 1-3: To a solution of 1-chloroisoquinoline-5-sulfonyl chloride (2.5 g, 9.54 mmol) in HCl aq. solution (30 mL, 9 N, 276.9 mmol) was stirred at 100° C. for 12 h under an N$_2$ atmosphere. The reaction mixture was filtered and concentrated under reduced pressure to give a residue. The crude product, Compound 1-3, 1-hydroxyisoquinoline-5-sulfonic acid (2.8 g, crude), was obtained as a yellow solid and was used in the next step without further purification.

Compound 1-4: To a solution of 1-hydroxyisoquinoline-5-sulfonic acid (0.8 g, 3.55 mmol) in SOCl$_2$ (40 mL) was added DMF (273 µL, 3.55 mmol) at 0° C. and the mixture was stirred at 15° C. for 30 min under an N$_2$ atmosphere. Then the mixture was stirred at 35° C. for 2.5 h under an N$_2$ atmosphere. The reaction mixture was diluted with H$_2$O (100 mL) and extracted with DCM (200 mL×3). The combined organic layers were washed with saturated brine (100 mL), dried over anhydrous Na$_2$SO$_4$, filtered and concentrated under reduced pressure to give a residue. The crude product, Compound 1-4, 1-hydroxyisoquinoline-5-sulfonyl chloride (0.3 g, 1.23 mmol, 34.6% yield), was obtained as a yellow solid. The compound was used in the next step without further purification.

EXAMPLE 1: To a solution of 1-hydroxyisoquinoline-5-sulfonyl chloride (150 mg, 615.6 µmol) in DCM (10 mL) was added TEA (128.5 µL, 923.4 µmol) and 4-methylindoline (90.1 mg, 677.1 µmol). The mixture was stirred at 15° C. for 5 h under an N$_2$ atmosphere. The reaction mixture was diluted with H$_2$O (60 mL) and extracted with DCM (200 mL×2). The combined organic layers were washed with saturated brine (80 mL), dried over anhydrous Na$_2$SO$_4$, filtered and concentrated under reduced pressure to give a residue. The residue was purified by column chromatography (SiO$_2$, petroleum ether:ethyl acetate=10:1 to 1:1). EXAMPLE 1, 5-(4-methylindolin-1-yl)sulfonyl-2H-isoquinolin-1-one (90 mg, 252 µmol, 41.1% yield), was obtained as a white solid. LC-MS: [M+1] 340.09.

$^1$H NMR (400 MHz, DMSO-d$_6$): δ 11.65 (br, 1H), 8.48 (d, J=8 Hz, 1H), 8.26 (d, J=7.6 Hz, 1H), 7.59 (t, J=7.6 Hz, 1H), 7.34 (t, J=6 Hz, 1H), 7.20~7.02 (m, 3H), 6.81 (d, J=7.6 Hz, 1H), 4.04 (t, J=8.0 Hz, 2H), 2.89 (t, J=8 Hz, 2H), 2.11 (s, 3H).

Example 2

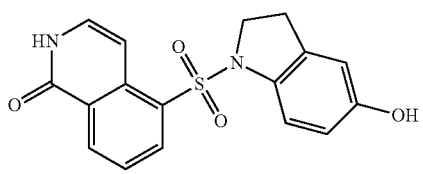 [SMILES: O=c1[nH]ccc2c(S(=O)(=O)N3CCc4cc(O)ccc43)cccc12]

5-((5-Hydroxyindolin-1-yl)sulfonyl)isoquinolin-1 (2H)-one

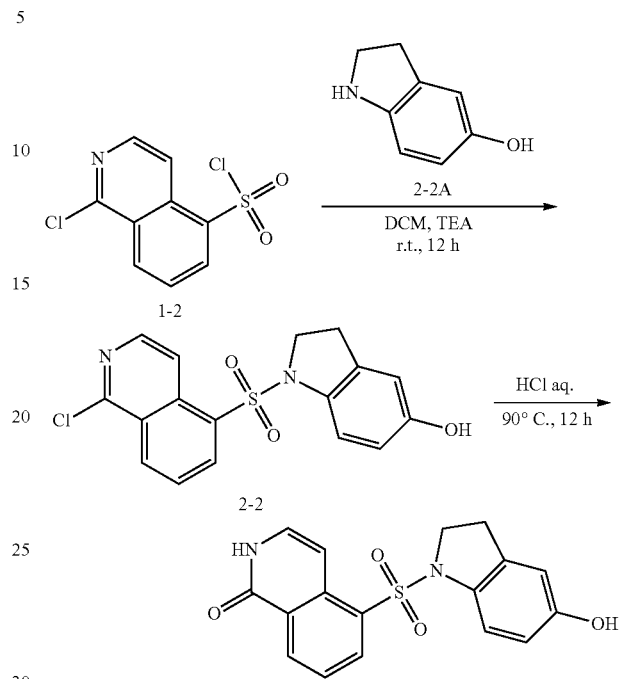

EXAMPLE 2

Compound 2-2: To a solution of 1-chloroisoquinoline-5-sulfonyl chloride (0.4 g, 1.53 mmol) in DCM (10 mL) was added TEA (318 µL, 2.29 mmol) and indolin-5-ol (226.9 mg, 1.68 mmol). The mixture was stirred at 25° C. for 12 h under an N$_2$ atmosphere. The reaction mixture was filtered and concentrated under reduced pressure to give a residue. The residue was purified by column chromatography (SiO$_2$, petroleum ether:ethyl acetate=10:1 to 1:1). Compound 2-2, 1-[(1-chloro-5-isoquinolyl) sulfonyl]indolin-5-ol (350 mg, 970.0 µmol, 63.6% yield), was obtained as a yellow solid.

EXAMPLE 2: A solution of 1-[(1-chloro-5-isoquinolyl) sulfonyl]indolin-5-ol (330 mg, 914.6 µmol) in HCl (10 mL, 9 N) was stirred at 90° C. for 12 h under an N$_2$ atmosphere. The reaction mixture was quenched by addition of saturated NaHCO$_3$ solution until pH=7, and then diluted with H$_2$O (30 mL) and extracted with EtOAc (10 mL×3). The combined organic layers were washed with saturated brine (30 mL), dried over anhydrous Na$_2$SO$_4$, filtered and concentrated under reduced pressure to give a residue. The residue was purified by prep-HPLC (column: Waters Xbridge Prep OBD C18 150 mm×40 mm×10 m; mobile phase: [A, water (10 mM NH$_4$HCO$_3$)—B, ACN]; B %: 25%-55%, 11 min). EXAMPLE 2, 5-(5-hydroxyindolin-1-yl)sulfonyl-2H-isoquinolin-1-one (6 mg, 17.1 µmol, 1.87% yield), was obtained as a yellow solid. LC-MS: [M+1] 342.07.

$^1$H NMR (400 MHz, CDCl3): δ 10.16 (br, 1H), 8.73 (d, J=8 Hz, 1H), 8.20 (d, J=8.8 Hz, 1H), 7.56~7.44 (m, 2H), 7.38~7.30 (m, 1H), 6.74 (s, 1H), 6.43 (d, J=6.4 Hz, 1H), 6.35 (d, J=8.4 Hz, 1H), 3.54 (t, J=8.4 Hz, 2H), 2.93 (t, J=8.4 Hz, 2H). One proton was exchanged.

Example 3

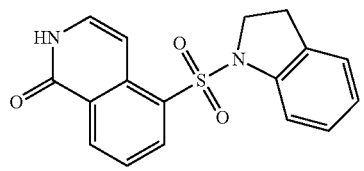 [SMILES: O=c1[nH]ccc2c(S(=O)(=O)N3CCc4ccccc43)cccc12]

5-(Indolin-1-ylsulfonyl)isoquinolin-1(2H)-one

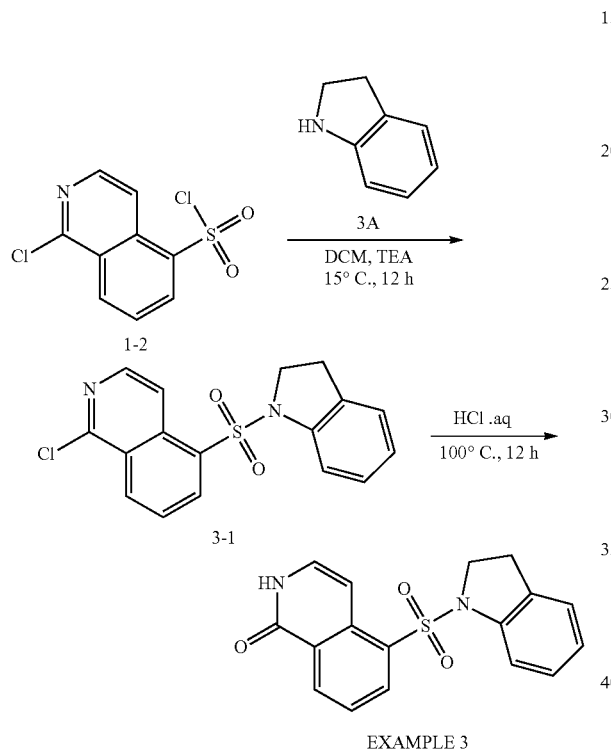

EXAMPLE 3

Compound 3-1: To a solution of 1-chloroisoquinoline-5-sulfonyl chloride (0.3 g, 1.14 mmol) in DCM (8 mL) was added TEA (238.9 μL, 1.72 mmol) and indoline (109.1 mg, 915.6 tmol). The mixture was stirred at 15° C. for 12 h under an $N_2$ atmosphere. The reaction mixture was diluted with $H_2O$ (60 mL) and extracted with EtOAc (100 mL×3). The combined organic layers were washed with saturated brine (50 mL), dried over anhydrous $Na_2SO_4$, filtered and concentrated under reduced pressure to give a residue. The crude product, Compound 3-1, 1-chloro-5-indolin-1-ylsulfonyl-isoquinoline (0.2 g, crude) was obtained as a yellow solid. Compound 3-1 was used in the next step without further purification.

EXAMPLE 3: A mixture of 1-chloro-5-indolin-1-ylsulfonyl-isoquinoline (0.2 g, 580.02 μmol, 1 eq) in HCl aq. solution (5 mL, 12M) was stirred at 100° C. for 12 h under an $N_2$ atmosphere. The reaction mixture was quenched by addition of ice water (15 mL) at 0° C., and then $NaHCO_3$ was added to the mixture to adjust to pH 8 and filtered. The filtrate was concentrated under reduced pressure to give a residue. The residue was partitioned between $H_2O$ (60 mL) and DCM (100 mL×3). The combined organic layers were washed with saturated brine (50 mL), dried over anhydrous $Na_2SO_4$, filtered and concentrated under reduced pressure to give a residue. The residue was purified by column chromatography ($SiO_2$, petroleum ether:ethyl acetate=10:1 to 0:1). EXAMPLE 3, 5-indolin-1-ylsulfonyl-2H-isoquinolin-1-one (40 mg, 117.5 μmol, 20.2% yield), was obtained as a white solid. LC-MS: [M+1] 326.07.

$^1$H NMR (400 MHz, MeOD): δ 8.58 (d, J=8.4 Hz, 1H), 8.34 (d, J=8 Hz, 1H), 7.61 (t, J=8 Hz, 1H), 7.47 (d, J=8 Hz, 1H), 7.38 (d, J=7.6 Hz, 1H), 7.25~7.10 (m, 3H), 7.00 (t, J=8 Hz, 1H), 4.03 (t, J=8 Hz, 2H), 2.85 (t, J=8.4 Hz, 2H). One proton was exchanged.

Example 4

5-((6-Chloroindolin-1-yl)sulfonyl)isoquinolin-1(2H)-one

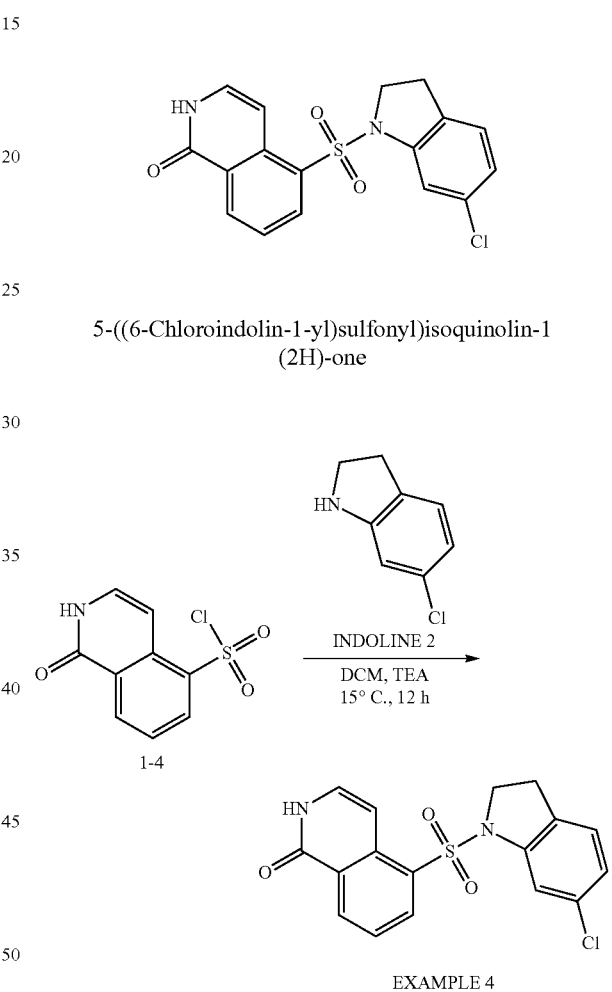

EXAMPLE 4

EXAMPLE 4: To a solution of 1-hydroxyisoquinoline-5-sulfonyl chloride (100.0 mg, 410.4 μmol) in DCM (5 mL) was added TEA (85.7 μL, 615.6 μmol) and 6-chloroindoline Indoline 2 (56.7 mg, 369.4 μmol). The mixture was stirred at 15° C. for 12 h under an $N_2$ atmosphere. The reaction mixture was diluted with $H_2O$ (50 mL) and extracted with DCM (150 mL×2). The combined organic layers were washed with saturated brine (100 mL), dried over anhydrous $Na_2SO_4$, filtered and concentrated under reduced pressure to give a residue. The residue was purified by column chromatography ($SiO_2$, Pether:ethyl acetate=8:1 to 0:1). 40 mg of EXAMPLE 4, 5-(6-chloroindolin-1-yl) sulfonyl-2H-isoquinolin-1-one, was obtained as a white solid. LC-MS: [M+1] 360.03.

¹H NMR (400 MHz, MeOD): δ 8.60 (d, J=8 Hz, 1H), 8.35 (d, J=8 Hz, 1H), 7.63 (t, J=8 Hz, 1H), 7.45 (d, J=2 Hz, 1H), 7.37 (d, J=7.6 Hz, 1H), 7.26 (d, J=7.6 Hz, 1H), 7.10 (d, J=7.6 Hz, 1H), 7.02~6.96 (m, 1H), 4.03 (t, J=8.4 Hz, 2H), 2.87 (t, J=8.4 Hz, 2H). One proton was exchanged.

Example 5

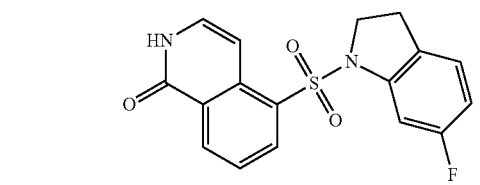 [SMILES: O=c1[nH]ccc2c(S(=O)(=O)N3CCc4ccc(F)cc43)cccc12]

5-((6-Fluoroindolin-1-yl)sulfonyl)isoquinolin-1(2H)-one

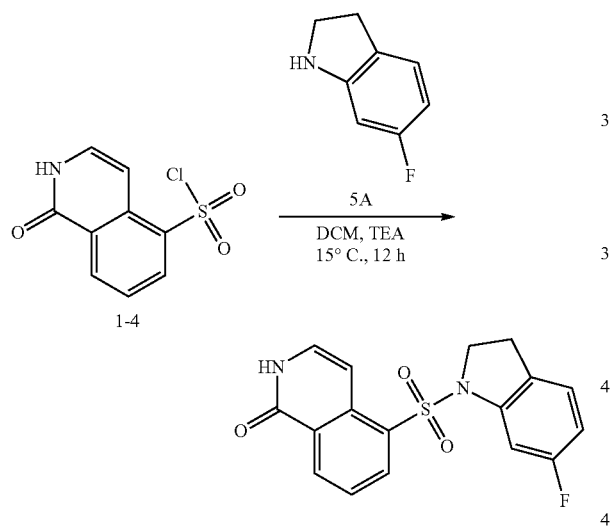

EXAMPLE 5

Example 6

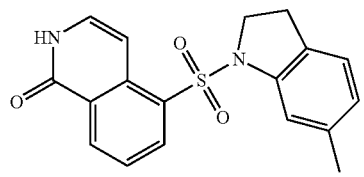 [SMILES: Cc1ccc2c(c1)N(S(=O)(=O)c1cccc3c(=O)[nH]ccc13)CC2]

5-((6-Methylindolin-1-yl)sulfonyl)isoquinolin-1(2H)-one

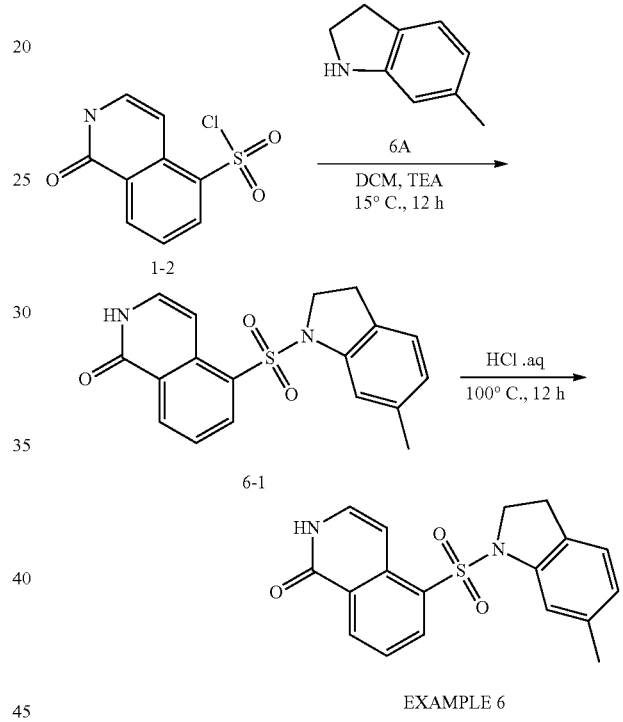

EXAMPLE 6

EXAMPLE 5: To a solution of 1-hydroxyisoquinoline-5-sulfonyl chloride (150.0 mg, 615.6 μmol) in DCM (5 mL) was added 6-fluoroindoline 5A (75.9 mg, 554.0 μmol) and TEA (128.5 μL, 923.3 μmol). The mixture was stirred at 15° C. for 12 h under an N₂ atmosphere. The reaction mixture was diluted with H₂O (30 mL) and extracted with DCM (100 mL×2). The combined organic layers were washed with saturated brine (50 mL), dried over anhydrous Na₂SO₄, filtered and concentrated under reduced pressure to give a residue. The residue was purified by column chromatography (SiO₂, petroleum ether:ethyl acetate=10:1 to 0:1). EXAMPLE 5, 5-(6-fluoroindolin-1-yl)sulfonyl-2H-isoquinolin-1-one (80 mg, 204.3 μmol, 33.2% yield), was obtained as a yellow solid. LC-MS: [M+1] 344.06.

¹H NMR (400 MHz, MeOD): δ 8.59 (d, J=8.0 Hz, 1H), 8.36 (d, J=7.6 Hz, 1H), 7.62 (t, J=8 Hz, 1H), 7.38 (d, J=8 Hz, 1H), 7.26 (d, J=7.6 Hz, 1H), 7.22~7.17 (m, 1H), 7.12~7.06 (m, 1H), 6.75~6.66 (m, 1H), 4.03 (t, J=8.4 Hz, 2H), 2.87 (t, J=8.4 Hz, 2H). One proton was exchanged.

Compound 6-1: To a solution of 1-chloroisoquinoline-5-sulfonyl chloride (0.3 g, 1.14 mmol) in DCM (8 mL) was added TEA (239 μL, 1.72 mmol) and 6-methylindoline 6A (121 mg, 916 μmol). The mixture was stirred at 15° C. for 12 h under an N₂ atmosphere. The reaction mixture was diluted with H₂O (60 mL) and extracted with EtOAc (100 mL×3). The combined organic layers were washed with saturated brine (50 mL), dried over anhydrous Na₂SO₄, filtered and concentrated under reduced pressure to give a residue. The crude product, compound 6-1, 1-chloro-5-(6-methylindolin-1-yl)sulfonyl-isoquinoline (0.2 g, crude), was obtained as a yellow solid. The crude product was used in the next step without further purification.

EXAMPLE 6: A mixture of 1-chloro-5-(6-methylindolin-1-yl) sulfonyl-isoquinoline (0.2 g, 557 μmol) in HCl aq. solution (5 mL, 12 M) was degassed and purged with N₂ 3 times, and then the mixture was stirred at 100° C. for 12 h under an N₂ atmosphere. The reaction mixture was quenched by the addition of ice water (15 mL) at 0° C., and then NaHCO₃ was added to the mixture to adjust to pH 8 and filtered. The filtrate was concentrated under reduced pressure to give a residue. The reaction mixture was diluted with H₂O (60 mL) and extracted with DCM (100 mL×3). The combined organic layers were washed with saturated brine (50 mL), dried over anhydrous Na₂SO₄, filtered and concentrated under reduced pressure to give a residue. The residue was purified by column chromatography (SiO₂, petroleum ether:ethyl acetate=10:1 to 0:1). EXAMPLE 6, 5-(6-methylindolin-1-yl)sulfonyl-2H-isoquinolin-1-one (40 mg, 107.4 µmol, 19.2% yield), was obtained as a white solid. LC-MS: [M+1] 340.09.

¹H NMR (400 MHz, MeOD): δ 8.57 (d, J=8.4 Hz, 1H), 8.32 (d, J=7.6 Hz, 1H), 7.59 (t, J=8 Hz, 1H), 7.38 (d, J=8 Hz, 1H), 7.30 (s, 1H), 7.22 (d, J=8 Hz, 1H), 6.99 (d, J=7.6 Hz, 1H), 6.82 (d, J=7.6 Hz, 1H), 4.01 (t, J=8 Hz 2H), 2.79 (t, J=8 Hz 2H), 2.31 (s, 3H). One proton was exchanged.

Example 7

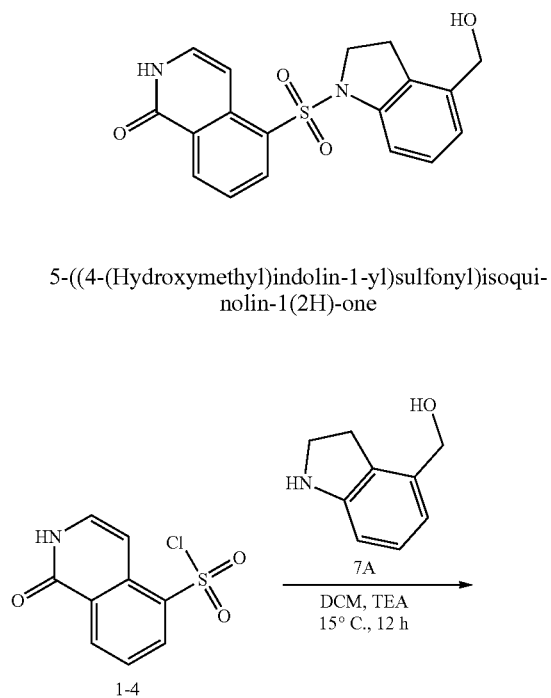

5-((4-(Hydroxymethyl)indolin-1-yl)sulfonyl)isoquinolin-1(2H)-one

EXAMPLE 7

EXAMPLE 7: To a solution of 1-oxo-2H-isoquinoline-5-sulfonyl chloride (0.3 g, 1.23 mmol) in DCM (10 mL) was added TEA (257.0 µL, 1.85 mmol) and indolin-4-ylmethanol 7A (202.0 mg, 1.35 mmol). The mixture was stirred at 25° C. for 12 h under an N₂ atmosphere. The reaction mixture was diluted with H₂O (15 mL) and extracted with DCM (5 mL×3). The combined organic layers were washed with saturated brine (15 mL), dried over anhyrdous Na₂SO₄, filtered and concentrated under reduced pressure to give a residue. The residue was purified by column chromatography (SiO₂, petroleum ether:ethyl acetate=1:0 to 0:1). EXAMPLE 7, 5-[4-(hydroxymethyl)indolin-1-yl] sulfonyl-2H-isoqu-inolin-1-one (35 mg, 91.59 mol, 7.44% yield), was obtained as a black brown solid. LC-MS: [M+1] 356.08.

¹H NMR (400 MHz, MeOD): δ 8.56 (d, J=8.0 Hz, 1H), 8.34 (d, J=7.6 Hz, 1H), 7.58 (t, J=7.6 Hz, 1H), 7.50 (d, J=8 Hz, 2H), 7.22 (d, J=8 Hz, 1H), 7.17 (t, J=8 Hz, 1H), 7.04 (d, J=7.6 Hz, 1H), 4.46 (s, 2H), 4.06 (t, J=8.4 Hz, 2H), 2.91 (t, J=8.4 Hz, 2H). Two protons were exchanged.

Example 8

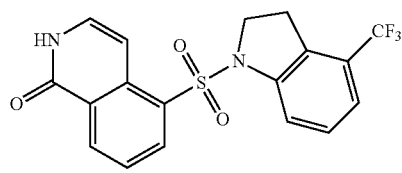 [SMILES: O=c1[nH]ccc2c(S(=O)(=O)N3CCc4c3cccc4C(F)(F)F)cccc12]

5-((4-(Trifluoromethyl)indolin-1-yl)sulfonyl)isoquinolin-1(2H)-one

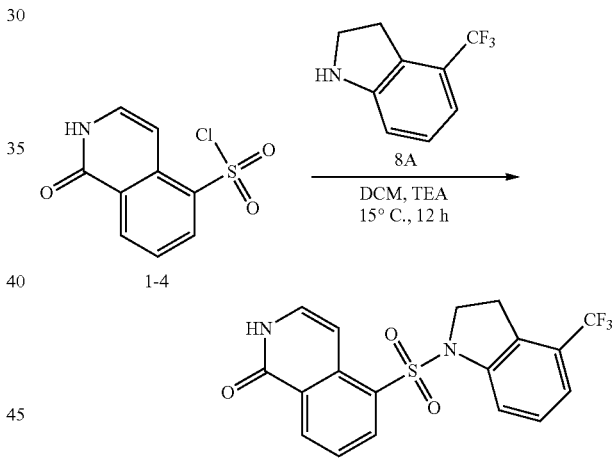

EXAMPLE 8

EXAMPLE 8: To a solution of 1-hydroxyisoquinoline-5-sulfonyl chloride (150 mg, 615 µmol) in DCM (5 mL) was added TEA (128.5 µL, 923.3 µmol) and 4-(trifluoromethyl) indoline 8A (103.6 mg, 554.0 µmol). The mixture was stirred at 15° C. for 12 h under an N₂ atmosphere. The reaction mixture was diluted with H₂O (30 mL) and extracted with DCM (75 mL×2). The combined organic layers were washed with saturated brine (20 mL), dried over anhydrous Na₂SO₄, filtered and concentrated under reduced pressure to give a residue. The residue was purified by column chromatography (SiO₂, petroleum ether:ethyl acetate=10:1 to 0:1). EXAMPLE 8, 5-[4-(trifluoromethyl)indolin-1-yl] sulfonyl-2H-isoquinolin-1-one (20 mg, 44.2 µmol, 7.18% yield), was obtained as a white solid. LC-MS: [M+1] 394.06.

¹H NMR (400 MHz, MeOD): δ 8.60 (d, J=8 Hz, 1H), 8.38 (d, J=7.6 Hz, 1H), 7.70 (d, J=8.4 Hz, 1H), 7.63 (t, J=8 Hz,

1H), 7.40~7.20 (m, 4H), 4.10 (t, J=8.4 Hz, 2H), 3.05 (t, J=8.4 Hz, 2H). One proton was exchanged.

Example 9

5-((4-Cyclopropylindolin-1-yl)sulfonyl)isoquinolin-1(2H)-one

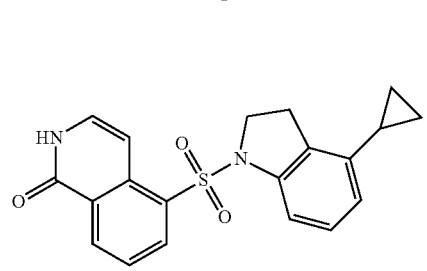 [SMILES: O=c1[nH]ccc2c(S(=O)(=O)N3CCc4c(C5CC5)cccc43)cccc12]

EXAMPLE 9

EXAMPLE 9: To a solution of 1-hydroxyisoquinoline-5-sulfonyl chloride (150 mg, 615.5 µmol) in DCM (5 mL) was added TEA (128.5 µL, 923.3 µmol) and 4-cyclopropylindoline INDOLINE 22 (88.2 mg, 554.0 µmol). The mixture was stirred at 15° C. for 12 h under an $N_2$ atmosphere. The reaction mixture was diluted with $H_2O$ (40 mL) and was extracted with DCM (100 mL×2). The combined organic layers were washed with saturated brine (20 mL), dried over anhydrous $Na_2SO_4$, filtered and concentrated under reduced pressure to give a residue. The residue was purified by column chromatography ($SiO_2$,petroleum ether:ethyl acetate=10:1 to 0:1). EXAMPLE 9, 5-(4-cyclopropylindolin-1-yl)sulfonyl-2H-isoqui-nolin-1-one (25 mg, 57.8 µmol, 9.39% yield), was obtained as a white solid. LC-MS: [M+1] 366.10.

$^1$H NMR (400 MHz, MeOD): δ 8.57 (d, J=7.6 Hz, 1H), 8.33 (d, J=7.6 Hz, 1H), 7.59 (t, J=8 Hz, 1H), 7.33 (d, J=8 Hz, 1H), 7.26 (d, J=8 Hz, 1H), 7.19 (d, J=8 Hz, 1H), 7.07 (t, J=7.6 Hz, 1H), 6.56 (d, J=7.6 Hz, 1H), 4.05 (t, J=8.4 Hz, 1H), 2.93 (t, J=8.4 Hz, 2H), 1.73~1.67 (m, 1H), 0.88~0.86 (m, 2H), 0.57~0.55 (m, 2H).

Example 10

5-((4-ethylindolin-1-yl)sulfonyl)isoquinolin-1(2H)-one

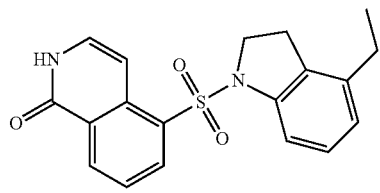 [SMILES: CCc1cccc2c1CCN2S(=O)(=O)c1cccc2c(=O)[nH]ccc12]

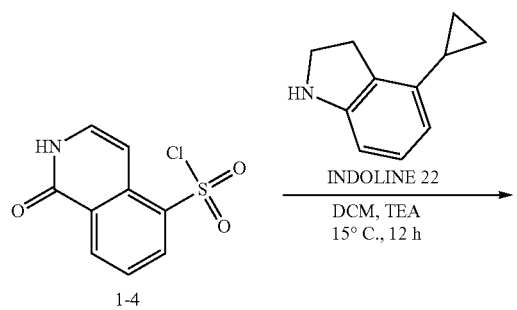

EXAMPLE 10

Compound 10-1: To a solution of 1-hydroxyisoquinoline-5-sulfonyl chloride (150 mg, 615.5 µmol) in DCM (5 mL) was added TEA (128.5 µL, 923.3 µmol) and 4-vinylindoline INDOLINE 20 (98.3 mg, 677.1 µmol). The mixture was stirred at 15° C. for 12 h under an $N_2$ atmosphere. The reaction mixture was diluted with $H_2O$ (20 mL) and extracted with DCM (80 mL×2). The combined organic layers were washed with saturated brine (30 mL), dried over anhydrous $Na_2SO_4$, filtered and concentrated under reduced pressure to give a residue. The residue was purified by column chromatography ($SiO_2$, petroleum ether:ethyl acetate=10:1 to 0:1). Compound 10-1, 5-(4-vinylindolin-1-yl)sulfonyl-2H-isoquinolin-1-one (50 mg, 141.8 µmol, 23.05% yield), was obtained as a yellow solid.

EXAMPLE 10: A mixture of 5-(4-vinylindolin-1-yl) sulfonyl-2H-isoquinolin-1-one (50 mg, 141.8 µmol), Pd/C (5 mg, 10 wt %) in MeOH (5 mL) was degassed and purged with $H_2$ 3 times, and then the mixture was stirred at 15° C.

for 12 h under $H_2$ atmosphere (15 psi). The reaction mixture was filtered and the filter was concentrated. The residue was purified by column chromatography ($SiO_2$, petroleum ether: ethyl acetate=5:1 to 0:1). The residue was purified by prep-HPLC (column: Waters Xbridge 150 mm×50 mm×10 µm; mobile phase:[A, water (10 mM $NH_4HCO_3$)—B, ACN]; B %: 30%-60%, 12 min). EXAMPLE 10, 5-(4-ethylindolin-1-yl)sulfonyl-2H-isoquinolin-1-one (14 mg, 39.4 µmol, 27.7% yield), was obtained as a white solid. LC-MS: [M+1] 354.10.

$^1$H NMR (400 MHz, MeOD): δ 8.58 (d, J=7.6 Hz, 1H), 8.34 (d, J=7.6 Hz, 1H), 7.60 (t, J=8 Hz, 1H), 7.32 (t, J=7.2 Hz, 2H), 7.18 (d, J=4.0 Hz, 1H), 7.13 (t, J=7.6 Hz, 1H), 6.88 (d, J=4 Hz, 1H), 4.03 (t, J=8.4 Hz, 2H), 2.76 (t, J=8.4 Hz, 2H), 2.50–2.44 (m, 2H), 1.06 (t, J=7.6 Hz, 3H). One proton was exchanged.

Example 11

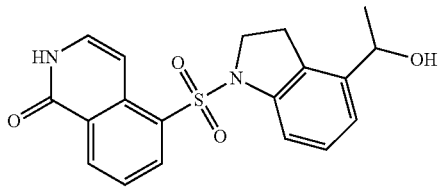 [SMILES: CC(O)c1cccc2c1CCN2S(=O)(=O)c1cccc2c(=O)[nH]ccc12]

5-((4-(1-Hydroxyethyl)indolin-1-yl)sulfonyl)isoquinolin-1(2H)-one

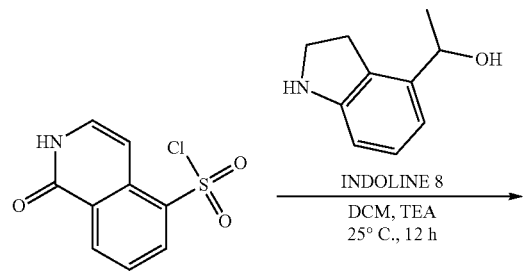

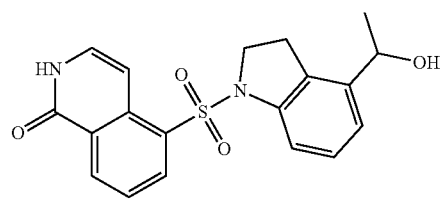

EXAMPLE 11

EXAMPLE 11: To a solution of 1-oxo-2H-isoquinoline-5-sulfonyl chloride (244.2 mg, 1.00 mmol) in DCM (5 mL) was added TEA (209.3 µL, 1.50 mmol) and 1-indolin-4-ylethanol INDOLINE 8 (180 mg, 1.10 mmol). The mixture was stirred at 25° C. for 12 h under an $N_2$ atmosphere. The reaction mixture was diluted with $H_2O$ (60 mL) and extracted with DCM (150 mL×2). The combined organic layers were washed with saturated brine (50 mL), dried over anhydrous $Na_2SO_4$, filtered and concentrated under reduced pressure to give a residue. The residue was purified by column chromatography ($SiO_2$, petroleum ether:ethyl acetate=10:1 to 0:1). The residue was purified by prep-HPLC (column: Waters Xbridge 150 mm×25 mm×5 µm; mobilephase:[A, water (10 mM $NH_4HCO_3$)—B, ACN]; B %: 10%-40%, 10 min). EXAMPLE 11, 5-[4-(1-hydroxyethyl)indolin-1-yl]sulfonyl-2H-isoquinolin-1-one (40 mg), was obtained as a white solid. LC-MS: [M+1] 370.10.

$^1$H NMR (400 MHz, MeOD): δ 8.57 (d, J=7.6 Hz, 1H), 8.35 (d, J=8 Hz, 1H), 7.59 (t, J=8 Hz, 1H), 7.38 (d, J=8, 1H), 7.34 (d, J=8 Hz, 1H), 7.21-7.15 (m, 2H), 7.11 (d, J=7.6 Hz, 1H), 4.88-4.71 (m, 1H), 4.07-4.01 (m, 2H), 2.89-2.80 (m, 2H), 1.26 (d, J=6.4 Hz, 3H). Two protons were exchanged.

Example 12

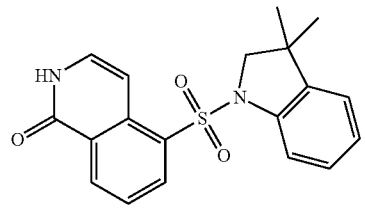 [SMILES: CC1(C)CN(S(=O)(=O)c2cccc3c(=O)[nH]ccc23)c2ccccc21]

5-((3,3-Dimethylindolin-1-yl)sulfonyl)isoquinolin-1(2H)-one

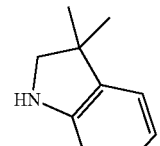

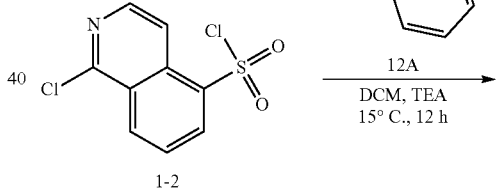

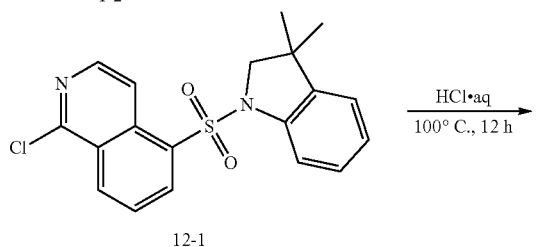

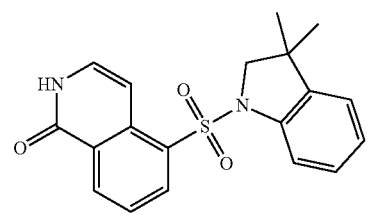

EXAMPLE 12

Compound 12-1: To a solution of 1-chloroisoquinoline-5-sulfonyl chloride (0.3 g, 1.14 mmol) in DCM (8 mL) was added TEA (238.9 µL, 1.72 mmol) and 3,3-dimethylindoline 12A (134.8 mg, 915.6 μmol). The mixture was stirred at 15° C. for 12 h under an N₂ atmosphere. The reaction mixture was diluted with H₂O (60 mL) and extracted with EtOAc (100 mL×3). The combined organic layers were washed with saturated brine (50 mL), dried over anhydrous Na₂SO₄, filtered and concentrated under reduced pressure to give a residue. The crude product Compound 12-1, 1-chloro-5-(3,3-dimethylindolin-1-yl)sulfonyl-isoquinoline (0.2 g, crude), was obtained as a yellow solid. The crude product was used in the next step without further purification.

EXAMPLE 12: A mixture of 1-chloro-5-(3,3-dimethylindolin-1-yl)sulfonyl-isoquinoline (0.2 g, 536.3 μmol) in HCl aq. solution (5 mL, 12 M) was degassed and purged with N₂ 3 times, and then the mixture was stirred at 100° C. for 12 h under an N₂ atmosphere. The reaction mixture was quenched by the addition of ice water (15 mL) at 0° C., and then NaHCO₃ was added to the mixture to adjust to pH 8, filtered and the filtrate was concentrated under reduced pressure to give a residue. The residue was diluted with H₂O (60 mL) and extracted with DCM (100 mL×3). The combined organic layers were washed with saturated brine (50 mL), dried over anhydrous Na₂SO₄, filtered and concentrated under reduced pressure to give a residue. The residue was purified by column chromatography (SiO₂, petroleum ether:ethyl acetate=10:1 to 0:1). EXAMPLE 12, 5-(3,3-dimethylindolin-1-yl)sulfonyl-2H-isoquinolin-1-one (12 mg, 31.5 μmol, 5.88% yield), was obtained as a white solid. LC-MS: [M+1] 354.10.

¹H NMR (400 MHz, MeOD): δ 8.58, (d, J=8 Hz, 1H), 8.42 (d, J=8 Hz, 1H), 7.62 (t, J=7.6 Hz, 1H), 7.48 (d, J=8 Hz, 1H), 7.43 (d, J=7.6 Hz, 1H), 7.23 (d, J=7.6 Hz, 1H), 7.18 (t, J=7.6 Hz, 1H), 7.11 (d, J=7.6 Hz, 1H), 7.02 (t, J=7.6 Hz, 1H), 3.73 (s, 2H), 1.08 (s, 6H). One proton was exchanged.

Example 13

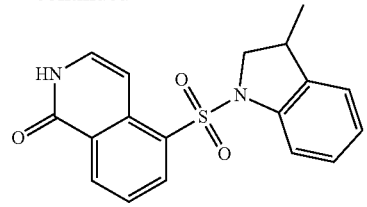

EXAMPLE 13

EXAMPLE 13: To a solution of 1-hydroxyisoquinoline-5-sulfonyl chloride (100 mg, 410.4 μmol) in DCM (5 mL) was added TEA (85.6 μL, 615.6 μmol) and 3-methylindoline (55.7 mg, 328.3 μmol). The mixture was stirred at 15° C. for 12 h under an N₂ atmosphere. The reaction mixture was diluted with H₂O (50 mL) and extracted with DCM (150 mL×2). The combined organic layers were washed with saturated brine (50 mL), dried over anhydrous Na₂SO₄, filtered and concentrated under reduced pressure to give a residue. The residue was purified by column chromatography (SiO₂,petroleum ether:ethyl acetate=10:1 to 0:1). 70 mg of EXAMPLE 13, 5-(3-methylindolin-1-yl) sulfony 1-2H-isoquinolin-1-one, was obtained as a white solid. LC-MS: [M+1] 340.09.

¹H NMR (400 MHz, DMSO-d₆): δ 11.67 (s, 1H), 8.49 (d, J=8 Hz, 1H), 8.30 (d, J=8 Hz, 1H), 7.61 (t, J=7.6 Hz, 1H), 7.31~7.30 (m, 2H), 7.20~7.13 (m, 3H), 7.01 (t, J=7.6 Hz, 1H), 4.19 (t, J=9.2 Hz, 1H), 3.57-3.53 (m, 1H), 3.29~3.24 (m, 1H), 1.05 (d, J=6.8 Hz, 3H).

Example 14

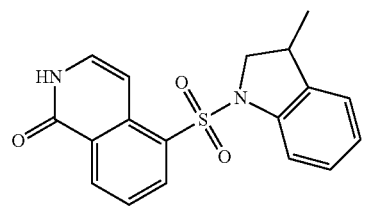 [SMILES: CC1CN(S(=O)(=O)c2cccc3c(=O)[nH]ccc23)c2ccccc21]

5-((3-Methylindolin-1-yl)sulfonyl)isoquinolin-1(2H)-one

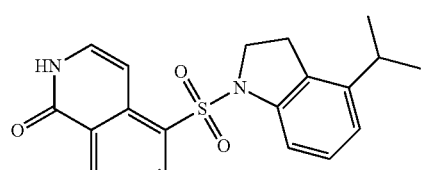

5-((4-Isopropylindolin-1-yl)sulfonyl)isoquinolin-1(2H)-one

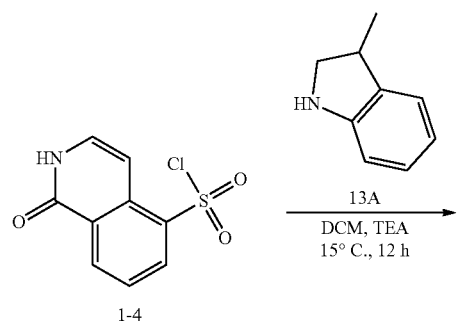

1-4

13A
DCM, TEA
15° C., 12 h

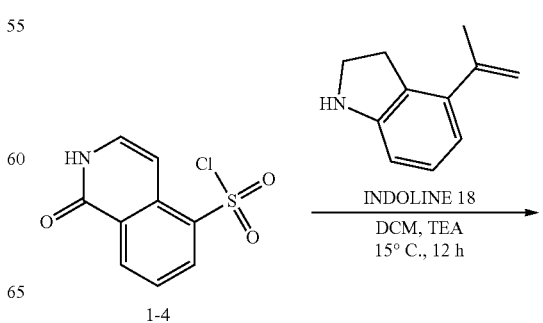

1-4

INDOLINE 18
DCM, TEA
15° C., 12 h

38

1-((1-Oxo-1,2-dihydroisoquinolin-5-yl)sulfonyl)indoline-6-carbonitrile

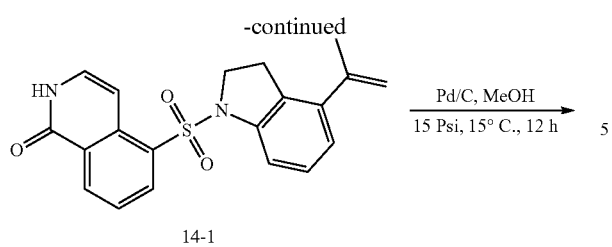

14-1

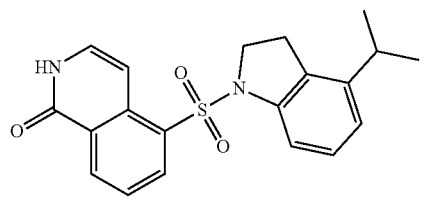

EXAMPLE 14

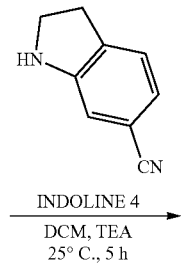

1-4

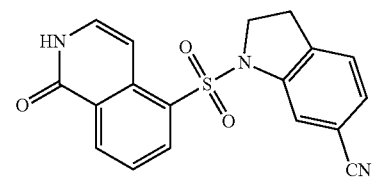 [SMILES: N#Cc1ccc2c(c1)N(S(=O)(=O)c1cccc3c(=O)[nH]ccc13)CC2]

EXAMPLE 15

Compound 14-1: To a solution of 1-hydroxyisoquinoline-5-sulfonyl chloride (83.4 mg, 342.6 μmol) in DCM (5 mL) was added TEA (71.5 μL, 513.8 μmol) and 4-isopropenylindoline INDOLINE 18 (60 mg, 376.82 μmol). The mixture was stirred at 15° C. for 12 h under an $N_2$ atmosphere. The reaction mixture was diluted with $H_2O$ (10 mL) and extracted with DCM (50 mL×3). The combined organic layers were washed with saturated brine (10 mL), dried over anhydrous $Na_2SO_4$, filtered and concentrated under reduced pressure to give a residue. The residue was purified by column chromatography ($SiO_2$, petroleum ether:ethyl acetate=10:1 to 1:1). Compound 14-1,5-(4-isopropenylindolin-1-yl)sulfonyl-2H-isoquinolin-1-one (50 mg, 136.4 μmol, 39.8% yield), was obtained as a yellow solid.

EXAMPLE 14: To a solution of 5-(4-isopropenylindolin-1-yl)sulfonyl-2H-isoquinolin-1-one (50 mg, 136.45 μmol, 1 eq) in MeOH (5 mL) was added Pd/C (5 mg, 10% purity) under $H_2$. The mixture was stirred at 15° C. for 12 h with a pressure of 15 psi. The reaction mixture was filtered and the filtrate was concentrated. The residue was purified by column chromatography ($SiO_2$, petroleum ether:ethyl acetate=5:1 to 0:1). The residue was purified by prep-HPLC (column: Waters Xbridge 150 mm×50 mm×10 um; mobile phase: [A, water (10 mM $NH_4HCO_3$)—B, ACN];B %: 30%-60%, 12 min). EXAMPLE 14, 5-(4-isopropylindolin-1-yl)sulfonyl-2H-isoquinolin-1-one (8 mg, 21.50 μmol, 15.7% yield), was obtained as a white solid. LC-MS: [M+1] 368.12.

$^1$H NMR (400 MHz, MeOD): δ 8.57 (d, J=8.0 Hz, 1H), 8.34 (d, J=6.8 Hz, 1H), 7.59 (t, J=8 Hz, 1H), 7.32-7.26 (m, 2H), 7.15 (t, J=7.6 Hz, 2H), 6.95 (d, J=7.6 Hz, 1H), 4.00 (t, J=8 Hz, 2H), 2.81~2.71 (m, 3H), 1.10 (d, J=6.8 Hz, 6H). One proton was exchanged.

EXAMPLE 15: To a solution of 1-hydroxyisoquinoline-5-sulfonyl chloride (202.8 mg, 832.3 μmol) in DCM (5 mL) was added TEA (173.8 μL, 1.25 mmol) and indoline-6-carbonitrile INDOLINE 4 (120 mg, 832.3 μmol). The mixture was stirred at 25° C. for 5 h under an $N_2$ atmosphere. The reaction mixture was quenched by addition $H_2O$ (40 mL), then the reaction mixture was extracted with DCM (100 mL×2). The combined organic layers were washed with saturated brine 50 (mL), dried over anhydrous $Na_2SO_4$, filtered and concentrated under reduced pressure to give a residue. The residue was purified by column chromatography ($SiO_2$, petroleum ether:ethyl acetate=10:1 to 0:1). EXAMPLE 15, 1-[(1-oxo-2H-isoquinolin-5-yl)sulfonyl]indoline-6-carbonitrile (80 mg, 215.8 μmol, 25.9% yield), was obtained as a yellow solid. LC-MS: [M+1] 351.07.

$^1$H NMR (400 MHz, DMSO-$d_6$): δ 11.68 (s, 1H), 8.51 (d, J=7.6 Hz, 1H), 8.37 (d, J=6.4 Hz, 1H), 7.64 (t, J=8 Hz, 1H), 7.58 (s, 1H), 7.47-7.40 (m, 3H), 7.11 (d, J=7.2 Hz, 1H), 4.06 (t, J=8 Hz, 2H), 3.07 (t, J=8.0 Hz, 2H).

Example 15

Example 16

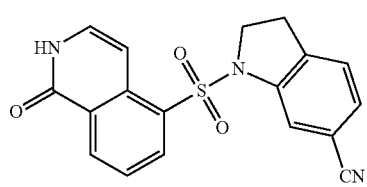

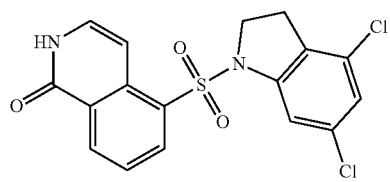 [SMILES: O=c1[nH]ccc2c(S(=O)(=O)N3CCc4c(Cl)cc(Cl)cc43)cccc12]

5-((4,6-Dichloroindolin-1-yl)sulfonyl)isoquinolin-1(2H)-one

4-Cyclopropyl-1-((1-oxo-1,2-dihydroisoquinolin-5-yl)sulfonyl)indoline-6-carbonitrile

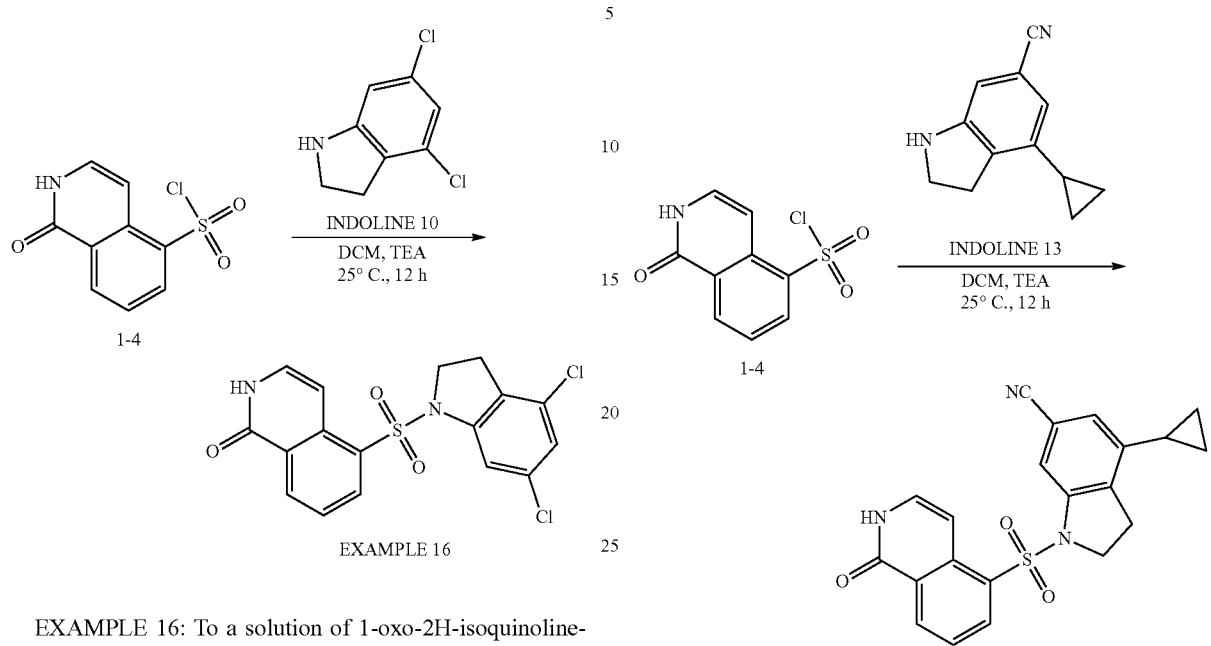

EXAMPLE 16: To a solution of 1-oxo-2H-isoquinoline-5-sulfonyl chloride (176.6 mg, 725.1 μmol) in DCM (3 mL) was added TEA (151.3 μL, 1.09 mmol) and 4,6-dichloroindoline INDOLINE 10 (150 mg, 797.6 μmol). The mixture was stirred at 25° C. for 12 h under an $N_2$ atmosphere. The reaction mixture was diluted with $H_2O$ (60 mL) and extracted with DCM (150 mL×2). The combined organic layers were washed with saturated brine (50 mL), dried over anhydrous $Na_2SO_4$, filtered and concentrated under reduced pressure to give a residue. The residue was purified by column chromatography ($SiO_2$, petroleum ether:ethyl acetate=10:1 to 0:1). The residue was purified by prep-HPLC (column: Waters Xbridge Prep OBD C18 150 mm×40 mm×10 μm; mobile phase: [A, water (10 mM $NH_4HCO_3$)—B,ACN];B %: 35%-55%, 11 min). EXAMPLE 16, 5-(4,6-dichloroindolin-1-yl)sulfonylisoquinolin-1-ol (60 mg, 150.5 μmol, 20.7% yield), was obtained as a white solid. LC-MS: [M+1] 393.99.

$^1$H NMR (400 MHz, DMSO-$d_6$): δ 8.53 (d, J=7.6 Hz, 1H), 8.31 (d, J=8 Hz, 2H), 7.67 (t, J=8 Hz, 1H), 7.39 (d, J=7.6 Hz, 1H) 7.23 (d, J=8.8 Hz, 2H), 7.10 (d, J=7.6 Hz, 1H), 4.09 (t, J=8.4 Hz, 2H), 3.03 (t, J=8.4 Hz, 2H).

EXAMPLE 17: To a solution of 1-oxo-2H-isoquinoline-5-sulfonyl chloride (50 mg, 205.2 μmol) in DCM (5 mL) was added TEA (85.6 μL, 615.6 μmol) and 4-cyclopropylindoline-6-carbonitrile INDOLINE 13 (37.8 mg, 205.2 μmol). The mixture was stirred at 25° C. for 12 h under an $N_2$ atmosphere. The reaction mixture was diluted with $H_2O$ (15 mL) and extracted with DCM (80 mL×2). The combined organic layers were washed with saturated brine (10 mL), dried over anhydrous $Na_2SO_4$, filtered and concentrated under reduced pressure to give a residue. The residue was purified by prep-HPLC (column: Xtimate C18 150 mm×25 mm×5 m; mobile phase: [A, water (10 mM $NH_4HCO_3$)—B, ACN]; B %: 50%-80%, 10 min). EXAMPLE 17, 4-cyclopropyl-1-[(1-hydroxy-5-isoquinolyl)sulfonyl]indoline-6-carbonitrile (19 mg, 47.5 μmol, 23.1% yield), was obtained as a yellow solid. LC-MS: [M+1] 391.10.

$^1$H NMR (400 MHz, MeOD): δ 8.62 (d, J=8 Hz, 1H), 8.39 (d, J=6.8 Hz, 1H), 7.65 (t, J=7.8 Hz, 1H), 7.54 (s, 1H), 7.35 (d, J=7.6 Hz, 1H), 7.27 (d, J=7.6 Hz, 1H), 6.92 (s, 1H), 4.09 (t, J=8.4 Hz, 2H), 3.07 (t, J=8.4 Hz, 2H), 1.79~1.77 (m, 1H), 0.98~0.95 (m, 2H), 0.68-0.66 (m, 2H). One proton was exchanged.

Example 17

Example 18

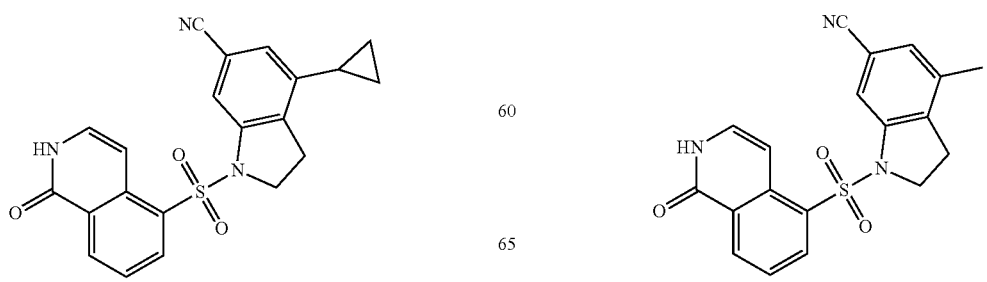

4-Methyl-1-((1-oxo-1,2-dihydroisoquinolin-5-yl)sulfonyl)indoline-6-carbonitrile

7-Chloro-5-((6-chloroindolin-1-yl)sulfonyl)isoquinolin-1(2H)-one

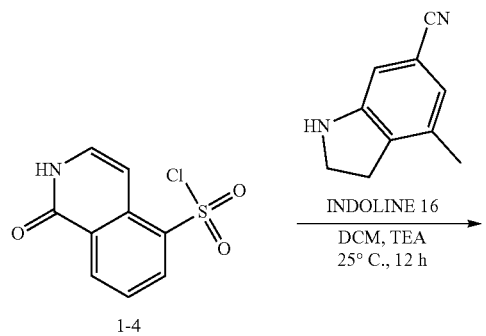

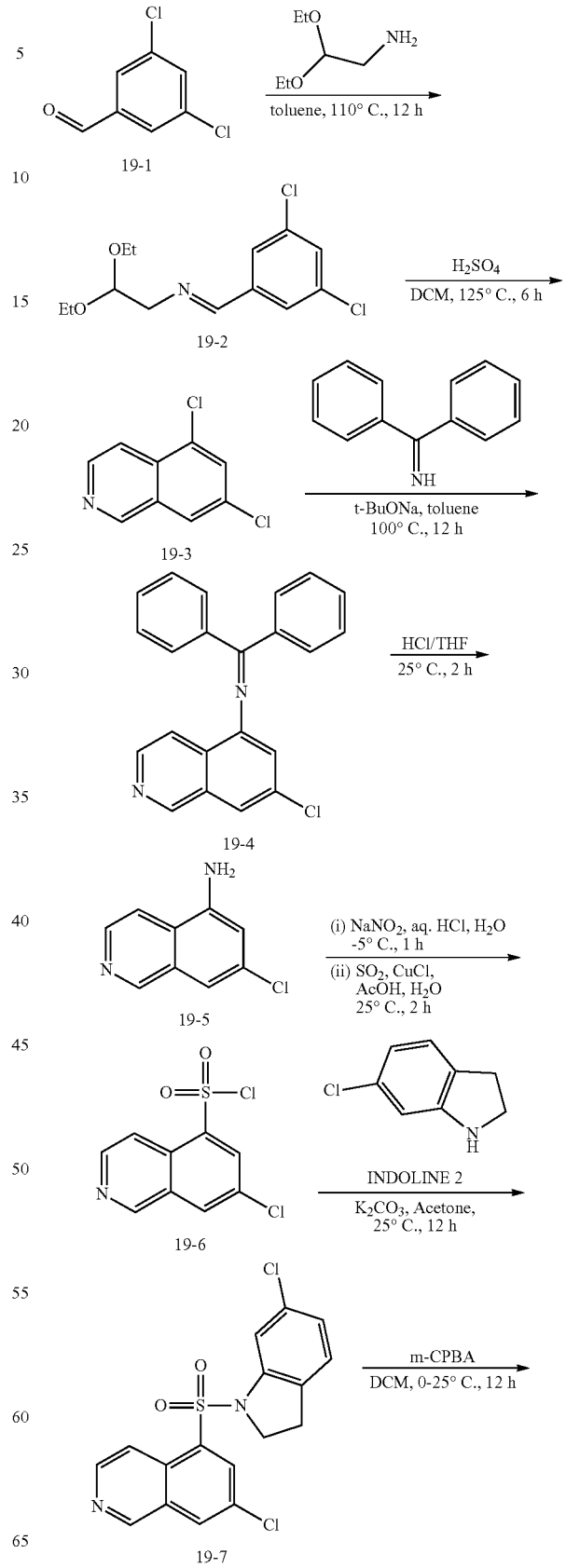

EXAMPLE 18: To a solution of 1-oxo-2H-isoquinoline-5-sulfonyl chloride (100 mg, 410.4 μmol) in DCM (5 mL) was added TEA (65.9 μL, 474.0 μmol) and 4-methylindoline-6-carbonitrile INDOLINE 16 (50 mg, 316.0 μmol). The reaction mixture was stirred at 25° C. for 12 h under an $N_2$ atmosphere. The reaction mixture was diluted with $H_2O$ (20 mL) and was extracted with DCM (100 mL×2). The combined organic layers were washed with saturated brine (10 mL), dried over anhydrous $Na_2SO_4$, filtered and concentrated under reduced pressure to give a residue. The residue was purified by column chromatography ($SiO_2$, petroleum ether:ethyl acetate=1:0 to 0:1). The residue was purified by column chromatography ($SiO_2$, petroleum ether:ethyl acetate=1:0 to 4:5). EXAMPLE 18, 1-[(1-hydroxy-5-isoquinolyl)sulfonyl]-4-methyl-indoline-6-carbonitrile (8 mg, 19.9 μmol, 6.30% yield), was obtained as a white solid. LC-MS: [M+1] 365.08.

$^1$H NMR (400 MHz, MeOD): δ 8.61 (d, J=8 Hz, 1H), 8.38 (d, J=8 Hz, 1H), 7.64 (t, J=8 Hz, 1H), 7.56 (s, 1H), 7.37 (d, J=7.6 Hz, 1H), 7.28 (d, J=8 Hz, 1H), 7.21 (s, 1H), 4.07 (t, J=8.4 Hz, 2H), 2.96 (t, J=8.4 Hz, 2H), 2.20 (s, 3H). One proton was exchanged.

Example 19

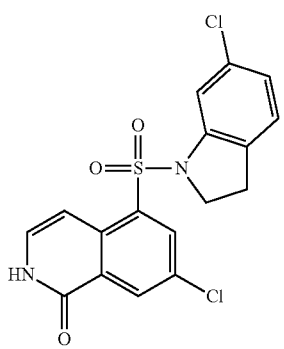 [SMILES: O=c1[nH]ccc2c(S(=O)(=O)N3CCc4ccc(Cl)cc43)cc(Cl)cc12]

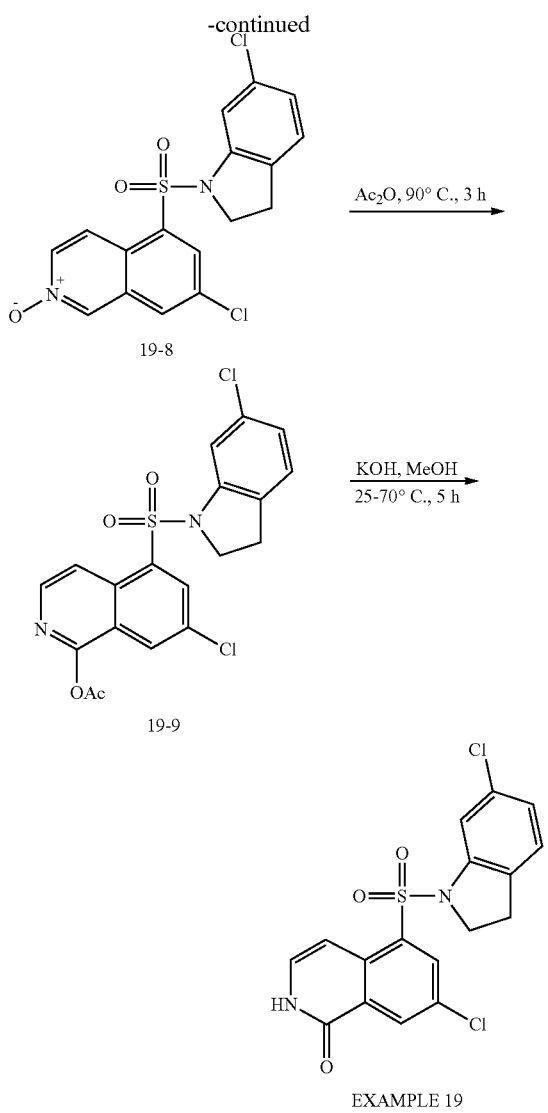

EXAMPLE 19

Compound 19-2: A mixture of 3,5-dichlorobenzaldehyde (25 g, 142.8 mmol), 2,2-diethoxyethanamine (83.08 mL, 571.3 mmol) in toluene (200 mL) was degassed and purged with $N_2$ 3 times, and then the mixture was stirred at 110° C. for 12 h under an $N_2$ atmosphere. The reaction mixture was diluted with $H_2O$ (500 mL) and extracted with EtOAc (900 mL×2). The combined organic layers were washed with saturated brine (200 mL), dried over anhydrous $Na_2SO_4$, filtered and concentrated under reduced pressure to give a residue. The crude product, compound 19-2, (E)-1-(3,5-dichlorophenyl)-N-(2,2-diethoxyethyl)methanimine (35 g, crude) was obtained as a yellow solid. The crude product was used in the next step without further purification.

Compound 19-3: To a solution of $H_2SO_4$ (500 mL) was added drop wise (E)-1-(3,5-dichlorophenyl)-N-(2,2-diethoxyethyl) methanimine (30 g, 103.3 mmol) in DCM (100 mL) at 125° C. The resulting mixture was stirred at 125° C. for 6 h under an $N_2$ atmosphere. The reaction mixture was quenched by addition of ice water (200 mL) at 0° C. and then aq.NaOH (200 mL) was added to the mixture to adjust pH 8. It was extracted with EtOAc (1000 mL×2). The combined organic layers were washed with saturated brine (200 mL), dried over anhydrous $Na_2SO_4$, filtered and concentrated under reduced pressure to give a residue. The residue was purified by column chromatography ($SiO_2$, petroleum ether:ethyl acetate=20:1 to 5:1). Compound 19-3, 5,7-dichloroisoquinoline (8 g, 40.3 mmol, 39.0% yield), was obtained as a yellow solid.

Compound 19-4: A mixture of 5,7-dichloroisoquinoline (100 mg, 504.9 µmol), diphenylmethanimine (137.2 mg, 757.3 µmol), (5-diphenylphosphanyl-9,9-dimethyl-xanthen-4-yl)-diphenyl-phosphane, methanesulfonate, [2-[2-(methylamino)phenyl]phenyl] palladium (485.9 mg, 504.9 µmol), t-BuONa (2 M, 1.26 mL) in toluene (10 mL) was degassed and purged with $N_2$ 3 times, and then the mixture was stirred at 100° C. for 12 h under an $N_2$ atmosphere. The reaction mixture was diluted with $H_2O$ (20 mL) and extracted with DCM (80 mL×2). The combined organic layers were washed with saturated brine (10 mL), dried over anhydrous $Na_2SO_4$, filtered and concentrated under reduced pressure to give a residue. The residue was purified by column chromatography ($SiO_2$, petroleum ether:ethyl acetate=20:1 to 1:1). Compound 19-4, N-(7-chloro-5-isoquinolyl)-1,1-diphenyl-methanimine (40 mg, 116.6 µmol, 11.5% yield), was obtained as a yellow solid.

Compound 19-5: To a solution of N-(7-chloro-5-isoquinolyl)-1,1-diphenyl-methanimine (0.3 g, 875.0 µmol) in THF (10 mL) was added HCl (3 M, 525.0 µL). The mixture was stirred at 25° C. for 2 h under an $N_2$ atmosphere. The reaction mixture was quenched by addition of ice water (10 mL) at 0° C., and then aq. NaOH (10 mL) was added to the mixture to adjust to pH 8. The reaction mixture was diluted with $H_2O$ (10 mL) and extracted with DCM (50 mL×2). The combined organic layers were washed with saturated brine (10 mL), dried over anhydrous $Na_2SO_4$, filtered and concentrated under reduced pressure to give a residue. The residue was purified by column chromatography ($SiO_2$, petroleum ether:ethyl acetate=5:1 to 1:1). Compound 19-5, 7-chloroisoquinolin-5-amine (0.1 g, 559.8 µmol, 63.9% yield), was obtained as a yellow solid.

Compound 19-6: To a solution of 7-chloroisoquinolin-5-amine (0.1 g, 559 µmol) in HCl (5 mL) was added $NaNO_2$ (38.6 mg, 559.8 µmol) and $H_2O$ (1 mL) at −5° C. The mixture was stirred at −5° C. for 1 h. Then it was transferred in one portion to a solution of AcOH (5 mL) with CuCl (13.8 mg, 139.9 µmol) in $H_2O$ (1 mL) that was saturated with bubbled $SO_2$. The mixture was stirred at 25° C. for 2 h. The reaction mixture was concentrated under reduced pressure to give a residue. The residue was taken up with water (20 mL) and DCM and extracted with DCM (80 mL×2). The combined organic layers were washed with saturated brine (10 mL), dried over anhydrous $Na_2SO_4$, filtered and concentrated under reduced pressure to give a residue. The crude product, compound 19-6, 7-chloroisoquinoline-5-sulfonyl chloride (0.2 g, crude) was obtained as a yellow solid that was used in the next step without further purification.

Compound 19-7: To a solution of 7-chloroisoquinoline-5-sulfonyl chloride (0.2 g, 763.0 µmol) in acetone (10 mL) was added $K_2CO_3$ (158.1 mg, 1.14 mmol) and 6-chloroindoline INDOLINE 2 (128.9 mg, 839.3 µmol). The mixture was stirred at 25° C. for 12 h under an $N_2$ atmosphere. The reaction mixture diluted with $H_2O$ (20 mL) and extracted with DCM (80 mL×2). The combined organic layers were washed with saturated brine (10 mL), dried over anhydrous $Na_2SO_4$, filtered and concentrated under reduced pressure to give a residue. The residue was purified by column chromatography ($SiO_2$, petroleum ether:ethyl acetate=1:0 to 1:1). Compound 19-7, 7-chloro-5-(6-chloroindolin-1-yl)sulfonyl-isoquinoline (80 mg, 210.9 µmol, 27.6% yield), was obtained as a yellow solid.

Compound 19-8: A mixture of 7-chloro-5-(6-chloroindolin-1-yl)sulfonyl-isoquinoline (80 mg, 210.9 µmol), m-CPBA (65.7 mg, 316.4 µmol) in DCM (5 mL) was cooled to 0° C., and then the mixture was stirred at 25° C. for 12 h under an N₂ atmosphere. The reaction mixture was diluted with H₂O (15 mL) and extracted with DCM (25 mL×2). The combined organic layers were washed with saturated brine 10 mL, dried over anhydrous Na₂SO₄, filtered and concentrated under reduced pressure to give a residue. The residue was purified by column chromatography (SiO₂, petroleum ether:EtOAc=10:1 to DCM:MeOH=10:1). Compound 19-8, 7-chloro-5-(6-chloroindolin-1-yl)sulfonyl-2-oxido-isoquinolin-2-ium (50 mg, 126.5 µmol, 59.9% yield), was obtained as a yellow solid.

Compound 19-9: A mixture of 7-chloro-5-(6-chloroindolin-1-yl)sulfonyl-2-oxido-isoquinolin-2-ium (50 mg, 126.5 µmol) in Ac₂O (3 mL) was warmed to 90° C., and then the mixture was stirred at 90° C. for 3 h under an N₂ atmosphere. The reaction mixture was concentrated under reduced pressure to give a residue. The crude product [7-chloro-5-(6-chloroindolin-1-yl)sulfonyl-1-isoquinolyl] acetate (40 mg, crude) was obtained as a brown solid that was used in the next step without further purification.

EXAMPLE 19: A mixture of [7-chloro-5-(6-chloroindolin-1-yl)sulfonyl-1-isoquinolyl]acetate (40 mg, 91.4 µmol) and KOH (7.70 mg, 137.2 µmol) in MeOH (5 mL) was degassed and purged with N₂ 3 times, and then the mixture was stirred at 25° C. for 2 h under an N₂ atmosphere. Then the mixture was stirred at 70° C. for 3 h under an N₂ atmosphere. The reaction mixture was concentrated under reduced pressure to give a residue. The residue was purified by prep-HPLC (column: Xtimate C18 150 mm×25 mm×5 µm; mobile phase: [A, water (10 mM NH₄HCO₃)—B, ACN]; B %:50%-70%, 10 min). EXAMPLE 19, 7-chloro-5-(6-chloroindolin-1-yl)sulfonyl-2H-isoquinolin-1-one (18 mg, 45.0 µmol, 49.2% yield) was obtained as a yellow solid. LC-MS: [M+1] 393.99.

¹H NMR (400 MHz, DMSO-d₆): δ 8.43 (d, J=4.4 Hz, 1H), 8.21 (d, J=2.8 Hz, 1H), 7.38 (d, J=7.6 Hz, 1H), 7.33 (d, J=1.6 Hz, 1H), 7.23 (d, J=8 Hz, 1H), 7.08 (t, J=7.6 Hz, 2H), 4.05 (t, J=8.4 Hz, 2H), 2.95 (t, J=8.4 Hz, 2H). One proton was exchanged.

Example 20

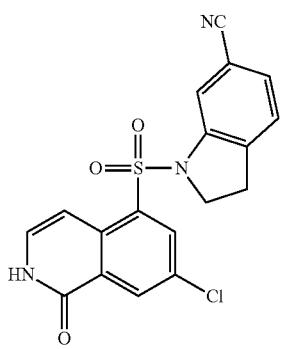 [SMILES: N#Cc1ccc2c(c1)N(S(=O)(=O)c1cc(Cl)cc3c(=O)[nH]ccc13)CC2]

Example 20

1-((7-Chloro-1-oxo-1,2-dihydroisoquinolin-5-yl)sulfonyl)indoline-6-carbonitrile

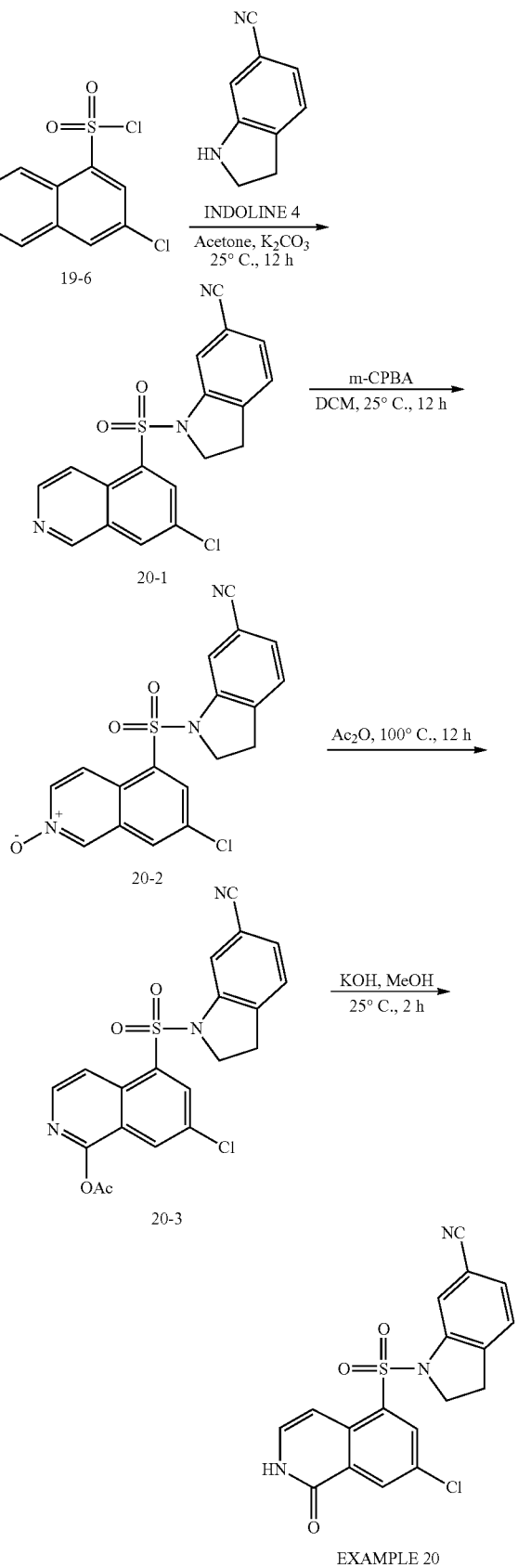

EXAMPLE 20

Compound 20-1: To a solution of 7-chloroisoquinoline-5-sulfonyl chloride (0.1 g, 381.5 µmol) in acetone (8 mL) was added K₂CO₃ (79.0 mg, 572.2 µmol) and indoline-6-carbonitrile INDOLINE 4 (60.5 mg, 419.6 µmol). The mixture was stirred at 25° C. for 12 h under an N₂ atmosphere. The reaction mixture was diluted with H₂O (20 mL) and extracted with DCM (80 mL×2). The combined organic layers were washed with saturated brine (10 mL), dried over anhydrous Na₂SO₄, filtered and concentrated under reduced pressure to give a residue. The residue was purified by column chromatography (SiO₂, petroleum ether:ethyl acetate=10:1 to 0:1). Compound 20-1, 1-[(7-chloro-5-isoquinolyl)sulfonyl]indoline-6-carbonitrile (30 mg, 81.1 µmol, 21.2% yield), was obtained as a yellow solid.

Compound 20-2: A mixture of 1-[(7-chloro-5-isoquinolyl)sulfonyl]indoline-6-carbonitrile (30 mg, 81.1 µmol), m-CPBA (26.2 mg, 121.6 µmol) in DCM (5 mL) was degassed and purged with N₂ 3 times, and then the mixture was stirred at 25° C. for 12 h under an N₂ atmosphere. The reaction mixture was diluted with H₂O (15 mL) and extracted with DCM (50 mL×2). The combined organic layers were washed with saturated brine (10 mL), dried over anhydrous Na₂SO₄, filtered and concentrated under reduced pressure to give a residue. The residue was purified by column chromatography (SiO₂, petroleum ether:ethyl acetate=5:1 to DCM:MeOH=10:1). Compound 20-2, 1-(7-chloro-2-oxido-isoquinolin-2-ium-5-yl)sulfonylindoline-6-carbonitrile (30 mg), was obtained as a yellow solid.

Compound 20-3: A mixture of 1-(7-chloro-2-oxido-isoquinolin-2-ium-5-yl)sulfonylindoline-6-carbonitrile (30 mg, 77.7 µmol) in Ac₂O (3 mL) was degassed and purged with N₂ 3 times, and then the mixture was stirred at 100° C. for 12 h under an N₂ atmosphere. The reaction mixture was concentrated under reduced pressure to give a residue. The crude product Compound 20-3, [7-chloro-5-(6-cyanoindolin-1-yl)sulfonyl-1-isoquinolyl] acetate (20 mg, crude), was obtained as a yellow oil that was used in the next step without further purification.

EXAMPLE 20: A mixture of [7-chloro-5-(6-cyanoindolin-1-yl)sulfonyl-1-isoquinolyl]acetate (20 mg, 46.7 µmol) and KOH (5.25 mg, 93.4 µmol) in MeOH (5 mL) was degassed and purged with N₂ 3 times, and then the mixture was stirred at 25° C. for 2 h under an N₂ atmosphere. The reaction mixture was diluted with H₂O (10 mL) and extracted with DCM (50 mL×2). The combined organic layers were washed with saturated brine (10 mL), dried over anhydrous Na₂SO₄, filtered and concentrated under reduced pressure to give a residue. The residue was purified by prep-HPLC (column: HUAPU C8 Extreme BDS 150 mm×30 mm×5 um; mobile phase: [A, water (10 mM NH₄HCO₃)—B, ACN]; B %: 45%-55%, 10 min). EXAMPLE 20, 1-[(7-chloro-1-oxo-2H-isoquinolin-5-yl)sulfonyl]indoline-6-carbonitrile (2 mg, 4.7 µmol, 10.2% yield), was obtained as a white solid. LC-MS: [M+1] 385.03.

¹H NMR (400 MHz, DMSO-d₆): δ 8.44 (d, J=2.4 Hz, 1H), 8.32 (d, J=2 Hz, 1H), 7.68 (s, 1H), 7.52 (d, J=1.2 Hz, 1H), 7.45~7.36 (m, 2H), 7.04 (d, J=8.8 Hz, 1H), 4.07 (t, J=8.4 Hz, 2H), 3.07 (t, J=8.4 Hz, 2H). One proton was exchanged.

Example 21

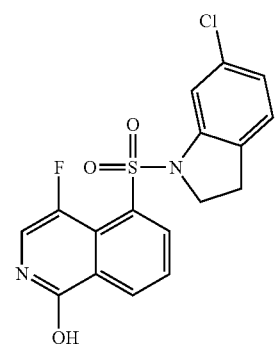 [SMILES: O=S(=O)(c1cccc2c(O)ncc(F)c12)N1CCc2ccc(Cl)cc21]

5-((6-Chloroindolin-1-yl)sulfonyl)-4-fluoroisoquinolin-1-ol

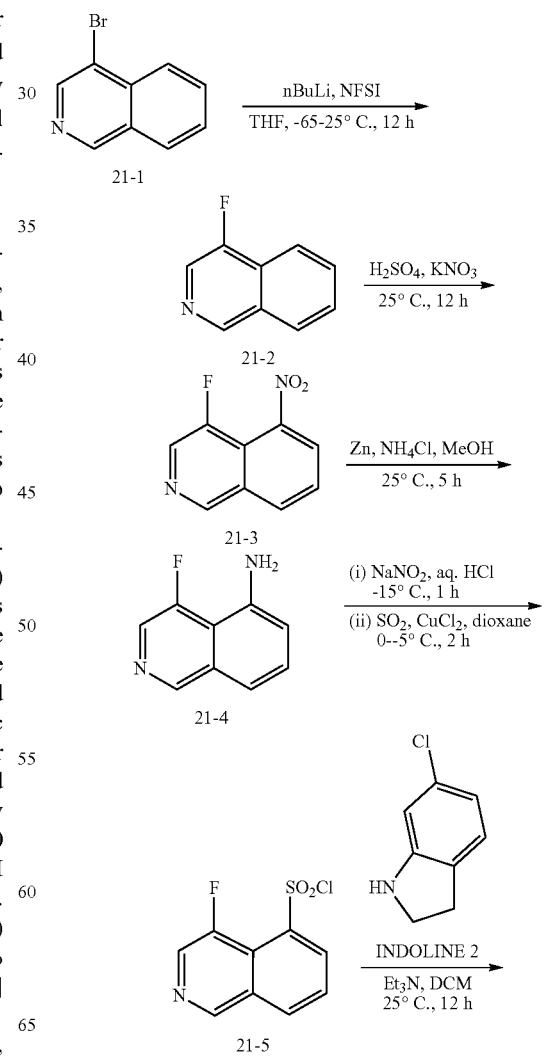

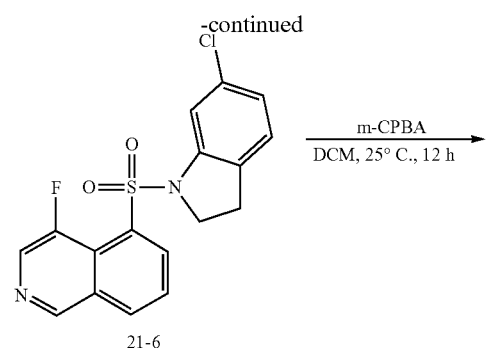

21-6

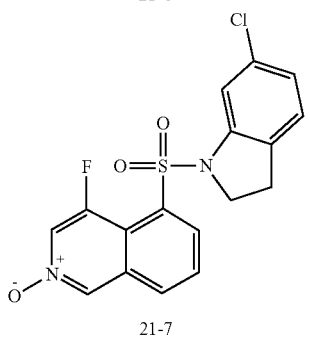

21-7

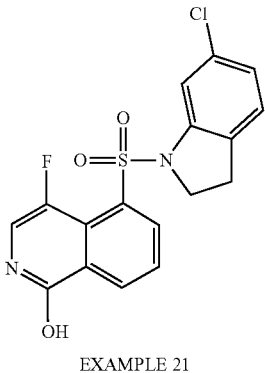

EXAMPLE 21

Compound 21-2: To a solution of n-BuLi (2.5 M, 201.8 mL) in THF (100 mL) was added a solution of 4-bromoisoquinoline (30 g, 144.1 mmol) in THF (100 mL) at −65° C. The mixture was stirred at −65° C. for 30 min. A solution of N-(benzenesulfonyl)-N-fluoro-benzenesulfonamide (100.0 g, 317.2 mmol) in THF (100 mL) was added at −65° C. The mixture was stirred at −65° C. for 1 h. Then the mixture was stirred at 25° C. for 10.5 h under an $N_2$ atmosphere. The reaction mixture was diluted with $H_2O$ (500 mL) and extracted with EtOAc (1500 mL×2). The combined organic layers were washed with saturated brine (100 mL), dried over anhydrous $Na_2SO_4$, filtered and concentrated under reduced pressure to give a residue. The crude product, compound 21-2, 4-fluoroisoquinoline (30 g, crude), was obtained as brown oil. The crude product was used in the next step without further purification.

Compound 21-3: To a solution of 4-fluoroisoquinoline (8 g, 54.3 mmol) in $H_2SO_4$ (50 mL) was added $KNO_3$ (6.05 g, 59.8 mmol). The mixture was stirred at 25° C. for 12 h under an $N_2$ atmosphere. The reaction mixture was quenched by addition of ice water (100 mL) at −15° C., and then aq.NaOH (50 mL) was added to the mixture to adjust to pH 8. It was filtered and the filtrate was concentrated under reduced pressure to give a residue. The residue was purified by column chromatography (SiO$_2$, petroleum ether:ethyl acetate=10:1 to 1:1). Compound 21-3, 4-fluoro-5-nitro-isoquinoline (5 g, 26.0 mmol, 47.8% yield), was obtained as a yellow solid.

Compound 21-4: A mixture of 4-fluoro-5-nitro-isoquinoline (5 g, 26.0 mmol), $NH_4Cl$ (11.1 g, 208.1 mmol), Zn (13.6 g, 208.1 mmol) in THF (20 mL) and $H_2O$ (10 mL) was degassed and purged with $N_2$ 3 times, and then the mixture was stirred at 25° C. for 5 h under an $N_2$ atmosphere. The reaction mixture was filtered and the filtrate was concentrated. The residue was purified by column chromatography (SiO$_2$, petroleum ether:ethyl acetate=10:1 to 1:1). Compound 21-4, 4-fluoroisoquinolin-5-amine (3 g, 18.5 mmol, 71.1% yield), was obtained as a yellow solid.

Compound 21-5: To a solution of 4-fluoroisoquinolin-5-amine (3 g, 18.5 mmol) in HCl (10 mL) was added NaNO$_3$ (1.57 g, 18.5 mmol) and $H_2O$ (2 mL) at −15° C. The mixture was stirred at −15° C. for 1 h under an $N_2$ atmosphere. Then it was transferred to a solution of AcOH (10 mL) with CuCl (457.8 mg, 4.62 mmol) and $H_2O$ (2 mL) that was saturated by bubbled SO$_2$. The mixture was stirred at −5° C. for 2 h. The reaction mixture was concentrated under reduced pressure to give a residue. The crude product Compound 21-5, 4-fluoroisoquinoline-5-sulfonyl chloride (1.1 g, crude), was obtained as a yellow solid and it was used in the next step without further purification.

Compound 21-6: A mixture of 4-fluoroisoquinoline-5-sulfonyl chloride (0.5 g, 2.04 mmol), 6-chloroindoline INDOLINE 2 (250.1 mg, 1.63 mmol), TEA (424.9 µL, 3.05 mmol) in DCM (10 mL) was degassed and purged with $N_2$ 3 times, and then the mixture was stirred at 25° C. for 12 h under an $N_2$ atmosphere. The reaction mixture was diluted with $H_2O$ (30 mL) and it was extracted with DCM (100 mL×2). The combined organic layers were washed with saturated brine (20 mL), dried over anhydrous $Na_2SO_4$, filtered and concentrated under reduced pressure to give a residue. The residue was purified by column chromatography (SiO$_2$, petroleum ether:ethyl acetate=10:1 to 1:1). Compound 21-6, 5-(6-chloroindolin-1-yl)sulfonyl-4-fluoro-isoquinoline (0.2 g, 551.2 µmol), was obtained as a yellow solid.

Compound 21-7: A mixture of 5-(6-chloroindolin-1-yl)sulfonyl-4-fluoro-isoquinoline (0.2 g, 551 µmol), m-CPBA (142.6 mg, 826.9 µmol) in DCM (10 mL) was degassed and purged with $N_2$ 3 times, and then the mixture was stirred at 25° C. for 12 h under an $N_2$ atmosphere. The reaction mixture was diluted with $H_2O$ (20 mL) and extracted with DCM (100 mL×2). The combined organic layers were washed with saturated brine (10 mL), dried over anhydrous $Na_2SO_4$, filtered and concentrated under reduced pressure to give a residue. The residue was purified by column chromatography (SiO$_2$, petroleumether:ethyl acetate=5:1 to DCM:MeOH=10:1). Compound 21-7, 5-(6-chloroindolin-1-yl)sulfonyl-4-fluoro-2-oxido-isoquinolin-2-ium (70 mg, 184 µmol, 33.5% yield), was obtained as a white solid.

EXAMPLE 21: A mixture of 5-(6-chloroindolin-1-yl)sulfonyl-4-fluoro-2-oxido-isoquinolin-2-ium (70 mg, 184.7 µmol) in Ac$_2$O (10 mL) was degassed and purged with $N_2$ 3 times, and then the mixture was stirred at 110° C. for 8 h under an $N_2$ atmosphere. The reaction mixture was diluted with $H_2O$ (20 mL) and extracted with DCM (80 mL×2). The combined organic layers were washed with saturated brine (10 mL), dried over anhydrous $Na_2SO_4$, filtered and concentrated under reduced pressure to give a residue. The residue was purified by column chromatography (SiO$_2$, petroleum ether:ethyl acetate=10:1 to 0:1). The residue was purified by prep-HPLC (column: HUAPU C8 Extreme BDS 150 mm×30 mm×5 µm; mobile phase: [A, water (10 mM NH₄HCO₃)—B, ACN]; B %:35%-55%, 10 min). EXAMPLE 21, 5-(6-chloroindolin-1-yl)sulfonyl-4-fluoro-isoquinolin-1-ol (5 mg, 12.2 μmol, 6.61% yield) was obtained as a white solid. LC-MS: [M+1] 378.81.

¹H NMR (400 MHz, MeOD): δ 9.10 (s, 1H), 8.74 (d, J=7.6 Hz, 1H), 8.23 (d, J=7.6 Hz, 1H), 7.97 (d, J=6.8 Hz, 1H), 7.81 (t, J=7.6 Hz, 1H), 7.35 (d, J=8 Hz, 1H), 7.12~7.15 (m, 1H), 4.16 (t, J=8.8 Hz, 2H), 3.23 (t, J=8.4 Hz, 2H). One proton was exchanged.

Example 22

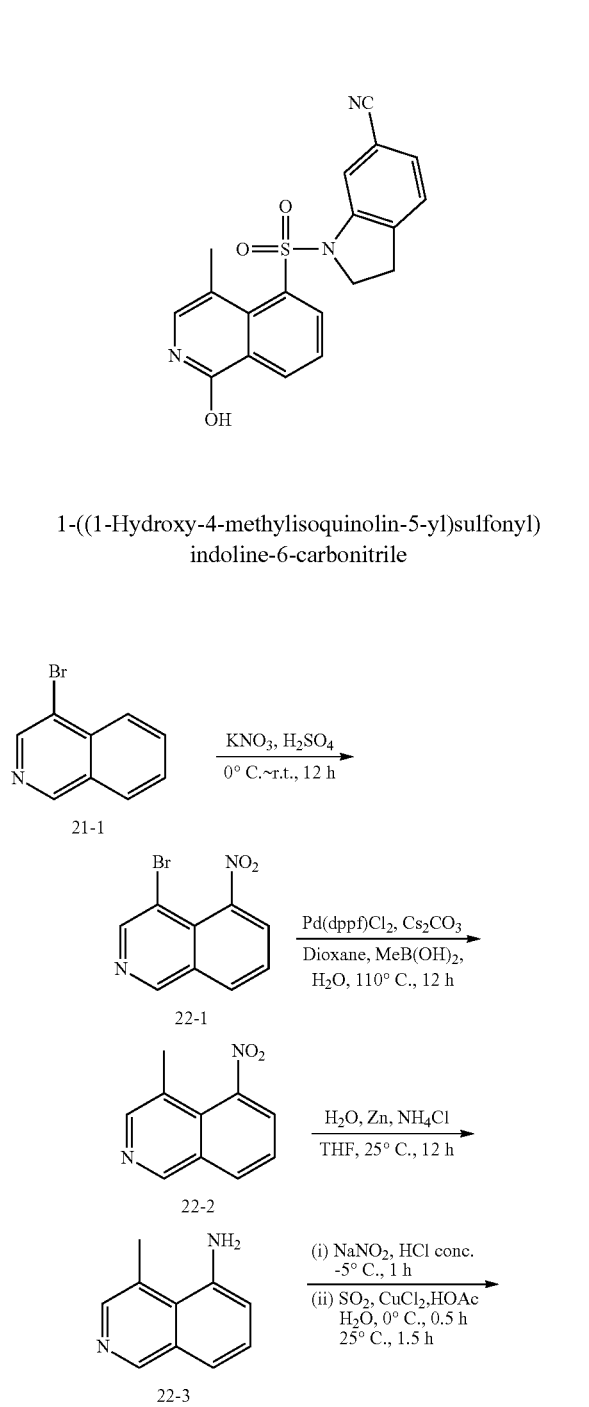

1-((1-Hydroxy-4-methylisoquinolin-5-yl)sulfonyl) indoline-6-carbonitrile

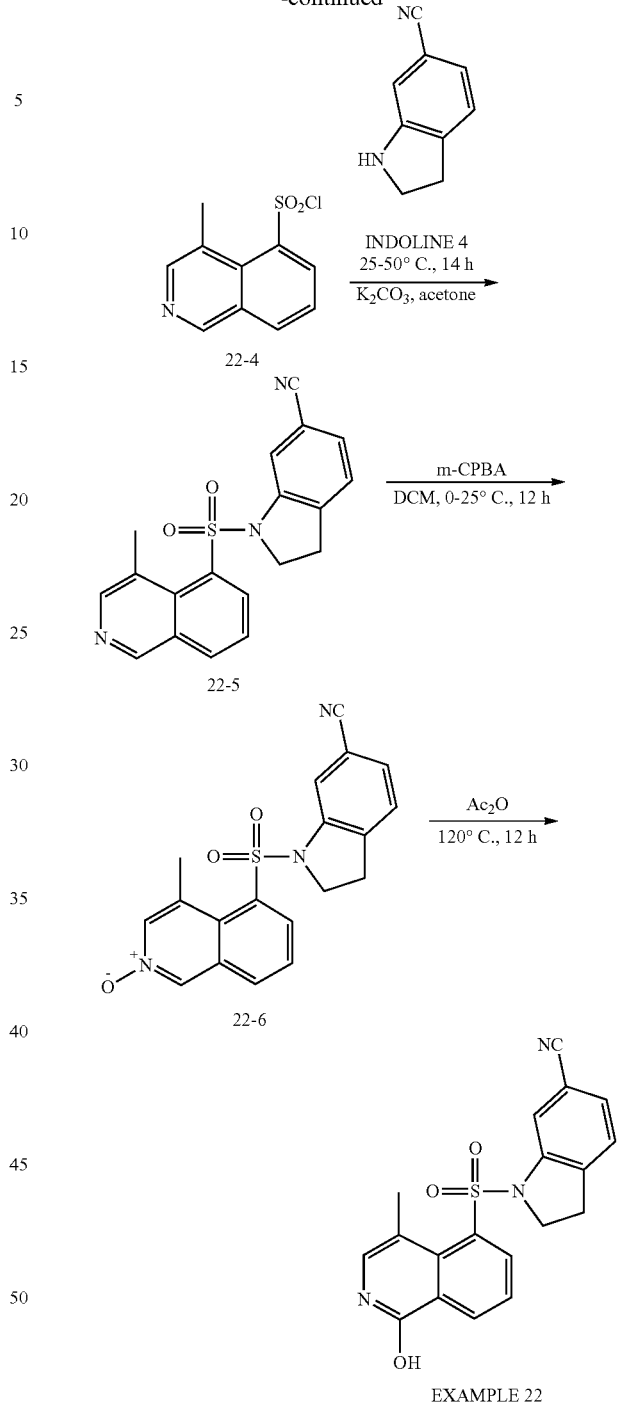

Compound 22-1: To a mixture of KNO₃ (21.3 g, 211.4 mmol) in H₂SO₄ (600 mL) was added 4-bromoisoquinoline (40 g, 192.2 mmol) at 0° C. and then the mixture was stirred at 25° C. for 12 h under an N₂ atmosphere. The reaction mixture was quenched by the addition of ice water (3000 mL) and then NH₃.H₂O was added to the mixture to adjust to pH 8. The mixture was filtered and concentrated under reduced pressure to give a residue. The residue was washed by MeOH (500 mL) and then filtered. The solid was dissolved with EtOAc (500 mL) and H₂O (1000 mL). The organic layer was concentrated under reduced pressure to give a residue. Compound 22-1, 4-bromo-5-nitro-isoquinoline (75 g, 296.3 mmol, 77.0% yield), was obtained as a yellow solid.

Compound 22-2: To a mixture of 4-bromo-5-nitro-isoquinoline (55 g, 217.3 mmol) in dioxane (500 mL) and $H_2O$ (50 mL) was added methylboronic acid (26.02 g, 434.6 mmol), $Cs_2CO_3$ (141.6 g, 434.6 mmol) and $Pd(dppf)Cl_2$ (15.90 g, 21.73 mmol) in one portion. The mixture was heated to 110° C. and stirred for 12 h. The reaction mixture was filtered. The filtrate was diluted with $H_2O$ (1.2 L) and extracted with EtOAc (800 mL×2). The combined organic layers were washed with brine (1.2 L), dried over $Na_2SO_4$, filtered and concentrated under reduced pressure to give a residue. The residue was purified by column chromatography ($SiO_2$, petroleum ether:ethyl acetate=1:0 to 3:1). Compound 22-2, 4-methyl-5-nitro-isoquinoline (36 g, 191.3 mmol, 88.0% yield), was obtained as a yellow solid.

Compound 22-3: To a solution of 4-methyl-5-nitro-isoquinoline (33 g, 175.3 mmol) in THF (500 mL) and $H_2O$ (250 mL) was added Zn (91.7 g, 1.40 mol) and $NH_4Cl$ (75.0 g, 1.40 mol). The mixture was stirred at 25° C. for 12 h. The reaction mixture was filtered and concentrated under reduced pressure to give a residue. The residue was purified by column chromatography ($SiO_2$, petroleum ether:ethyl acetate=1:0 to 0:1). Compound 22-3, 4-methylisoquinolin-5-amine (20 g, 113.8 mmol, 64.8% yield), was obtained as a yellow solid.

Compound 22-4: Solution 1: To a mixture of 4-methyl-isoquinolin-5-amine (3 g, 18.9 mmol) in HCl (30 mL) was added $NaNO_2$ (1.31 g, 18.9 mmol) and $H_2O$ (6 mL) in one portion at −5° C. under $N_2$. The mixture was stirred at −5° C. for 1 h. Solution 2: $SO_2$ was bubbled into a solution of CuCl (469.3 mg, 4.74 mmol) in HOAc (30 mL) and $H_2O$ (6 mL) at 0° C. for 30 minutes. The two solutions were mixed and stirred at 25° C. for 1.5 h. The reaction mixture was concentrated under reduced pressure to remove solvent. The residue was diluted with $H_2O$ (300 mL) and extracted with DCM (200 mL×3). The combined organic layers were washed with brine (300 mL), dried over $Na_2SO_4$, filtered and concentrated under reduced pressure to give a residue. Compound 22-4, 4-methylisoquinoline-5-sulfonyl chloride (2 g, crude), was obtained as a yellow solid and was used directly without purification.

Compound 22-5: To a solution of 4-methylisoquinoline-5-sulfonyl chloride (2 g, 8.27 mmol) in acetone (30 mL) was added $K_2CO_3$ (3.43 g, 24.8 mmol) and indoline-6-carbonitrile INDOLINE 4 (1.19 g, 8.27 mmol). The mixture was stirred at 25° C. for 12 h. The mixture was heated to 50° C. and stirred for 2 hours. The reaction mixture was diluted with $H_2O$ (200 mL) and extracted with DCM (200 mL×2). The combined organic layers were dried over $Na_2SO_4$, filtered and concentrated under reduced pressure to give a residue. The residue was purified by column chromatography ($SiO_2$, petroleum ether:ethyl acetate=1:0 to 0:1). Compound 22-5, 1-[(4-methyl-5-isoquinolyl)sulfonyl]indoline-6-carbonitrile (1.1 g, 2.52 mmol, 30.4% yield), was obtained as a yellow solid.

Compound 22-6: To a solution of 1-[(4-methyl-5-isoquinolyl)sulfonyl]indoline-6-carbonitrile (1.1 g, 3.15 mmol) in DCM (30 mL) was added m-CPBA (1.44 g, 6.93 mmol) at 0° C. The mixture was warmed to 25° C. and stirred for 12 h. The reaction mixture was purified directly by column chromatography ($SiO_2$, petroleum ether:ethyl acetate=1:0, ethyl acetate: EtOH=1:1). Compound 22-6, 1-(4-methyl-2-oxido-isoquinolin-2-ium-5-yl)sulfonylindoline-6-carbonitrile (1 g, 2.54 mmol, 80.7% yield), was obtained as a yellow solid.

EXAMPLE 22: A mixture of 1-(4-methyl-2-oxido-isoquinolin-2-ium-5-yl)sulfonylindoline-6-carbonitrile (1 g, 2.74 mmol) in $Ac_2O$ (20 mL) was heated to 120° C. and stirred for 12 h. The reaction mixture was concentrated under reduced pressure to remove solvent. The residue was dissolved in DMF (20 mL) and filtered. The filtrate was purified by prep-HPLC (column: Waters Xbridge Prep OBD C18 150 mm×40 mm×10 rpm; mobile phase: [A, water (10 mM $NH_4HCO_3$)—B, ACN];B %: 20%-50%, 11 min) and concentrated. The product was added to EtOH (2 mL) and filtered to provide 1-[(1-hydroxy-4-methyl-5-isoquinolyl)sulfonyl]indoline-6-carbonitrile (19 mg) as a light yellow solid. LC-MS: [M+1]365.08.

$^1$H NMR (400 MHz, DMSO-$d_6$): δ 11.71 (br, 1H), 8.59 (d, J=6.4 Hz, 1H), 7.89 (d, J=6.4 Hz, 1H), 7.59~7.51 (m, 3H), 7.25 (s, 2H), 4.22 (t, J=8.8 Hz, 2H), 3.4 (t, J=8.4 Hz, 2H), 2.61 (s, 3H).

Example 23

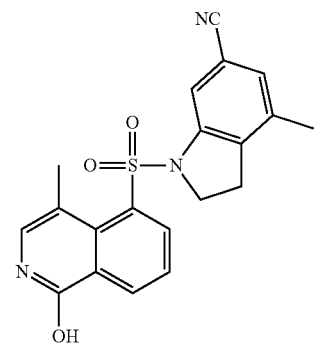 [SMILES: Cc1cc(C#N)cc2c1CCN2S(=O)(=O)c1cccc2c(O)ncc(C)c12]

1-((1-Hydroxy-4-methylisoquinolin-5-yl)sulfonyl)-4-methylindoline-6-carbonitrile

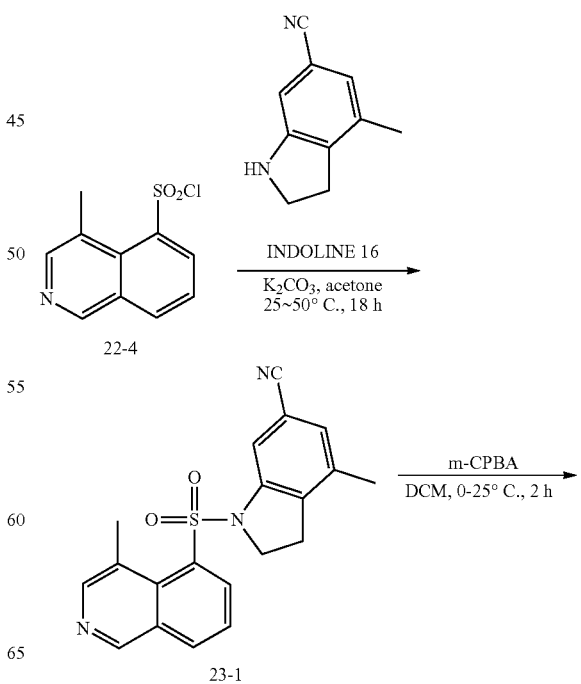

7.39 (s, 1H), 7.26~7.25 (m, 1H), 7.09 (s, 1H), 4.22 (t, J=8 Hz, 2H) 2.61 (s, 6H) (2H may be overlapped with the water peak).

Example 24

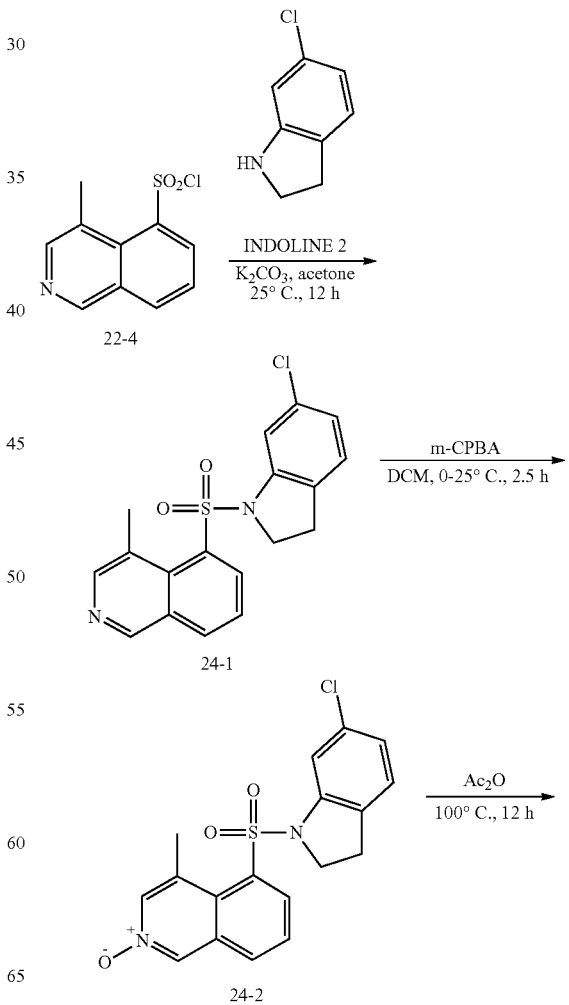

5-((6-Chloroindolin-1-yl)sulfonyl)-4-methylisoquinolin-1-ol

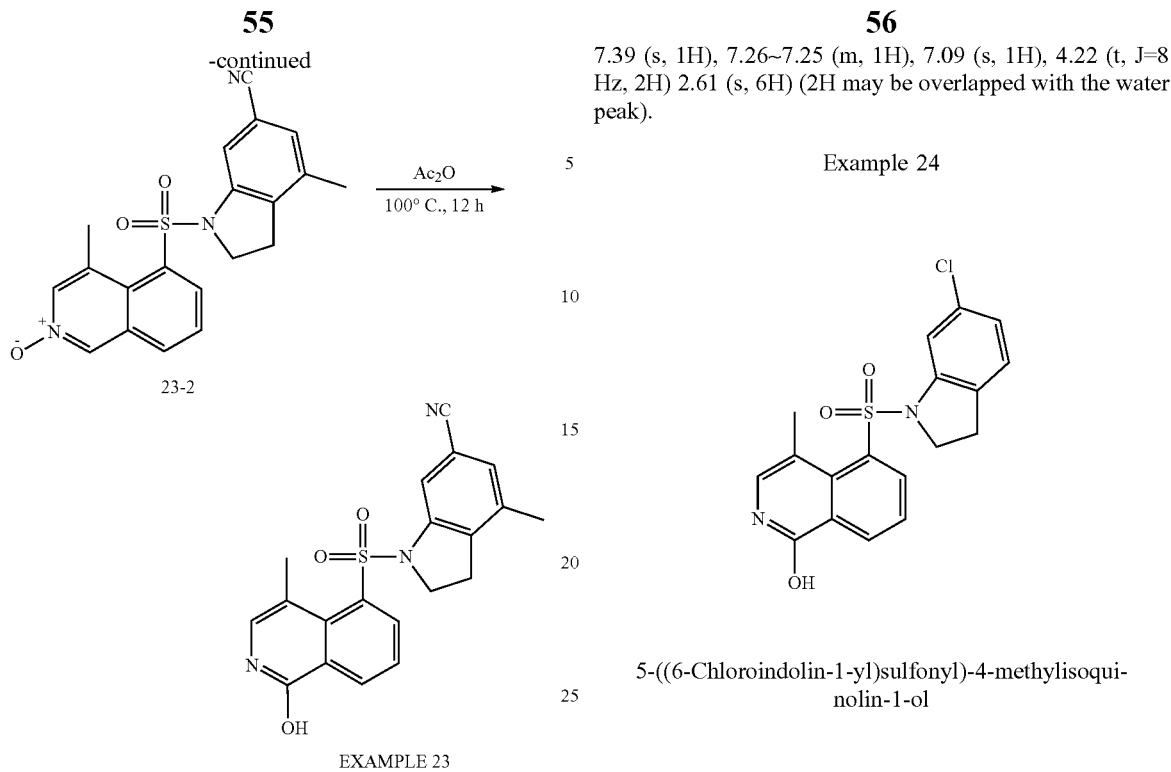

EXAMPLE 23

Compound 23-1: To a solution of 4-methylisoquinoline-5-sulfonyl chloride (100 mg, 413.7 μmol) in acetone (5 mL) was added K$_2$CO$_3$ (171.5 mg, 1.24 mmol) and 4-methylindoline-6-carbonitrile INDOLINE 16 (52.36 mg, 331.0 μmol). The mixture was stirred at 25° C. for 12 h. The mixture was heated to 50° C. and stirred for 6 hours. The reaction mixture was diluted with H$_2$O (100 mL) and extracted with DCM (100 mL×2). The combined organic layers were dried over Na$_2$SO$_4$, filtered and concentrated under reduced pressure to give a residue. The residue was purified by column chromatography (SiO$_2$, petroleum ether: ethyl acetate=1:0 to 0:1). Compound 23-1, 4-methyl-1-[(4-methyl-5-isoquinolyl)sulfonyl]indoline-6-carbonitrile (50 mg, crude), was obtained as a yellow solid.

Compound 23-2: To a solution of 4-methyl-1-[(4-methyl-5-isoquinolyl)sulfonyl]indoline-6-carbonitrile (50 mg, 137 μmol) in DCM (10 mL) was added m-CPBA (62.9 mg, 302.7 μmol) at 0° C. The mixture was heated to 25° C. and stirred for 2 h. The residue was purified by column chromatography (SiO$_2$, petroleum ether:ethyl acetate=1:0, ethyl acetate: MeOH=5:1). Compound 23-2, 4-methyl-1-(4-methyl-2-oxido-isoquinolin-2-ium-5-yl)sulfonyl-indoline-6-carbonitrile (40 mg, crude), was obtained as a yellow solid.

EXAMPLE 23: A mixture of 4-methyl-1-(4-methyl-2-oxido-isoquinolin-2-ium-5-yl)sulfonyl-indoline-6-carbonitrile (40 mg, 105.4 μmol) in Ac$_2$O (5 mL) was heated to 100° C. and stirred for 12 h. The reaction mixture was concentrated under reduced pressure to remove solvent. The residue was purified by prep-HPLC (column: Luna C18 100 mm×30 mm×5 m; mobile phase: [A, water (0.1% TFA)-B, ACN]; B %: 30%-55%, 12 min). EXAMPLE 23, 1-[(1-hydroxy-4-methyl-5-isoquinolyl) sulfonyl]-4-methyl-indoline-6-carbonitrile (1.6 mg, 3.97 mol, 3.76% yield) was obtained as a brown solid. LC-MS: [M+1] 379.10.

$^1$H NMR (400 MHz, DMSO-d$_6$): δ 11.71 (br, 1H), 8.59 (d, J=8 Hz, 1H), 7.88 (d, J=7.6 Hz, 1H), 7.53 (t, J=8 Hz, 1H),

57

-continued

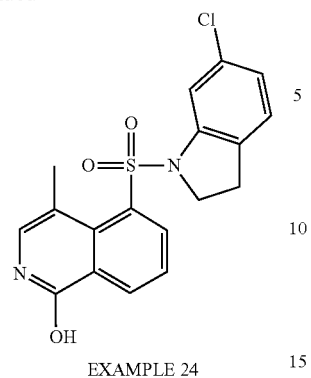

EXAMPLE 24

58

Example 25

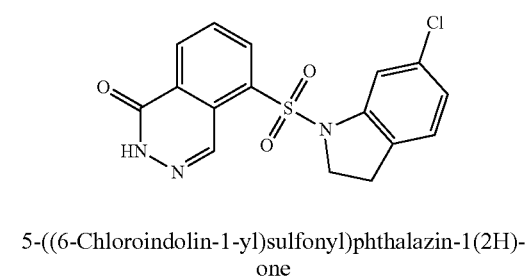

5-(((6-Chloroindolin-1-yl)sulfonyl)phthalazin-1(2H)-one

Compound 24-1: To a solution of 4-methylisoquinoline-5-sulfonyl chloride (500 mg, 2.07 mmol) in acetone (10 mL) was added $K_2CO_3$ (857.7 mg, 6.21 mmol) and 6-chloroindoline INDOLINE 2 (317.8 mg, 2.07 mmol). The mixture was stirred at 25° C. for 12 h. The reaction mixture was filtered and the filtrate was diluted with $H_2O$ (200 mL) and extracted with EtOAc (150 mL×2). The combined organic layers were dried over $Na_2SO_4$, filtered and concentrated under reduced pressure to give a residue. The residue was purified by column chromatography ($SiO_2$, petroleum ether: ethyl acetate=1:0 to 0:1). Compound 24-1, 5-(6-chloroindolin-1-yl)sulfonyl-4-methyl-isoquinoline (400 mg, 947.4 μmol, 45.80% yield), was obtained as a yellow solid.

Compound 24-2: To a solution of 5-(6-chloroindolin-1-yl)sulfonyl-4-methyl-isoquinoline (400 mg, 1.11 mmol) in DCM (10 mL) was added m-CPBA (579.3 mg, 2.79 mmol) at 0° C. The mixture was heated to 25° C. and stirred for 2.5 hours. The reaction mixture was purified directly by column chromatography ($SiO_2$, petroleum ether:ethyl acetate=1:0, ethyl acetate:MeOH=5:1). Compound 24-2, 5-(6-chloroindolin-1-yl)sulfonyl-4-methyl-2-oxido-isoquinolin-2-ium (300 mg, crude), was obtained as a yellow solid.

EXAMPLE 24: A mixture of 5-(6-chloroindolin-1-yl)sulfonyl-4-methyl-2-oxido-isoquinolin-2-ium (300 mg, 800.3 μmol) in $Ac_2O$ (10 mL) was heated to 100° C. and stirred for 12 h. The reaction mixture was concentrated under reduced pressure to remove solvent. The residue was purified by prep-HPLC (column: Waters Xbridge Prep OBD C18 150 mm×40 mm×10 μm; mobile phase: [A, water (10 mM $NH_4HCO_3$)—B, ACN]; B %: 30%-55%, 11 min). MeOH (2 mL) was added, the mixture was filtered and concentrated under reduced pressure to give the compound 24, 5-(6-chloroindolin-1-yl)sulfonyl-4-methyl-isoquinolin-1-ol (6 mg, 15.2 mol, 40.7% yield) as a yellow solid. LC-MS: [M+1] 374.05.

$^1$H NMR (400 MHz, DMSO-$d_6$): δ 11.70 (br, 1H), 8.59 (d, J=4.4 Hz, 1H), 7.86 (d, J=7.2 Hz, 1H), 7.54 (t, J=7.6 Hz, 1H), 7.37 (d, J=8 Hz, 1H), 7.25 (d, J=4.8 Hz 1H), 7.09 (d, J=8.8 Hz, 1H), 6.98 (s, 1H), 4.2 (t, J=8 Hz, 1H), 3.26 (m, 2H, overlapped with solvent peak), 2.61 (s, 3H). One proton was exchanged.

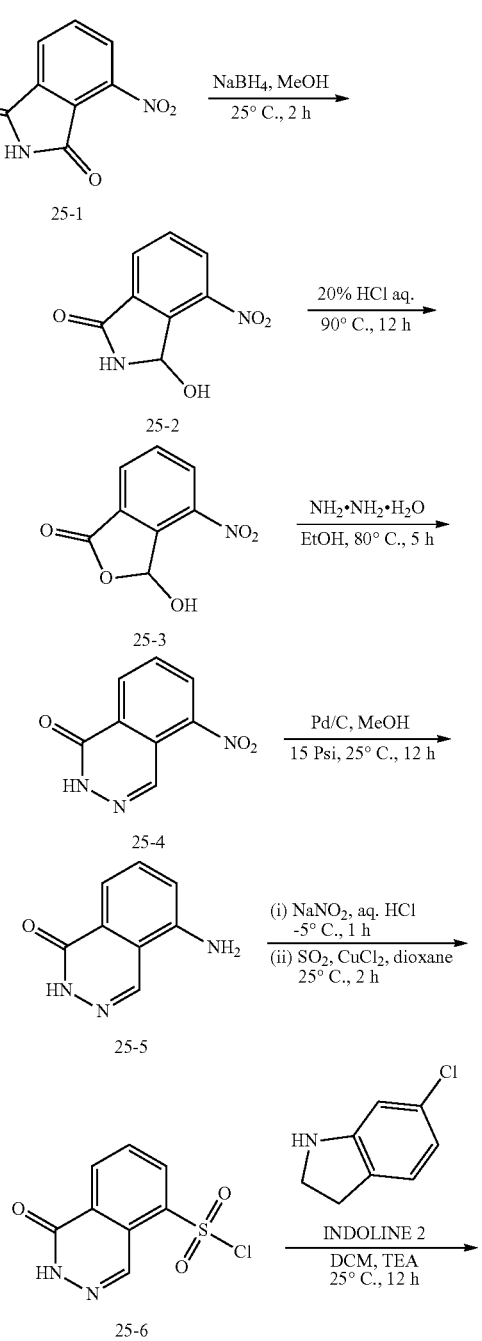

-continued

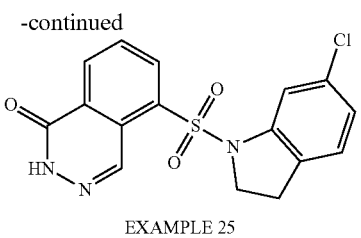

EXAMPLE 25

Compound 25-2: A mixture of 4-nitroisoindoline-1,3-dione (25 g, 130.1 mmol), NaBH$_4$ (11.13 g, 294.0 mmol) in MeOH (250 mL) was degassed and purged with N$_2$ 3 times. The mixture was stirred at 25° C. for 2 h under an N$_2$ atmosphere. The solution was acidified with 20% HCl (100 mL) and the reaction mixture was concentrated under reduced pressure to give a residue. The dried residue was treated with acetone. The residue was purified by column chromatography (SiO$_2$, petroleum ether:ethyl acetate=10:1 to 0:1). Compound 25-2, 3-hydroxy-4-nitro-isoindolin-1-one (15 g, 59% yield) was obtained as a yellow solid.

Compound 25-3: A mixture of 3-hydroxy-4-nitro-isoindolin-1-one (10 g, 51.5 mmol) in HCl (70 mL, 20% aq. solution) was degassed and purged with N$_2$ 3 times. The mixture was stirred at 90° C. for 12 h under an N$_2$ atmosphere. The reaction mixture was concentrated under reduced pressure to give a residue. The residue was purified by column chromatography (SiO$_2$, petroleum ether:ethyl acetate=10:1 to 1:1). Compound 25-3 3-hydroxy-4-nitro-3H-isobenzofuran-1-one (10 g, crude) was obtained as a yellow solid and was used without further purification.

Compound 25-4: A mixture of 3-hydroxy-4-nitro-3H-isobenzofuran-1-one (10 g, 51.2 mmol), N$_2$H$_4$·H$_2$O (9.05 g, 153.7 mmol) in EtOH (200 mL) was degassed and purged with N$_2$ 3 times. The mixture was stirred at 80° C. for 5 h under an N$_2$ atmosphere. The reaction mixture was concentrated under reduced pressure to give a residue. The residue was purified by column chromatography (SiO$_2$, petroleum ether:ethyl acetate to DCM:MeOH=10:1 to 10:1).

Compound 25-4, 5-nitro-2H-phthalazin-1-one (6 g, 31.3 mmol, 61.2% yield) was obtained as a yellow solid.

Compound 25-5: A mixture of 5-nitro-2H-phthalazin-1-one (6 g, 31.3 mmol), Pd/C (3 g, 10 wt %) in MeOH (100 mL) was degassed and purged with H$_2$ 3 times, and then the mixture was stirred at 25° C. for 12 h under H$_2$ atmosphere with a pressure of 15 psi. The reaction mixture was filtered and the filtrate was concentrated. The residue was purified by column chromatography (SiO$_2$, petroleum ether:ethyl acetate to DCM:MeOH=10:1 to 10:1). Compound 25-5, 5-amino-2H-phthalazin-1-one (3 g, 18.6 mmol, 59.3% yield) was obtained as a yellow solid.

Compound 25-6: To a solution of 5-amino-2H-phthalazin-1-one (3 g, 18.61 mmol) in HCl (20 mL) was added NaNO$_2$ (1.28 g, 18.61 mmol) and H$_2$O (5 mL) at −5° C. The mixture was stirred at −5° C. for 1 h. Then it was transferred in one portion to a solution of AcOH (15 mL) with CuCl (460.7 mg, 4.65 mmol) and H$_2$O (5 mL) that was saturated by bubbling SO$_2$. The mixture was stirred at 25° C. for 2 h under an N$_2$ atmosphere. The reaction mixture was concentrated under reduced pressure to give a residue. The crude product of Compound 25-6, 1-oxo-2H-phthalazine-5-sulfonyl chloride (1.5 g, 6.13 mmol, 32.9% yield), was obtained as a yellow solid and was used in the next step without further purification.

EXAMPLE 25: To a solution of 1-oxo-2H-phthalazine-5-sulfonyl chloride (1 g, 4.09 mmol) in DCM (15 mL) was added TEA (853.3 μL, 6.13 mmol) and 6-chloroindoline INDOLINE 2 (502.2 mg, 3.27 mmol). The mixture was stirred at 25° C. for 12 h under an N$_2$ atmosphere. The reaction mixture was diluted with H$_2$O (50 mL) and extracted with DCM (150 mL×2). The combined organic layers were washed with saturated brine (10 mL), dried over anhydrous Na$_2$SO$_4$, filtered and concentrated under reduced pressure to give a residue. The residue was purified by column chromatography (SiO$_2$, petroleum ether:ethyl acetate=10:1 to 0:1). Compound 25, 5-(6-chloroindolin-1-yl)sulfonyl-2H-phthalazin-1-one (0.15 g, 373.3 μmol, 9.13% yield) was obtained as a yellow solid. LC-MS: [M+1] 361.03.

$^1$H NMR (400 MHz, DMSO-d$_6$): δ 13.08 (s, 1H), 8.78 (s, 1H), 8.56 (d, J=8 Hz, 1H), 8.46 (d, J=8 Hz, 1H), 8.02 (t, J=8 Hz, 1H), 7.39 (s, 1H), 7.22 (d, J=8.4 Hz, 1H), 7.09 (d, J=8.4 Hz, 1H), 4.06 (t, J=8 Hz, 2H), 2.90 (t, J=8.4 Hz, 2H).

Example 26

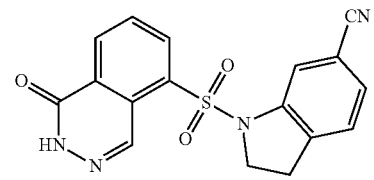 [SMILES: N#Cc1ccc2c(c1)N(S(=O)(=O)c1cccc3c(=O)[nH]ncc13)CC2]

1-((1-Oxo-1,2-dihydrophthalazin-5-yl)sulfonyl)indoline-6-carbonitrile

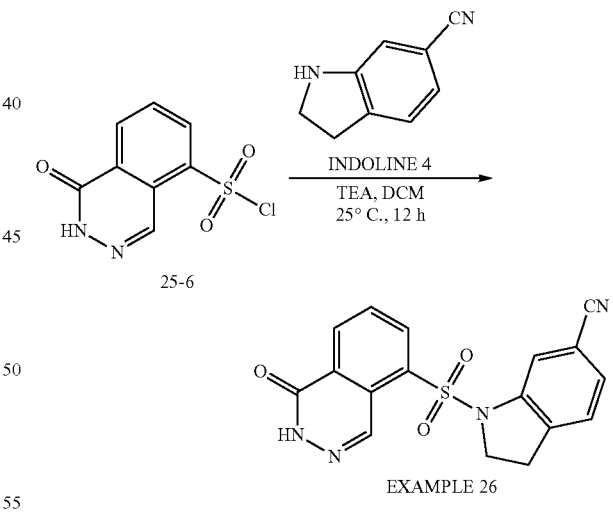

EXAMPLE 26

EXAMPLE 26: To a solution of 1-oxo-2H-phthalazine-5-sulfonyl chloride (0.5 g, 2.04 mmol) in DCM (15 mL) was added TEA (426 μL, 3.07 mmol) and indoline-6-carbonitrile INDOLINE 4 (235 mg, 1.63 mmol). The mixture was stirred at 25° C. for 12 h under an N$_2$ atmosphere. The reaction mixture was diluted with H$_2$O (20 mL) and extracted with EtOAc (80 mL×2). The combined organic layers were washed with saturated brine (20 mL), dried over anhydrous Na$_2$SO$_4$, filtered and concentrated under reduced pressure to give a residue. The residue was purified by column chromatography (SiO$_2$, petroleum ether:ethyl acetate=10:1 to 0:1). Compound 26, 1-[(1-oxo-2H-phthalazin-5-yl)sulfonyl]indoline-6-carbonitrile (30 mg, 81.6 mol, 3.99% yield) was obtained as a yellow solid. LC-MS: [M+1] 352.06.

$^{1}$H NMR (400 MHz, DMSO-$d_{6}$): δ 13.09 (s, 1H), 8.81 (s, 1H), 8.56 (d, J=8 Hz, 2H), 8.01 (t, J=8 Hz, 1H), 7.72 (s, 1H), 7.52 (d, J=9.2 Hz, 1H), 7.41 (d, J=7.6 Hz, 1H), 4.08 (t, J=8.4 Hz, 2H), 3.03 (t, J=8.4 Hz, 2H).

Example 27

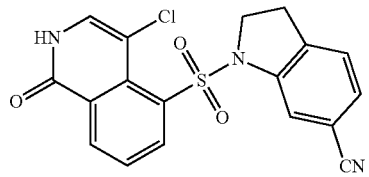 [SMILES: N#Cc1ccc2c(c1)N(S(=O)(=O)c1cccc3c(=O)[nH]cc(Cl)c13)CC2]

1-((4-chloro-1-oxo-1,2-dihydroisoquinolin-5-yl)sulfonyl)indoline-6-carbonitrile

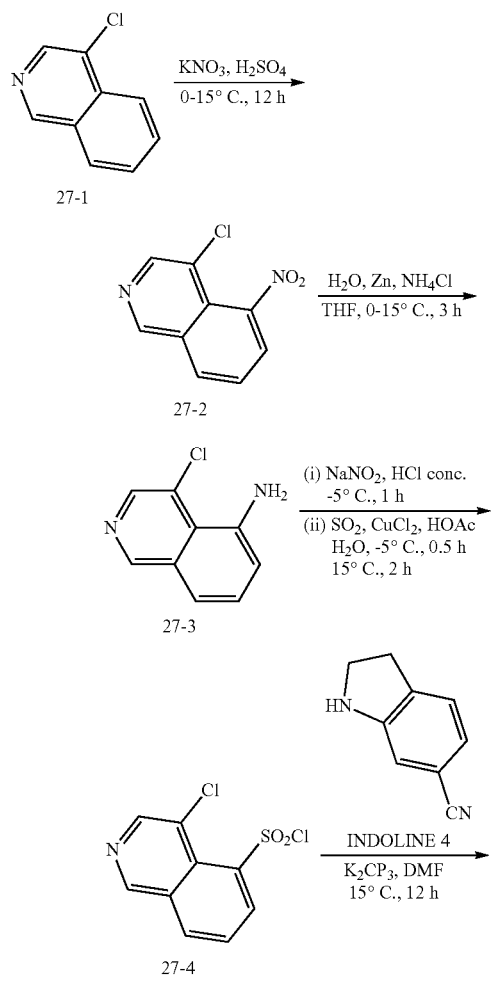

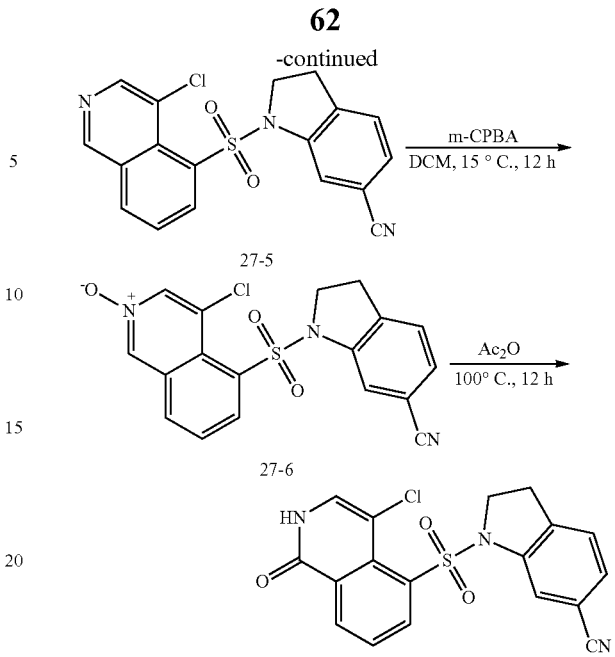

EXAMPLE 27

Compound 27-2. To a mixture of 4-chloroisoquinoline (5 g, 30.56 mmol, 1 eq) in H$_2$SO$_4$ (20 mL) KNO$_3$ (3.40 g, 33.62 mmol, 1.1 eq) was added at 0° C. under N$_2$. The mixture was stirred at 15° C. for 12 hours. The reaction mixture was added to ice-cold water (100 ml), and then saturated NaOH solution was added until the pH was adjusted to pH=10. The mixture was extracted with EtOAc (200 mL×2). The combined organic layers were washed with brine (200 mL), dried over Na$_2$SO$_4$, filtered and concentrated under reduced pressure to give a residue. The residue was washed with the mixture solvent of petroleum ether:ethyl acetate=1:1 (50 mL). The mixture was filtered and concentrated under reduced pressure to give a residue. Compound 27-2, 4-chloro-5-nitro-isoquinoline (4 g, 19.18 mmol, 62.74% yield), was obtained as a yellow solid.

Compound 27-3: To a solution of 4-chloro-5-nitro-isoquinoline (4 g, 19.18 mmol, 1 eq) and NH$_4$Cl (8.21 g, 153.40 mmol, 8 eq) in THF (50 mL) and H$_2$O (25 mL) Zn (10.03 g, 153.40 mmol, 8 eq) was added at 0° C. The resulting mixture was stirred at 15° C. for 3 hr. The reaction mixture was filtered, and the filtrate was added to H$_2$O (200 mL) and extracted with EtOAc (150 mL×2). The combined organic layers were washed with brine (200 mL), dried over Na$_2$SO$_4$, filtered and concentrated under reduced pressure to give a residue. The residue was purified by column chromatography (SiO$_2$, petroleum ether:ethyl acetate=1:0 to 0:1). Compound 27-3, 4-chloroisoquinolin-5-amine (1.5 g, 8.40 mmol, 43.79% yield), was obtained as a light yellow solid.

Preparation of Solution 1: To a mixture of 4-chloroisoquinolin-5-amine (1.5 g, 8.40 mmol, 1 eq) in conc. HCl (15 mL) was added NaNO$_2$ (579.45 mg, 8.40 mmol, 1 eq) in one portion at −5° C. under N$_2$. The mixture was stirred at −5° C. for 1 hr.

Preparation of Solution 2: SO$_2$ was bubbled into a solution of CuCl (207.85 mg, 2.10 mmol, 0.25 eq) in HOAc (15 mL) and H$_2$O (3 mL) at 0° C. for 30 minutes.

Compound 27-4: To solution 1 solution 2 was added slowly. The mixture was stirred at 15° C. for 2 hr. The reaction mixture was concentrated under reduced pressure to remove solvent.

The residue was diluted with H₂O (500 mL) and extracted with DCM (300 mL×3). The combined organic layers were washed with brine (500 mL), dried over Na₂SO₄, filtered and concentrated under reduced pressure to give a residue that was used with no further purification. Compound 27-4, 4-chloroisoquinoline-5-sulfonyl chloride (1.5 g, crude), was obtained as a yellow solid.

Compound 27-5: To a mixture of 4-chloroisoquinoline-5-sulfonyl chloride (1.5 g, 5.72 mmol, 1 eq) and indoline-6-carbonitrile INDOLINE 4 (825.06 mg, 5.72 mmol, 1 eq) in DMF (20 mL) K₂CO₃ (1.58 g, 11.45 mmol, 2 eq) was added in one portion at 15° C. under N₂. The mixture was stirred at 15° C. for 12 hours. The reaction mixture was diluted with H₂O (200 mL) and extracted with EtOAc (150 mL×3). The combined organic layers were dried over Na₂SO₄, filtered and concentrated under reduced pressure to give a residue. The residue was purified by column chromatography (SiO₂, petroleum ether:ethyl acetate=1:0 to 0:1). Compound 27-5, 1-[(4-chloro-5-isoquinolyl)sulfonyl]indoline-6-carbonitrile (600 mg, crude), was obtained as a yellow solid.

Compound 27-6: To a solution of 1-[(4-chloro-5-isoquinolyl)sulfonyl]indoline-6-carbonitrile (600 mg, 1.62 mmol, 1 eq) in DCM (20 mL) was added m-CPBA (769.93 mg, 3.57 mmol, 80% purity, 2.2 eq).The mixture was stirred at 15° C. for 12 hr. The reaction mixture was purified directly by column chromatography (SiO₂, petroleum ether:ethyl acetate=1:0 to ethyl acetate: EtOH=3:1). The crude product of Compound 27-6 was obtained triturated with MeOH (50 mL), filtered and was used in the next step without further purification.

EXAMPLE 27: A mixture of 1-(4-chloro-2-oxido-isoquinolin-2-ium-5-yl)sulfonylindoline-6-carbonitrile (150 mg, 388.78 µmol, 1 eq) in Ac₂O (15 mL) was heated to 100° C. and stirred for 12 hours. The reaction mixture was concentrated under reduced pressure to remove solvent. The residue was purified by prep-HPLC (column: Xtimate C18 150×25 mm×5 µm; mobile phase: [water(10 mM NH₄HCO₃)-ACN];B %: 40%-70%,10 min). Then the residue was re-purified by prep-HPLC (column: Xtimate C18 150×25 mm×5 µm;mobile phase: [water(10 mM NH₄HCO₃)-ACN];B %: 30%-55%, 8 min). EXAMPLE 27, 1-[(4-chloro-1-oxo-2H-isoquinolin-5-yl)sulfonyl]indoline-6-carbonitrile (4 mg, 9.63 µmol, 2.48% yield, 92.93% purity), was obtained as a yellow solid. LCMS (ESI+) m/z: 383.0.

¹H NMR (400 MHz, DMSO-d₆): 8.55 (d, J=8 Hz, 1H), 7.98 (d, J=7.6 Hz, 1H), 7.63-7.46 (m, 4H), 7.21 (s, 1H), 4.15 (t, J=8.6 Hz, 2H), 3.34 (t, J=8.8 Hz, 2H).

Example 28

1-((1-oxo-1,2-dihydroisoquinolin-5-yl)sulfonyl)-2,3-dihydro-1H-pyrrolo[3,2-c]pyridine-6-carbonitrile

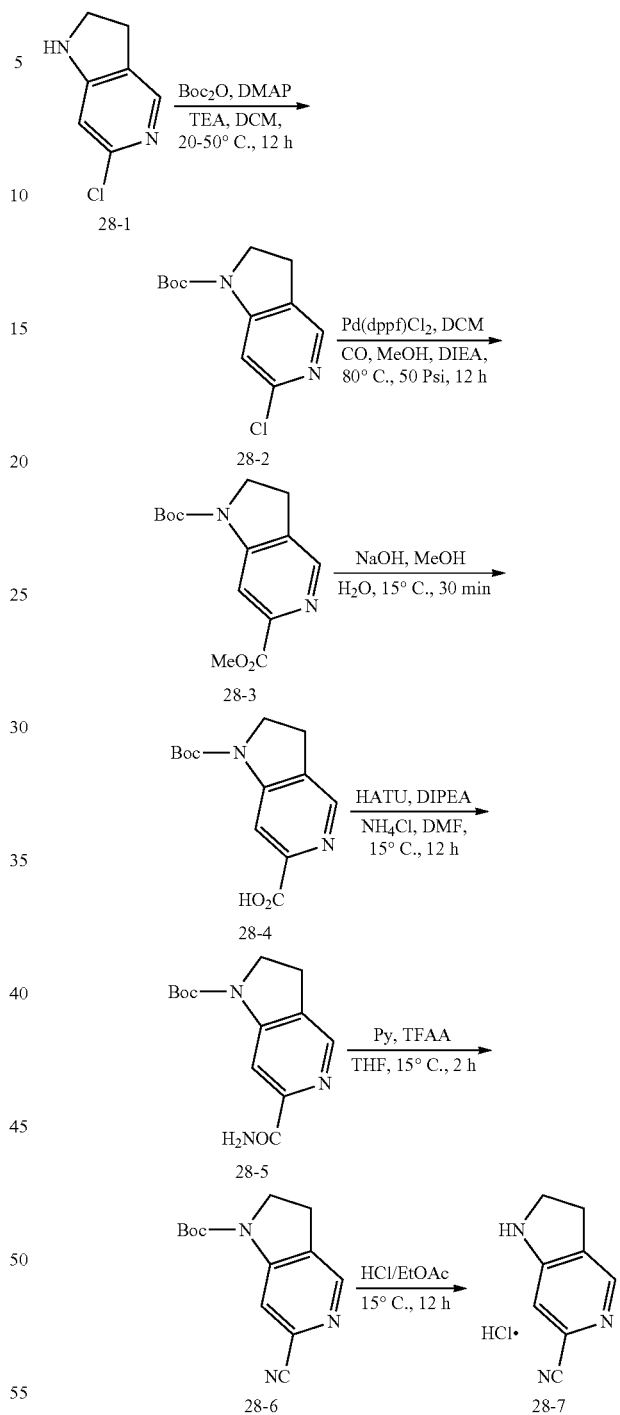

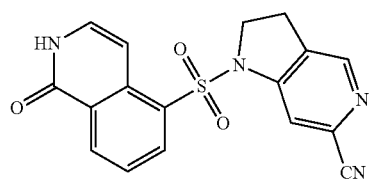 [SMILES: N#Cc1cc2c(cn1)CCN2S(=O)(=O)c1cccc2c(=O)[nH]ccc12]

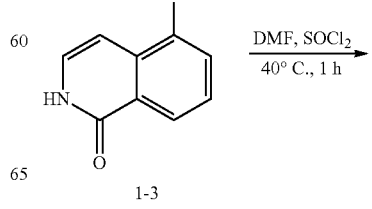

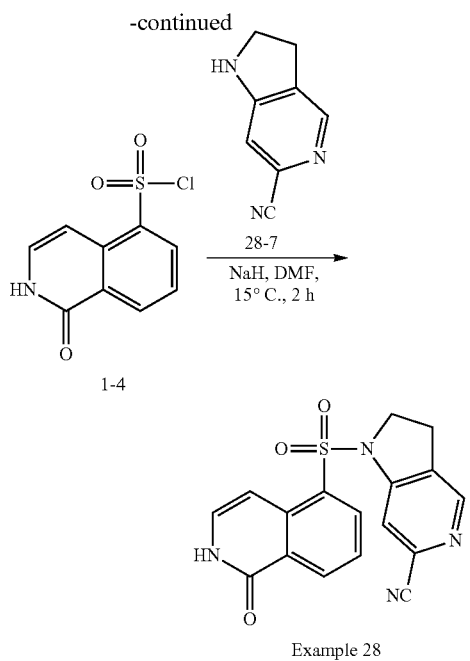

Example 28

Compound 28-2: To a solution of 6-chloro-2, 3-dihydro-1H-pyrrolo[3,2-c]pyridine (1.6 g, 10.35 mmol, 1 eq) in DCM (20 mL), Boc₂O (6.78 g, 31.05 mmol, 7.13 mL, 3 eq), TEA (2.09 g, 20.70 mmol, 2.88 mL, 2 eq) and DMAP (1.26 g, 10.35 mmol, 1 eq) were added at 20° C. The mixture was heated to 50° C. and stirred for 12 hours. The reaction mixture was concentrated under reduced pressure to remove solvent. The residue was purified by column chromatography (SiO₂, petroleum ether:ethyl acetate=1:0 to 0:1). Compound 28-2, tert-butyl 6-chloro-2, 3-dihydropyrrolo[3,2-c]pyridine-1-carboxylate (1.5 g, 5.89 mmol, 56.90% yield), was obtained as a colorless oil.

Compound 28-3: To a solution of tert-butyl 6-chloro-2, 3-dihydropyrrolo[3,2-c]pyridine-1-carboxylate (1.5 g, 5.89 mmol, 1 eq) in MeOH (50 mL) and DIPEA (5 mL) Pd(dppf)Cl₂.CH₂Cl₂ (2.40 g, 2.94 mmol, 0.5 eq) was added at 15° C. The suspension was degassed under vacuum and purged with CO several times. The mixture was stirred under CO (50 psi) at 80° C. for 12 hours. The reaction mixture was concentrated under reduced pressure to remove solvent. The residue was purified by column chromatography (SiO₂, petroleum ether:ethyl acetate=1:0 to 0:1). Compound 28-3, Ol-tert-butyl 06-methyl 2,3-dihydropyrrolo[3,2-c]pyridine-1,6-dicarboxylate (1.5 g, 4.31 mmol, 73.22% yield, 80% purity), was obtained as a red solid.

Compound 28-4: To a solution of Ol-tert-butyl 06-methyl 2,3-dihydropyrrolo[3,2-c]pyridine-1,6-dicarboxylate (1.57 g, 5.64 mmol, 1 eq) in MeOH (20 mL) and H₂O (4 mL) NaOH (676.96 mg, 16.92 mmol, 3 eq) was added. The mixture was stirred at 15° C. for 30 min. The reaction mixture was concentrated under reduced pressure to remove MeOH. Then to the remaining solution was added 12M HCl solution until pH=3~4, and the mixture was extracted with EtOAc (100 mL×2). The combined organic layers were dried over Na₂SO₄, filtered and concentrated under reduced pressure to give a residue that was used with no further purification. Compound 28-4, 1-tert-butoxycarbonyl-2,3-dihydropyrrolo[3,2-c]pyridine-6-carboxylic acid (700 mg, crude), was obtained as a yellow solid.

Compound 28-5: To a solution of 1-tert-butoxycarbonyl-2,3-dihydropyrrolo[3,2-c]pyridine-6-carboxylic acid (650 mg, 2.46 mmol, 1 eq) in DMF (10 mL) HATU (1.40 g, 3.69 mmol, 1.5 eq), NH₄Cl (526.24 mg, 9.84 mmol, 4 eq) and DIPEA (1.59 g, 12.30 mmol, 2.14 mL, 5 eq) were added. The mixture was stirred at 15° C. for 12 hr. The reaction mixture was added to H₂O (150 mL) and extracted with EtOAc (80 mL×2). The combined organic layers were washed with brine (150 mL), dried over Na₂SO₄, filtered and concentrated under reduced pressure to give a residue. The residue was purified by column chromatography (SiO₂, petroleum ether:ethyl acetate=1:0 to 0:1). Compound 28-5, tert-Butyl 6-carbamoyl-2,3-dihydropyrrolo[3,2-c]pyridine-1-carboxylate (300 mg, 46% yield), was obtained as a white solid.

Compound 28-6: To a solution of tert-butyl 6-carbamoyl-2,3-dihydropyrrolo[3,2-c]pyridine-1-carboxylate (250 mg, 949.52 μmol, 1 eq) in THF (10 mL), pyridine (195.28 mg, 2.47 mmol, 199.26 μL, 2.6 eq) and TFAA (518.51 mg, 2.47 mmol, 343.38 μL, 2.6 eq) were added. The mixture was stirred at 15° C. for 2 hr. The reaction mixture was added to H₂O (100 mL) and extracted with EtOAc (50 mL×2). The combined organic layers were washed with brine (100 mL), dried over Na₂SO₄, filtered and concentrated under reduced pressure to give a residue. The residue was purified by column chromatography (SiO₂, petroleum ether:ethyl acetate=1:0 to 1:1). Compound 28-6, tert-butyl 6-cyano-2,3-dihydropyrrolo[3,2-c]pyridine-1-carboxylate (250 mg, crude), was obtained as a light yellow solid.

Compound 28-7: A solution of tert-butyl 6-cyano-2,3-dihydropyrrolo[3,2-c]pyridine-1-carboxylate (250 mg, 1.02 mmol, 1 eq) in HCl:EtOAc (10 mL) was stirred at 15° C. for 12 hr. The reaction mixture was concentrated under reduced pressure to remove solvent. The residue was used with no further purification. Compound 28-7, 2,3-dihydro-1H-pyrrolo[3,2-c]pyridine-6-carbonitrile (160 mg, crude, HCl), was obtained as an off-white solid.

Compound 1-4: A mixture of 1-hydroxyisoquinoline-5-sulfonic acid 1-3 (1.00 g, 4.44 mmol, 1 eq) in SOCl₂ (10 mL) and DMF (0.1 mL) was heated to 40° C. and stirred for 1 h. The reaction mixture was concentrated under reduced pressure to remove the solvent. The residue was diluted with H₂O (100 mL) and extracted with DCM (70 mL×2). The combined organic layers were washed with brine (100 mL), dried over Na₂SO₄, filtered and concentrated under reduced pressure to give a residue. The residue was purified by column chromatography (SiO₂, petroleum ether:ethyl acetate=1:0 to 0:1). Compound 1-4,1-oxo-2H-isoquinoline-5-sulfonyl chloride (300 mg, crude) was obtained as a yellow solid which was used directly in the next step.

EXAMPLE 28: To a solution of 2,3-dihydro-1H-pyrrolo[3,2-c]pyridine-6-carbonitrile 28-7 (37.53 mg, 258.55 μmol, 0.7 eq) in DMF (7 mL) NaH (59.10 mg, 1.48 mmol, 78.02 μL, 60% purity, 4 eq) was added at 15° C. The mixture was stirred at this temperature for 30 min, and then 1-oxo-2H-isoquinoline-5-sulfonyl chloride 1-4 (90 mg, 369.36 μmol, 1 eq) was added at 15° C. The resulting mixture was stirred at 15° C. for 1.5 hr. The reaction mixture was quenched by addition of H₂O (20 mL), and then diluted with H₂O (40 mL) and extracted with EtOAc (20 mL×2). The combined organic layers were washed with brine (60 mL), dried over Na₂SO₄, filtered and concentrated under reduced pressure to give a residue. The residue was purified by prep-HPLC (column: Xtimate C18 150×25 mm×5 m; mobile phase: [water(10 mM NH₄HCO₃)-ACN];B %: 20%-50%, 8 min). EXAMPLE 28, 1-[(1-oxo-2H-isoquinolin-5-yl)sulfonyl]-2, 3-dihydropyrrolo[3,2-c]pyridine-6-carbonitrile (3 mg, purity 98.76%), was obtained as a white solid. LCMS (ESI+)/mz: 353.0.

¹H NMR (400 MHz, DMSO-d₆): δ 11.74 (br, 1H), 8.56 (d, J=8 Hz, 1H), 8.51~8.46 (m, 2H), 7.75 (s, 1H), 7.67 (t, J=8 Hz, 1H), 7.45~7.37 (m, 1H), 7.11 (d, J=7.6 Hz, 1H), 4.10 (t, J=8.8 Hz, 2H), 3.22 (t, J=8.6 Hz, 2H).

Example 29

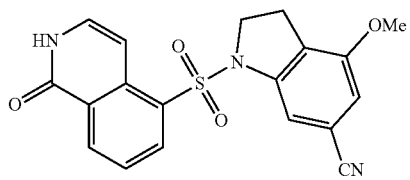 [SMILES: COc1cc(C#N)cc2c1CCN2S(=O)(=O)c1cccc2c(=O)[nH]ccc12]

4-methoxy-1-((1-oxo-1,2-dihydroisoquinolin-5-yl)sulfonyl)indoline-6-carbonitrile

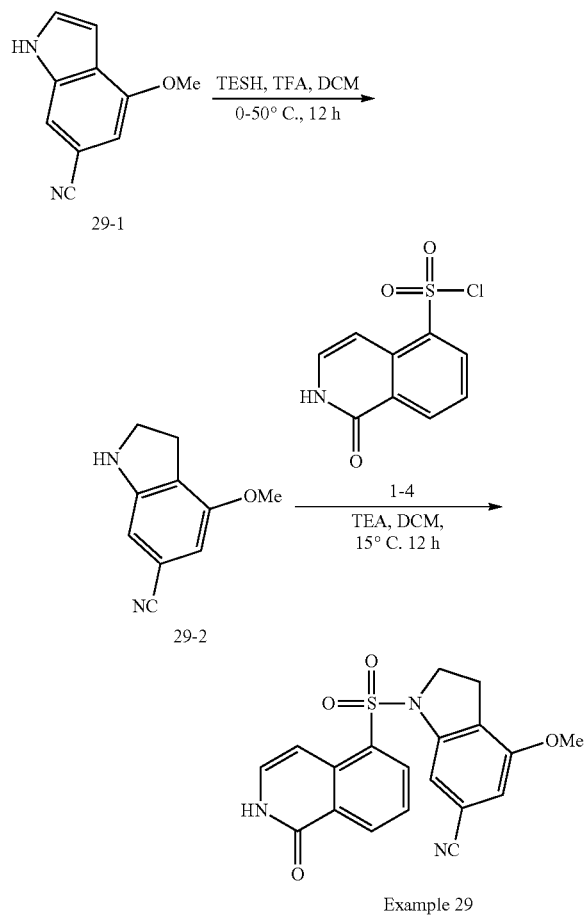

Example 29

Compound 29-2: To a solution of 4-methoxy-1H-indole-6-carbonitrile (230 mg, 1.34 mmol, 1 eq) in DCM (8 mL) was added triethylsilane (776.63 mg, 6.68 mmol, 1.07 mL, 5 eq). The reaction was then cooled to 0° C. and TFA (4 mL) was added dropwise at 0° C. The mixture was heated to 50° C. and stirred for 12 hours. The reaction mixture was concentrated under reduced pressure to remove solvent. The residue was purified by column chromatography (SiO₂, petroleum ether:ethyl acetate=1:0 to 0:1) Compound 29-2, 4-methoxyindoline-6-carbonitrile (100 mg, 40% yield), was obtained as a light yellow solid.

EXAMPLE 29: To a solution of 1-oxo-2H-isoquinoline-5-sulfonyl chloride 1-4 (150 mg, 615.60 μmol, 1 eq) and 4-methoxyindoline-6-carbonitrile 29-2 (32.17 mg, 184.68 μmol, 0.3 eq) in DCM (10 mL) was added TEA (207.64 mg, 1.23 mmol, 285.61 μL, 60% purity, 2 eq). The mixture was stirred at 15° C. for 12 hr. The reaction mixture was added to H₂O (50 mL) and extracted with EtOAc (30 mL×2). The combined organic layers were concentrated under reduced pressure to give a residue. The residue was purified by prep-HPLC (column: Nano-micro Kromasil C18 100×40 mm 10 μm; mobile phase: [water(0.1% TFA)-ACN];B %: 30%-56%,10 min). The residue was re-purified by prep-HPLC (column: Xtimate C18 150×25 mm×5 μm; mobile phase: [water(10 mM NH₄HCO₃)-ACN];B %: 25%-55%, 8 min). EXAMPLE 29, 4-methoxy-1-[(1-oxo-2H-isoquinolin-5-yl)sulfonyl]indoline-6-carbonitrile (2 mg, 96.64% purity), was obtained as a white solid. LCMS (ESI+) m/z: 382.0.

¹H NMR (400 MHz, DMSO-d₆): δ 11.68 (br, 1H), 8.52 (d, J=8 Hz, 1H), 8.34 (d, J=7.6 Hz, 1H), 7.64 (t, J=8 Hz, 1H), 7.38 (d, J=7.6 Hz, 1H), 7.26 (s, 1H), 7.21 (s, 1H), 7.13 (d, J=7.6 Hz, 1H), 4.07 (t, J=8.6 Hz, 2H), 3.82 (s, 3H), 2.99 (t, J=8.6 Hz, 2H).

Examples 30 & 31

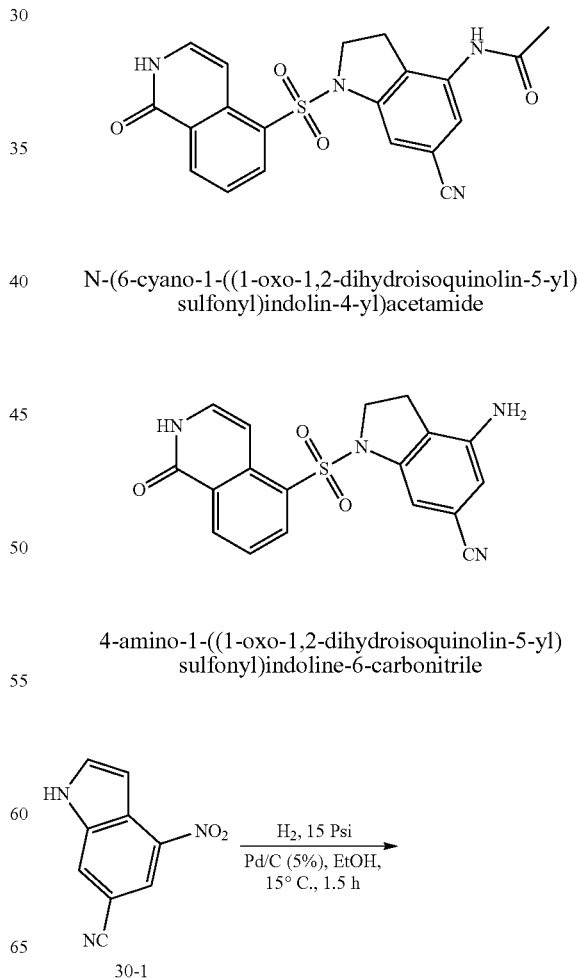

N-(6-cyano-1-((1-oxo-1,2-dihydroisoquinolin-5-yl)sulfonyl)indolin-4-yl)acetamide 4-amino-1-((1-oxo-1,2-dihydroisoquinolin-5-yl)sulfonyl)indoline-6-carbonitrile

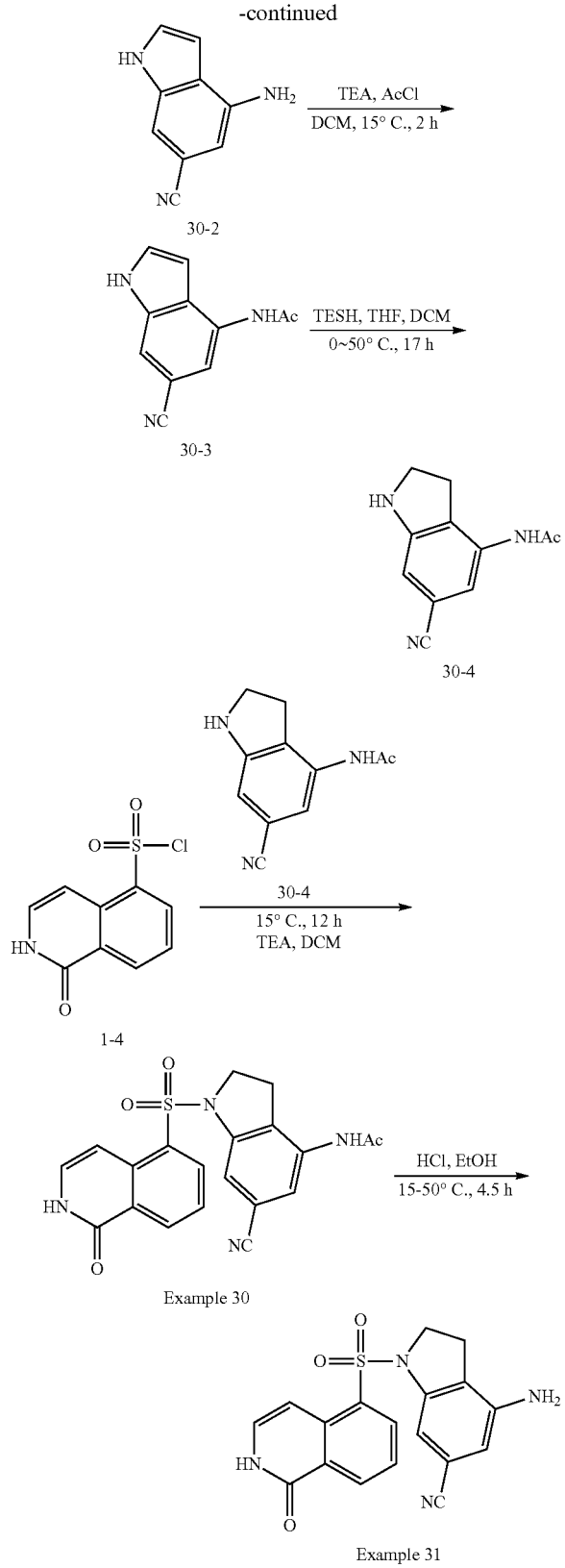

Example 30

Example 31 times. The mixture was stirred under H₂ (15 psi) at 15° C. for 1.5 hours. The reaction mixture was filtered and the filtrate concentrated under reduced pressure to give a residue that was used with no further purification. Compound 30-2, 4-amino-1H-indole-6-carbonitrile (700 mg, 4.45 mmol, 83.35% yield), was obtained as a yellow solid.

Compound 30-3: To a solution of 4-amino-1H-indole-6-carbonitrile (700 mg, 4.45 mmol, 1 eq) in DCM (15 mL) was added TEA (1.35 g, 13.36 mmol, 1.86 mL, 3 eq) and acetyl chloride (419.54 mg, 5.34 mmol, 381.40 µL, 1.2 eq). The mixture was stirred at 15° C. for 2 hr. The reaction mixture was concentrated under reduced pressure to remove solvent. The residue was purified by column chromatography (SiO₂, petroleum ether:ethyl acetate=1:0 to 0:1) by 2 times. Compound 30-3, N-(6-cyano-1H-indol-4-yl)acetamide (600 mg, 3.01 mmol, 67.63% yield), was obtained as a light yellow solid.

Compound 30-4: To a solution of N-(6-cyano-1H-indol-4-yl)acetamide (600 mg, 3.01 mmol, 1 eq) in DCM (20 mL) TESH (3.50 g, 30.12 mmol, 4.81 mL, 10 eq) was added. The reaction was then cooled to 0° C. and TFA (10 mL) was added dropwise at 0° C. The resulting mixture was stirred at 15° C. for 12 hr. The mixture was heated to 50° C. and stirred for 5 hours. The reaction mixture was concentrated under reduced pressure to remove solvent. The residue was purified by column chromatography (SiO₂, petroleum ether:ethyl acetate=1:0 to 0:1). Compound 30-4, N-(6-cyanoindolin-4-yl)acetamide (400 mg, 1.99 mmol, 66.00% yield), was obtained as a light yellow solid.

EXAMPLE 30: To a solution of 1-oxo-2H-isoquinoline-5-sulfonyl chloride 1-4 (200 mg, 820.79 µmol, 1 eq) in DCM (10 mL), TEA (332.22 mg, 3.28 mmol, 456.98 µL, 4 eq) and N-(6-cyanoindolin-4-yl)acetamide (82.58 mg, 410.40 µmol, 0.5 eq) were added. The mixture was stirred at 15° C. for 12 hr. The reaction mixture was added to H₂O (150 mL) and extracted with EtOAc (80 mL×2). The combined organic layers were concentrated under reduced pressure to give a residue. The residue was purified by column chromatography (SiO₂, petroleum ether:ethyl acetate=1:0, DCM:MeOH=2:1). The residue was re-purified by prep-HPLC (column: Xtimate C18 150×25 mm×5 m; mobile phase: [water(10 mM NH₄HCO₃)-ACN];B %: 20%-50%,8 min). EXAMPLE 30, N-[6-cyano-1-[(1-oxo-2H-isoquinolin-5-yl)sulfonyl]indolin-4-yl]acetamide (20 mg, 96.9% purity), was obtained as a white solid. LCMS (ESI+) m/z: 409.1.

¹H NMR (400 MHz, DMSO-d₆): δ 11.67 (br, 1H), 9.58 (s, 1H), 8.49 (d, J=8 Hz, 1H), 8.33 (d, J=8 Hz, 1H), 7.83 (s, 1H), 7.61 (t, J=8 Hz, 1H), 7.36~7.28 (m, 2H), 7.07 (d, J=7.2 Hz, 1H), 4.04 (t, J=8.4 Hz, 2H), 2.97 (t, J=8.4 Hz, 2H), 2.03 (s, 1H).

EXAMPLE 31: A mixture of N-[6-cyano-1-[(1-oxo-2H-isoquinolin-5-yl)sulfonyl]indolin-4-yl]acetamide (40 mg, 97.94 µmol, 1 eq) in conc. HCl (6 mL) and EtOH (6 mL) was heated to 50° C. and stirred for 4.5 hours. The reaction mixture was added to aq. Na₂CO₃ until pH>7, and then diluted with H₂O (20 mL) and extracted with DCM (50 mL×2).

The combined organic layers were concentrated under reduced pressure to give a residue. The residue was purified by prep-HPLC (column: Welch Ultimate AQ-C18 150×30 mm×5 µm; mobile phase: [water(0.1% TFA)-ACN];B %: 25%-55%,12 min). EXAMPLE 31, 4-amino-1-[(1-oxo-2H-isoquinolin-5-yl)sulfonyl]indoline-6-carbonitrile (14 mg, 98.04% purity, TFA salt), was obtained as a white solid. LCMS (ESI+) m/z: 367.1.

¹H NMR (400 MHz, DMSO-d₆): δ 11.69 (d, J=5.6 Hz, 1H), 8.51 (d, J=7.6 Hz, 1H), 8.27 (d, J=7.6 Hz, 1H), 7.63 (t,

Compound 30-2: To a solution of 4-nitro-1H-indole-6-carbonitrile (1.00 g, 5.34 mmol, 1 eq) in EtOH (20 mL) Pd/C (1.00 g, 106.86 µmol, 5% wt %) under N₂. The suspension was degassed under vacuum and purged with H₂ several J=7.8 Hz, 1H), 7.37 (t, J=6.8 Hz, 1H), 7.13 (d, J=7.6 Hz, 1H), 6.78 (s, 1H), 6.61 (s, 1H), 5.65 (br, 2H), 4.05 (t, J=8.4 Hz, 2H), 2.77 (t, J=8.4 Hz, 2H).
Examples 32, 33 & 34
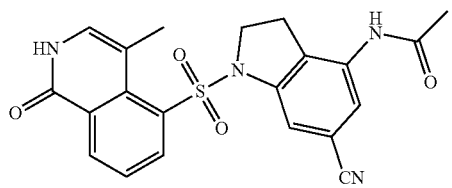 [SMILES: CC(=O)Nc1cc(C#N)cc2c1CCN2S(=O)(=O)c1cccc2c(=O)[nH]cc(C)c12]
N-(6-cyano-1-((4-methyl-1-oxo-1,2-dihydroisoquinolin-5-yl)sulfonyl)indolin-4-yl)acetamide
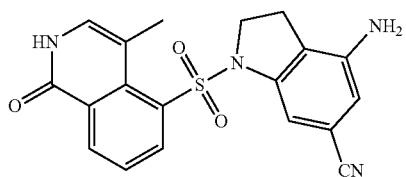 [SMILES: Cc1c[nH]c(=O)c2cccc(S(=O)(=O)N3CCc4c(N)cc(C#N)cc43)c12]
4-amino-1-((4-methyl-1-oxo-1,2-dihydroisoquinolin-5-yl)sulfonyl)indoline-6-carbonitrile
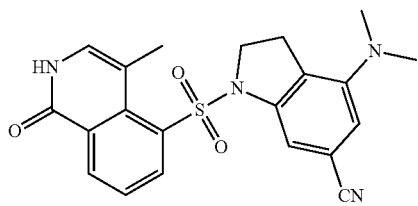 [SMILES: Cc1c[nH]c(=O)c2cccc(S(=O)(=O)N3CCc4c(N(C)C)cc(C#N)cc43)c12]
4-(dimethylamino)-1-((4-methyl-1-oxo-1,2-dihydroisoquinolin-5-yl)sulfonyl)indoline-6-carbonitrile
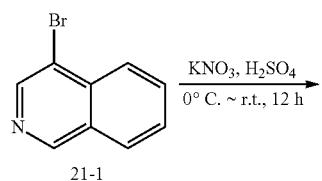
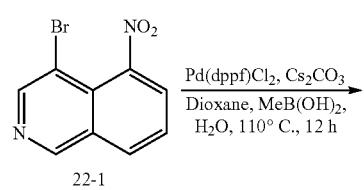
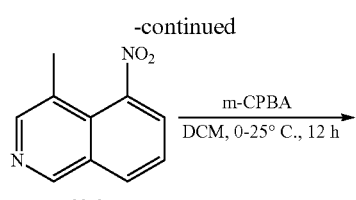
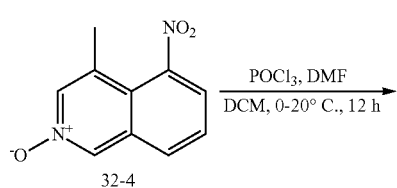
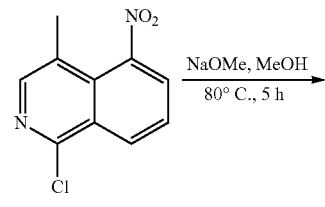
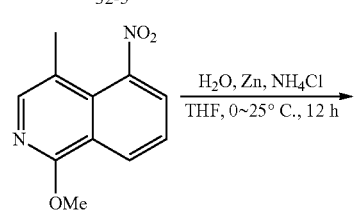
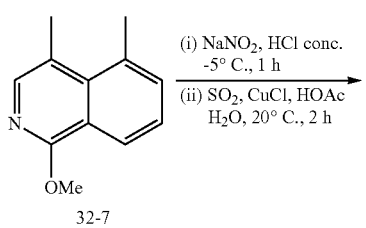
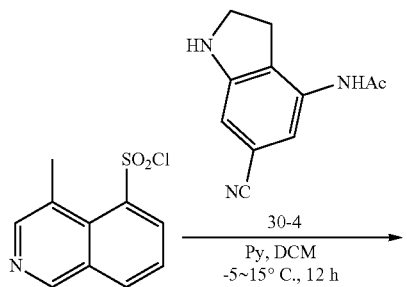
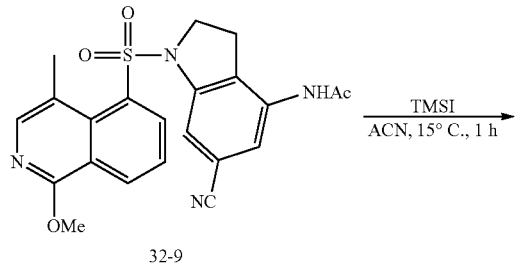

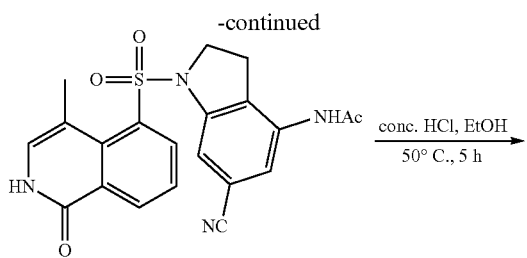

Example 32

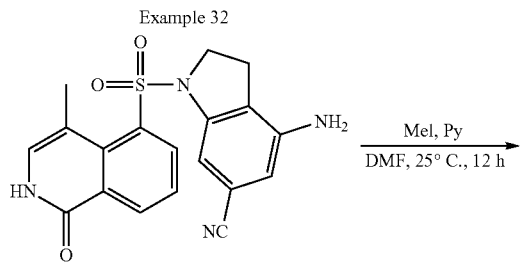

Example 33

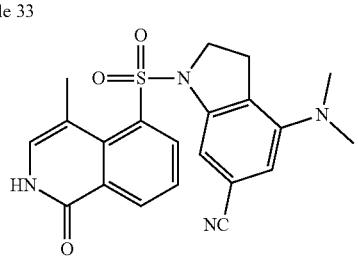

Example 34

Compound 22-1: Three reaction mixtures were prepared in parallel as follows: to a solution of 4-bromoisoquinoline 21-1 (100 g, 480.64 mmol, 1 eq) in $H_2SO_4$ (250 mL) $KNO_3$ (53.45 g, 528.71 mmol, 1.1 eq) was added at 0° C. The mixture was stirred at 25° C. for 12 hr under $N_2$ atmosphere. The reaction mixture was quenched by addition to ice water (1 L) at 0° C., and then aq. NaOH solution (800 mL) was added to the mixture to adjust pH to −8. The mixture was filtered and the filter cake was concentrated under reduced pressure to give a residue. The residue was triturated with petroleum ether: EtOAc=1:1.5 (2.5 L) at 25° C. for 12 hr. Filtered and the solid was triturated with $H_2O$ (1. 5 L) at 25° C. for 5 hr. Compound 32-2, 4-bromo-5-nitro-isoquinoline 22-1 (200 g, 790.35 mmol, 54.81% yield), was obtained as a yellow solid. LCMS (ESI+) m/z: 252.9.

Compound 22-2: Two reaction mixtures were prepared in parallel as follows: a mixture of 4-bromo-5-nitro-isoquinoline 22-1 (50 g, 197.59 mmol, 1 eq), $Cs_2CO_3$ (128.76 g, 395.18 mmol, 2 eq), Pd(dppf)$Cl_2$ (14.46 g, 19.76 mmol, 0.1 eq) and MeB(OH)$_2$ (23.66 g, 395.18 mmol, 2 eq) in dioxane (400 mL) and $H_2O$ (40 mL) was degassed and purged with $N_2$ 3 times, and then the mixture was stirred at 110° C. for 12 hr under $N_2$ atmosphere. Two batches with the same scale (50 g) were run in parallel and run work-up/purification together. The reaction mixture was concentrated under reduced pressure to remove dioxane. The residue was diluted with $H_2O$ (1.5 L) and extracted with EtOAc (2 L×3). The combined organic layers were dried over $Na_2SO_4$, filtered and concentrated under reduced pressure to give a residue. The residue was purified by column chromatography (SiO$_2$, petroleum ether:ethyl acetate=10:1 to 1:1). Compound 22-2, 4-methyl-5-nitro-isoquinoline (40 g, 212.56 mmol, 53.79% yield), was obtained as a yellow solid.

Compound 32-4: To a solution of 4-methyl-5-nitro-isoquinoline 22-2 (60 g, 318.84 mmol, 1 eq) in DCM (800 mL) was added m-CPBA (151.31 g, 701.44 mmol, 80% purity, 2.2 eq) at 0° C. The mixture was stirred at 25° C. for 12 hr. The reaction mixture was quenched by addition aq. $Na_2SO_3$ (900 mL). The reaction mixture was diluted with $H_2O$ (1 L) and extracted with DCM (2000 mL×4). The combined organic layers were dried over anhydrous $Na_2SO_4$, filtered and concentrated under reduced pressure to give a residue. The residue was triturated with EtOAc (2000 mL) at 25° C. for 2 hr and the solid was dried under reduced pressure. Compound 32-4, 4-methyl-nitro-2-xido-isquinolin-2-ium (40 g, 195.90 mmol, 61.44% yield), was obtained as a yellow solid.

Compound 32-5: To a solution of 4-methyl-5-nitro-2-oxido-isoquinolin-2-ium (45 g, 220.39 mmol, 1 eq) in DCM (500 mL), POCl$_3$ (40.55 g, 264.47 mmol, 24.58 mL, 1.2 eq) and DMF (8.05 g, 110.20 mmol, 8.48 mL, 0.5 eq) were added at 0° C. The mixture was stirred at 20° C. for 12 hr under $N_2$ atmosphere. The reaction mixture was concentrated under reduced pressure to remove DCM. The residue was quenched with $H_2O$ (300 mL) and then it was filtered. The filter cake was dried under reduced pressure to give a residue that was used with no further purification. The crude product Compound 32-5, 1-chloro-4-methyl-5-nitro-isoquinoline (27 g, crude), was obtained as a yellow solid. LCMS (ESI+) m/z: 222.9.

Compound 32-6: A mixture of 1-chloro-4-methyl-5-nitro-isoquinoline (27 g, 121.28 mmol, 1 eq), NaOMe (13.10 g, 242.56 mmol, 2 eq) in MeOH (500 mL) was degassed and purged with $N_2$ 3 times, and then the mixture was stirred at 80° C. for 5 hr under a $N_2$ atmosphere. The reaction mixture was concentrated under reduced pressure to remove MeOH. The residue was diluted with $H_2O$ (500 mL) and extracted with EtOAc (600 mL×4). The combined organic layers were dried over $Na_2SO_4$, filtered and concentrated under reduced pressure to give a residue. The residue was purified by column chromatography (SiO$_2$, petroleum ether:ethyl acetate=1:0 to 5:1). Compound 32-6, 1-methoxy-4-methyl-5-nitro-isoquinoline (15 g, 68.74 mmol, 56.68% yield), was obtained as a yellow solid.

Compound 32-7: To a solution of 1-methoxy-4-methyl-5-nitro-isoquinoline (15 g, 68.74 mmol, 1 eq) in MeOH (210 mL) and $H_2O$ (70 mL), Zn (22.48 g, 343.71 mmol, 5 eq) and NH$_4$Cl (18.39 g, 343.71 mmol, 5 eq) were added at 0° C. The mixture was stirred at 25° C. for 12 hr. The mixture was filtered and the filtrate was concentrated under reduced pressure to give a residue. The residue was purified by column chromatography (SiO$_2$, petroleum ether:ethyl acetate=10:1 to 1:1). Compound 32-7, 1-methoxy-4-methyl-isoquinolin-5-amine (10 g, 53.13 mmol, 77.29% yield), was obtained as a brown solid. LCMS (ESI+) m/z: 189.0.

Compound 32-8: To a solution of 1-methoxy-4-methyl-isoquinolin-5-amine (2 g, 10.63 mmol, 1 eq) in HCl (80 mL), NaNO$_2$ (903.12 mg, 10.63 mmol, 1 eq) in $H_2O$ (5 mL) was added at −5° C. The mixture was stirred at −5° C. for 1 hr and transferred to a solution of AcOH (50 mL) with CuCl (262.98 mg, 2.66 mmol, 63.52 µL, 0.25 eq) in $H_2O$ (5 mL) which was saturated by SO$_2$ in one portion. The mixture was stirred at 20° C. for 2 hr. The reaction mixture was quenched by addition to ice water (100 mL) at 0° C., and then the mixture was extracted with DCM (200 mL×3). The combined organic layers were dried over $Na_2SO_4$, filtered and concentrated under reduced pressure to give a residue that was used with no further purification. Compound 32-8, 1-methoxy-4-methyl-isoquinoline-5-sulfonyl chloride (1.5 g, crude), was obtained as a yellow solid. LCMS (ESI+) m/z: 271.9.

Compound 32-9: To a mixture of N-(6-cyanoindolin-4-yl)acetamide 30-4 (888.67 mg, 4.42 mmol, 1.2 eq) and pyridine (1.05 g, 13.25 mmol, 1.07 mL, 3.6 eq) was added dropwise a solution of 1-methoxy-4-methylisoquinoline-5-sulfonyl chloride 32-8 (780 mg, 2.87 mmol, 0.78 eq) in DCM (10 mL) −5° C. The mixture was degassed and purged with N₂ 3 times, and then the mixture was stirred at 15° C. for 12 hr under N₂ atmosphere. The reaction mixture was filtered and concentrated under reduced pressure to give a residue. Crude Compound 32-9, N-(6-cyano-1-((1-methoxy-4-methylisoquinolin-5-yl)sulfonyl)indolin-4-yl)acetamide (1.2 g, crude), was obtained as a brown solid and used into next step without further purification.

EXAMPLE 32: A mixture of N-(6-cyano-1-((1-methoxy-4-methylisoquinolin-5-yl)sulfonyl)indolin-4-yl)acetamide (600 mg, 1.37 mmol, 1 eq) and TMSI (1.10 g, 5.50 mmol, 748.43 μL, 4 eq) in ACN (10 mL) was stirred at 15° C. for 1 hr under N₂ atmosphere. The reaction mixture was quenched by addition H₂O (30 mL) at 0° C., and then extracted with EtOAc (30 mL×2). The combined organic layers were washed with brine (60 mL×1), dried over Na₂SO₄, filtered and concentrated under reduced pressure to give a residue. The residue was purified by prep-TLC (SiO₂, DCM: MeOH=10:1), then it was re-purified by prep-HPLC (column: Waters Xbridge BEH C18 100×25 mm×5 m; mobile phase: [water (10 mM NH₄HCO₃)-ACN]; B %: 15%-50%, 8 min). EXAMPLE 32, N-(6-cyano-1-((4-methyl-1-oxo-1,2-dihydroisoquinolin-5-yl)sulfonyl)indolin-4-yl)acetamide (4 mg, 9.46 μmol, 99.9% purity), was obtained as a white solid. LCMS (ESI+) m/z: 423.1.

¹H NMR (400 MHz, DMSO-d₆): δ 11.69 (br, 1H), 9.74 (s, 1H), 8.59 (d, J=4 Hz, 1H), 7.98~7.85 (m, 2H), 7.52 (t, J=7.6 Hz, 1H), 7.24 (s, 1H), 6.99 (s, 1H), 4.22 (t, J=8.4 Hz, 2H), ~3.31 (2H, mixed with solvent peak), 2.59 (s, 3H), 2.14 (s, 3H).

EXAMPLE 33: A solution of N-(6-cyano-1-((4-methyl-1-oxo-1,2-dihydroisoquinolin-5-yl)sulfonyl)indolin-4-yl)acetamide (30 mg, 71.01 μmol, 1 eq) in conc. HCl (5 mL) and EtOH (5 mL) was stirred at 50° C. for 5 hr. The reaction mixture was added saturated Na₂CO₃ solution until pH=8 at 0° C., and then extracted with EtOAc (60 mL×5). The combined organic layers were washed with brine (200 mL×1), dried over Na₂SO₄, filtered and concentrated under reduced pressure to give a residue. The residue was purified by prep-HPLC (column: Waters Xbridge BEH C18 100×25 mm×5 m; mobile phase: [water (10 mM NH₄HCO₃)-ACN]; B %: 20%-50%, 8 min). EXAMPLE 33, 4-amino-1-((4-methyl-1-oxo-1,2-dihydroisoquinolin-5-yl)sulfonyl)indoline-6-carbonitrile (3.8 mg, 9.87 μmol, 13.89% yield, 98.77% purity), was obtained as a white solid. LCMS (ESI+) m/z: 381.0.

1H NMR (400 MHz, DMSO-d₆): δ 11.66 (br, 1H), 8.57 (d, J=7.6 Hz, 1H), 7.81 (d, J=7.6 Hz, 1H), 7.53 (t, J=7.8 Hz, 1H), 7.23 (s, 1H), 6.64 (s, 1H), 6.48 (s, 1H), 5.79 (s, 2H), 4.17 (t, J=8.4 Hz, 2H), 3.07 (t, J=8.4 Hz, 2H), 2.59 (s, 3H).

EXAMPLE 34: To a solution of 4-amino-1-((4-methyl-1-oxo-1,2-dihydroisoquinolin-5-yl)sulfonyl)indoline-6-carbonitrile (20 mg, 52.57 μmol, 1 eq) in DMF (2 mL) was added pyridine (12.48 mg, 157.72 μmol, 12.73 μL, 3 eq) and MeI (74.62 mg, 525.74 μmol, 32.73 μL, 10 eq). Then the mixture was stirred at 25° C. for 12 hr. The reaction mixture was concentrated under reduced pressure to give a residue. The residue was purified by prep-HPLC (column: Waters Xbridge BEH C18 100×25 mm×5 m; mobile phase: [water (10 mM NH₄HCO₃)-ACN]; B %: 30%-60%, 8 min). 4-(Dimethylamino)-1-((4-methyl-1-oxo-1,2-dihydroisoquinolin-5-yl)sulfonyl)indoline-6-carbonitrile (2.1 mg, 5.09 μmol, 9.68% yield, 99% purity) was obtained as a white solid. LCMS (ESI+) m/z: 409.0.

¹H NMR (400 MHz, DMSO-d₆): δ 11.68 (br, 1H), 8.59 (d, J=7.6 Hz 1H), 7.86 (d, J=7.6 Hz, 1H), 7.53 (t, J=8 Hz, 1H), 7.24 (s, 1H), 6.93 (s, 1H), 6.78 (s, 1H), 4.17 (t, J=8.4 Hz, 2H), ~3.05 (2H, mixed with solvent peak), 2.87 (s, 6H), 2.61 (s, 3H).

Examples 35, 36 & 37

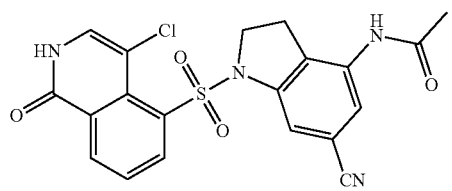 [SMILES: CC(=O)Nc1cc(C#N)cc2c1CCN2S(=O)(=O)c1cccc2c(=O)[nH]cc(Cl)c12]

N-(1-((4-chloro-1-oxo-1,2-dihydroisoquinolin-5-yl)sulfonyl)-6-cyanoindolin-4-yl)acetamide

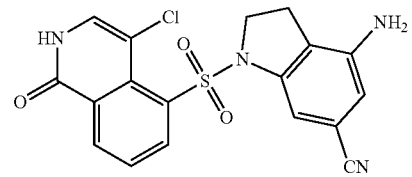 [SMILES: N#Cc1cc(N)c2c(c1)N(S(=O)(=O)c1cccc3c(=O)[nH]cc(Cl)c13)CC2]

4-amino-1-((4-chloro-1-oxo-1,2-dihydroisoquinolin-5-yl)sulfonyl)indoline-6-carbonitrile

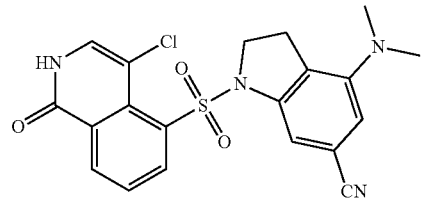 [SMILES: CN(C)c1cc(C#N)cc2c1CCN2S(=O)(=O)c1cccc2c(=O)[nH]cc(Cl)c12]

1-((4-chloro-1-oxo-1,2-dihydroisoquinolin-5-yl)sulfonyl)-4-(dimethylamino)indoline-6-carbonitrile

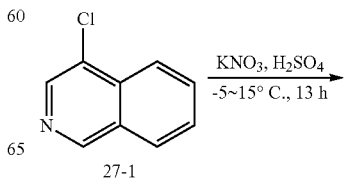

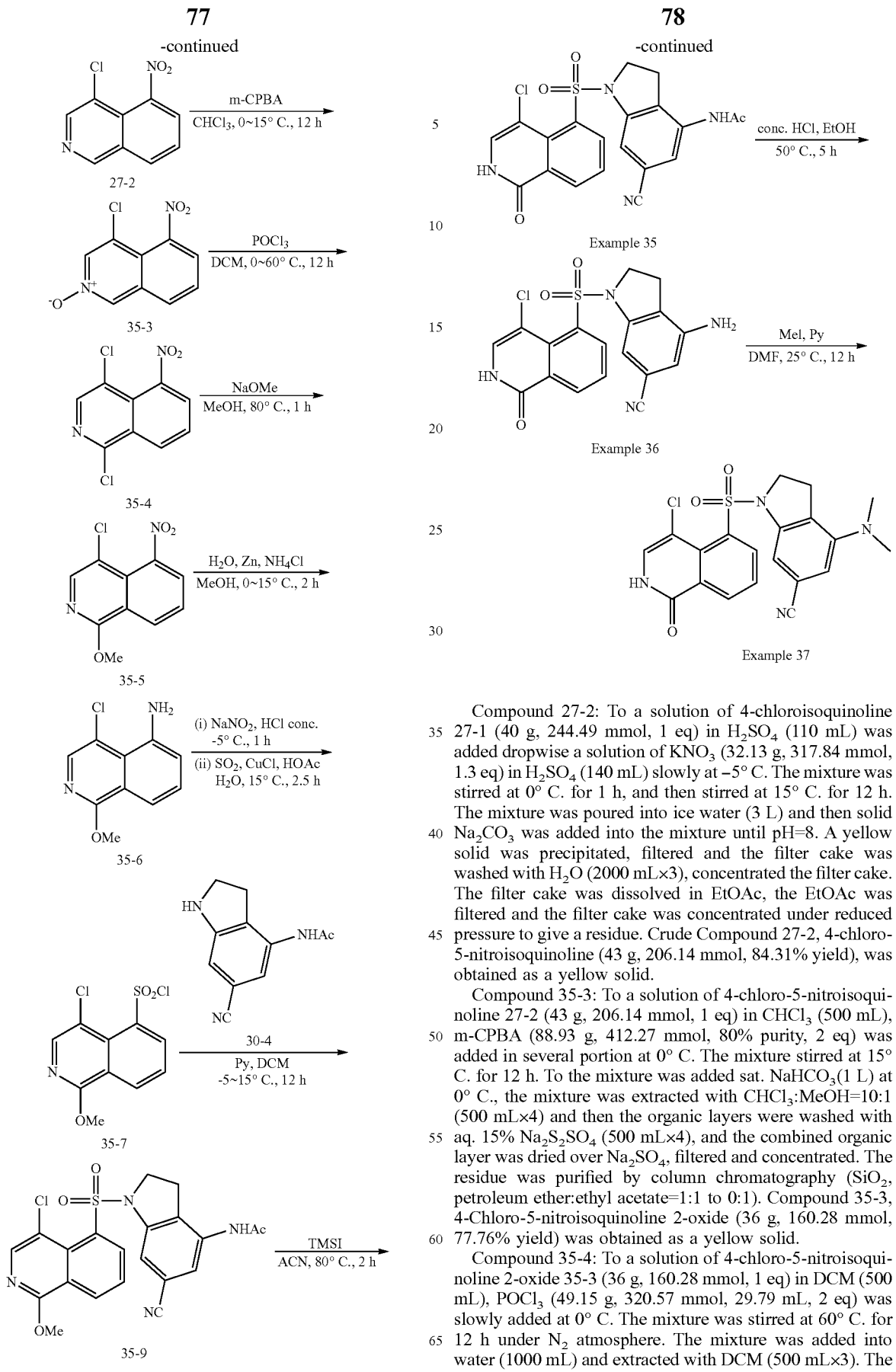

Compound 27-2: To a solution of 4-chloroisoquinoline 27-1 (40 g, 244.49 mmol, 1 eq) in $H_2SO_4$ (110 mL) was added dropwise a solution of $KNO_3$ (32.13 g, 317.84 mmol, 1.3 eq) in $H_2SO_4$ (140 mL) slowly at −5° C. The mixture was stirred at 0° C. for 1 h, and then stirred at 15° C. for 12 h. The mixture was poured into ice water (3 L) and then solid $Na_2CO_3$ was added into the mixture until pH=8. A yellow solid was precipitated, filtered and the filter cake was washed with $H_2O$ (2000 mL×3), concentrated the filter cake. The filter cake was dissolved in EtOAc, the EtOAc was filtered and the filter cake was concentrated under reduced pressure to give a residue. Crude Compound 27-2, 4-chloro-5-nitroisoquinoline (43 g, 206.14 mmol, 84.31% yield), was obtained as a yellow solid.

Compound 35-3: To a solution of 4-chloro-5-nitroisoquinoline 27-2 (43 g, 206.14 mmol, 1 eq) in $CHCl_3$ (500 mL), m-CPBA (88.93 g, 412.27 mmol, 80% purity, 2 eq) was added in several portion at 0° C. The mixture stirred at 15° C. for 12 h. To the mixture was added sat. $NaHCO_3$(1 L) at 0° C., the mixture was extracted with $CHCl_3$:MeOH=10:1 (500 mL×4) and then the organic layers were washed with aq. 15% $Na_2S_2SO_4$ (500 mL×4), and the combined organic layer was dried over $Na_2SO_4$, filtered and concentrated. The residue was purified by column chromatography ($SiO_2$, petroleum ether:ethyl acetate=1:1 to 0:1). Compound 35-3, 4-Chloro-5-nitroisoquinoline 2-oxide (36 g, 160.28 mmol, 77.76% yield) was obtained as a yellow solid.

Compound 35-4: To a solution of 4-chloro-5-nitroisoquinoline 2-oxide 35-3 (36 g, 160.28 mmol, 1 eq) in DCM (500 mL), $POCl_3$ (49.15 g, 320.57 mmol, 29.79 mL, 2 eq) was slowly added at 0° C. The mixture was stirred at 60° C. for 12 h under $N_2$ atmosphere. The mixture was added into water (1000 mL) and extracted with DCM (500 mL×3). The organic layer was washed with sat. $NaHCO_3$(800 mL×3) and brine (1500 mL), then dried over Na$_2$SO$_4$, filtered and concentrated. Crude Compound 35-4, 1,4-dichloro-5-nitroisoquinoline (26 g, 106.98 mmol, 66.74% yield), was obtained as a brown solid.

Compound 35-5: To a solution of 1,4-dichloro-5-nitroisoquinoline 35-4 (25 g, 102.86 mmol, 1 eq) in MeOH (150 mL), NaOMe (24.45 g, 113.15 mmol, 25% purity, 1.1 eq). The mixture was stirred at 80° C. for 1 h under N$_2$ atmosphere, filtered and the filter cake was concentrated under reduced pressure to give Compound 36-5, 4-chloro-1-methoxy-5-nitroisoquinoline (16 g, 67.05 mmol, 65.19% yield), was obtained as a brown solid.

Compound 35-6: To a solution of 4-chloro-1-methoxy-5-nitroisoquinoline 35-5 (15.9 g, 66.63 mmol, 1 eq) and NH$_4$Cl (35.64 g, 666.31 mmol, 10 eq) in MeOH (200 mL) and H$_2$O (40 mL), Zn (43.57 g, 666.31 mmol, 10 eq) was slowly added at 0° C. The mixture was stirred at 15° C. for 2 hr, filtered and the filtrate was concentrated under reduced pressure to give a residue. The residue was added to H$_2$O (50 mL) and the mixture was extracted with EtOAc (500 mL×4). The combined organic layers were washed with brine (2000 mL×1), dried over Na$_2$SO$_4$, filtered and concentrated under reduced pressure to give a residue. The residue was washed with petroleum ether:ethyl acetate=30:1 (930 mL), filtered and the filter cake was dried under reduced pressure. Crude Compound 35-6, 4-chloro-1-methoxyisoquinolin-5-amine (11.2 g, 53.68 mmol, 80.56% yield), was obtained as a white solid.

Preparation of Solution A: To a solution of 4-chloro-1-methoxyisoquinolin-5-amine 35-6 (0.2 g, 958.57 μmol, 1 eq) in HCl (8 mL), a solution of NaNO$_2$ (99.21 mg, 1.44 mmol, 1.5 eq) in H$_2$O (1 mL) at −5° C. was added. The mixture was stirred at −5° C. for 1 h.

Preparation of Solution B: SO$_2$ was bubbled into a solution of CuCl (23.72 mg, 239.64 mol, 5.73 μL, 0.25 eq) in AcOH (5 mL) and H$_2$O (1 mL) at 0° C. for 30 minutes at 15 psi.

Compound 35-7: Solution A was transferred into Solution B and the mixture was stirred at 15° C. for 2 hr. The reaction mixture was quenched by addition to ice water (20 mL) at 0° C., and then extracted with DCM (30 mL×3). The combined organic layers were washed with brine (100 mL×2), dried over Na$_2$SO, filtered and concentrated under reduced pressure to give a residue. Compound 35-7, 4-Chloro-1-methoxyisoquinoline-5-sulfonyl chloride (300 mg, crude), was obtained as a yellow solid.

Compound 35-9: To a mixture of N-(6-cyanoindolin-4-yl)acetamide (Compound 30-4; 500 mg, 2.48 mmol, 1.3 eq) and pyridine (453.57 mg, 5.73 mmol, 462.83 μL, 3 eq) was added dropwise a solution of 4-chloro-1-methoxyisoquinoline-5-sulfonyl chloride 35-7 (1.27 g, 1.91 mmol, 1 eq) in DCM (5 mL) at −5° C. The mixture was degassed and purged with N$_2$ 3 times, and the mixture was stirred at 15° C. for 12 hr under N$_2$ atmosphere. The reaction mixture was concentrated under reduced pressure to give a residue. Crude Compound 35-9, N-(1-((4-chloro-1-methoxyisoquinolin-5-yl)sulfonyl)-6-cyanoindolin-4-yl)acetamide (1.5 g, crude), was obtained as a red solid and used into next step without further purification.

EXAMPLE 35: A mixture of N-(1-((4-chloro-1-methoxy-isoquinolin-5-yl)sulfonyl)-6-cyanoindolin-4-yl)acetamide 35-9 (100 mg, 218.87 μmol, 1 eq) and TMSI (218.96 mg, 1.09 mmol, 148.96 μL, 5 eq) in ACN (10 mL) was stirred at 80° C. for 2 hr under N$_2$ atmosphere. The reaction mixture was quenched by addition to H$_2$O (20 mL) at 0° C., and then extracted with EtOAc (40 mL×2). The combined organic layers were washed with brine (80 mL), dried over Na$_2$SO$_4$, filtered and concentrated under reduced pressure to give a residue. The residue was purified by prep-TLC (SiO$_2$, DCM:MeOH=10:1). Then the residue was re-purified by prep-HPLC (column: Waters Xbridge BEH C18 100×25 mm×5 m; mobile phase: [water (10 mM NH$_4$HCO$_3$)-ACN]; B %: 20%-50%, 8 min). EXAMPLE 35, N-(1-((4-Chloro-1-oxo-1,2-dihydroisoquinolin-5-yl)sulfonyl)-6-cyanoindolin-4-yl)acetamide (1.9 mg, 4.08 μmol, 1.86% yield, 95.1% purity), was obtained as a white solid. LCMS (ESI+) m/z: 443.0.

$^1$H NMR (400 MHz, DMSO-d$_6$): δ 9.73 (s, 1H), 8.57 (d, J=7.6 Hz, 1H), 8.01 (d, J=8 Hz, 1H), 7.91 (s, 1H), 7.66 (s, 1H), 7.63 (t, J=7.6 Hz, 1H), 6.98 (s, 1H), 4.19 (t, J=8.4 Hz, 2H), −3.20 (2H, mixed with solvent peak), 2.14 (s, 3H).

EXAMPLE 36: A solution of N-(1-((4-chloro-1-oxo-1,2-dihydroisoquinolin-5-yl)sulfonyl)-6-cyanoindolin-4-yl)acetamide EXAMPLE 35 (16 mg, 36.13 μmol, 1 eq) in conc. HCl (3 mL) and EtOH (3 mL) was stirred at 50° C. for 5 hr. To the mixture was added saturated Na$_2$CO$_3$ solution until pH=8 at 0° C., and the mixture was extracted with EtOAc (40 mL×5). The combined organic layers were washed with brine (200 mL), dried over Na$_2$SO$_4$, filtered and concentrated under reduced pressure to give a residue. The residue was purified by prep-HPLC (column: Waters Xbridge BEH C18 100×25 mm×5 μm; mobile phase: [water (10 mM NH$_4$HCO$_3$)-ACN]; B %: 20%-40%, 8 min). EXAMPLE 36, 4-amino-1-((4-chloro-1-oxo-1,2-dihydroisoquinolin-5-yl)sulfonyl)indoline-6-carbonitrile (1.6 mg, 97.6% purity), was obtained as a white solid. LCMS (ESI+) m/z: 400.9.

$^1$H NMR (400 MHz, DMSO-d$_6$): δ 12.04 (br, 1H), 8.56 (d, J=8 Hz, 1H), 7.92 (d, J=7.6 Hz, 1H), 7.65~7.61 (m, 2H), 6.63 (s, 1H), 6.45 (s, 1H), 5.77 (s, 2H), 4.15 (t, J=8.4 Hz, 2H), 3.05 (t, J=8.4 Hz, 2H).

EXAMPLE 37: To a solution of 4-amino-1-((4-chloro-1-oxo-1,2-dihydroisoquinolin-5-yl)sulfonyl)indoline-6-carbonitrile EXAMPLE 36 (20 mg, 49.90 μmol, 1 eq) in DMF (2.5 mL) was added pyridine (39.47 mg, 498.95 μmol, 40.27 μL, 10 eq) and MeI (141.64 mg, 997.91 mol, 62.12 μL, 20 eq). The mixture was stirred at 25° C. for 12 hr. The mixture was concentrated under reduced pressure to give a residue. The residue was purified by prep-HPLC (column: Waters Xbridge BEH C18 100×25 mm×5 μm; mobile phase: [water (10 mM NH$_4$HCO$_3$)-ACN]; B %: 30%-60%, 8 min). EXAMPLE 37, 1-((4-Chloro-1-oxo-1,2-dihydroisoquinolin-5-yl)sulfonyl)-4-(dimethylamino)indoline-6-carbonitrile (3.1 mg, 7.08 tmol, 14.20% yield, 98% purity), was obtained as a white solid. LCMS (ESI+) m/z: 429.1.

$^1$H NMR (400 MHz, DMSO-d$_6$): δ 12.05 (br, 1H), 8.55 (d, J=8 Hz, 1H), 7.94 (d, J=8 Hz, 1H), 7.65 (s, 1H), 7.63 (t, J=8 Hz, 1H), 6.9 2 (s, 1H), 6.74 (s, 1H), 4.13 (t, J=8.4 Hz, 2H), ~3.33 (2H, mixed with solvent peak), 2.85 (s, 6H).

Example 38

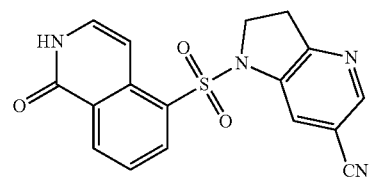

81

1-((1-oxo-1,2-dihydroisoquinolin-5-yl)sulfonyl)-2,3-dihydro-1H-pyrrolo[3,2-b]pyridine-6-carbonitrile

82

1-((4-methyl-1-oxo-1,2-dihydroisoquinolin-5-yl)sulfonyl)-2,3-dihydro-1H-pyrrolo[3,2-b]pyridine-6-carbonitrile

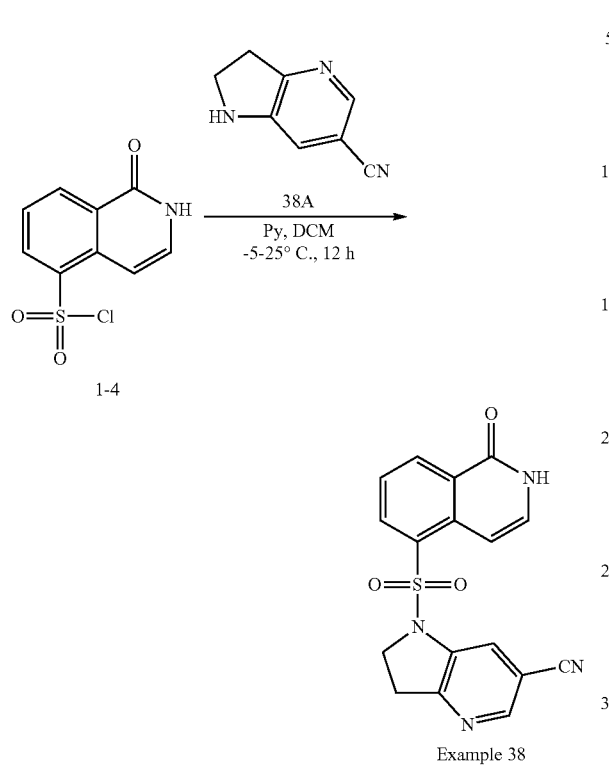

Example 38

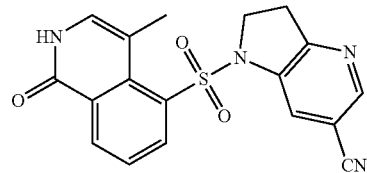 [SMILES: Cc1c[nH]c(=O)c2cccc(S(=O)(=O)N3CCc4ncc(C#N)cc43)c12]

Example 39

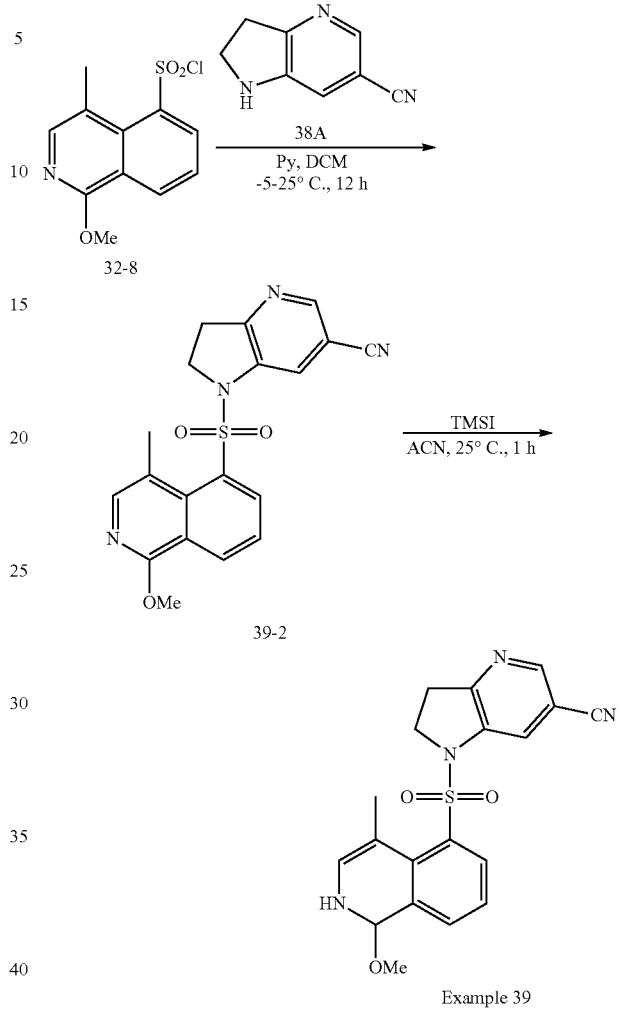

Example 39

EXAMPLE 38: To a mixture of 2,3-dihydro-1H-pyrrolo[3,2-b]pyridine-6-carbonitrile 38A (21.45 mg, 147.74 μmol, 1.2 eq) and pyridine (29.22 mg, 369.36 μmol, 29.81 μL, 3 eq), was added dropwise a solution of 1-oxo-2H-isoquinoline-5-sulfonyl chloride 1-4 (30 mg, 123.12 μmol, 1 eq) in DCM (3 mL) at −5° C. The mixture was degassed and purged with $N_2$ 3 times, and the mixture was stirred at 25° C. for 12 hr under $N_2$ atmosphere. The reaction mixture was concentrated under reduced pressure to give a residue. The crude product was taken up in MeOH (2 mL) at 25° C. for 10 min, filtered concentrated under reduced pressure to give a residue. The residue was purified by prep-HPLC (column: Welch Ultimate AQ-C18 150×30 mm×5 M; mobile phase: [water(0.1% TFA)-ACN];B %: 35%-65%,12 min). EXAMPLE 38, 1-[(1-oxo-2H-isoquinolin-5-yl)sulfonyl]-2,3-dihydropyrrolo[3,2-b]pyridine-6-carbonitrile (15 mg, 41.51 μmol, 33.71% yield, 97.5% purity), was obtained as a white solid. LCMS (ESI+) m/z: 353.0.

$^1$H NMR (400 MHz, DMSO-$d_6$): δ 11.71 (br, 1H), 8.59-8.52 (m, 2H), 8.46 (d, J=7.6 Hz, 1H), 7.90 (d, J=2 Hz, 1H), 7.64 (t, J=7.6 Hz, 1H), 7.39 (t, J=7.6 Hz, 1H), 7.11 (d, J=7.6 Hz, 1H), 4.08 (t, J=8.4 Hz, 2H), 3.22 (t, J=8.8 Hz, 2H).

Compound 39-2: To a mixture of 2,3-dihydro-1H-pyrrolo[3,2-b]pyridine-6-carbonitrile 38A (19.23 mg, 132.49 μmol, 1.2 eq) and pyridine (26.20 mg, 331.22 μmol, 26.73 μL, 3 eq) was added dropwise a solution of 1-methoxy-4-methyl-isoquinoline-5-sulfonyl chloride 32-8 (30 mg, 110.41 μmol, 1 eq) in DCM (2 mL) at −5° C. The mixture was degassed and purged with $N_2$ 3 times, and the mixture was stirred at 25° C. for 12 hr under $N_2$ atmosphere. The reaction mixture was concentrated under reduced pressure to remove DCM (2 mL). The residue was purified by prep-TLC (SiO$_2$, petroleum ether:ethyl acetate=1:1). Compound 39-2 1-[(1-methoxy-4-methyl-5-isoquinolyl)sulfonyl]-2,3-dihydropyrrolo[3,2-b]pyridine-6-carbonitrile (15 mg, 39.43 μmol, 35.71% yield), was obtained as a white solid.

EXAMPLE 39: A mixture of 1-[(1-methoxy-4-methyl-5-isoquinolyl)sulfonyl]-2,3-dihydropyrrolo[3,2-b]pyridine-6-carbonitrile 39-2 (15 mg, 39.43 μmol, 1 eq) and TMSI (31.56 mg, 157.72 μmol, 21.47 μL, 4 eq) in ACN (2 mL) was stirred at 25° C. for 1 hr under $N_2$ atmosphere. The reaction mixture was quenched by addition of H$_2$O (5 mL) at 0° C., and then extracted with EtOAc (5 mL×2). The combined organic layers were washed with brine (5 mL), dried over Na$_2$SO$_4$, filtered and concentrated under reduced pressure to give a residue. The residue was purified by prep-HPLC (column: Waters Xbridge Prep OBD C18 150×40 mm×10 μm; mobile phase: [water(0.04% NH3H2O+10 mM NH4HCO3)-ACN];B %: 25%-55%,8 min).

EXAMPLE 39, 1-[(4-methyl-1-oxo-2H-isoquinolin-5-yl)sulfonyl]-2,3-dihydropyrrolo[3,2-b]pyridine-6-carbonitrile (3.4 mg, 9.28 μmol, 23.53% yield, 100% purity), was obtained as a white solid. LCMS (ESI+) m/z: 367.0.

1H NMR (400 MHz, DMSO-$d_6$): δ 11.72 (br, 1H), 8.62~8.57 (m, 2H), 8.02 (d, J=2.4 Hz, 1H), 7.59~7.51 (m, 2H), 7.25 (s, 1H), 4.23 (t, J=8.8 Hz, 2H), 3.49 (t, J=8.8 Hz, 2H), 2.59 (s, 3H).

Example 40

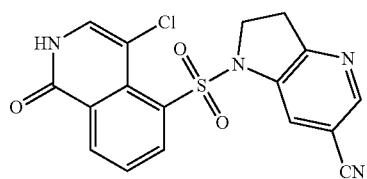 [SMILES: N#Cc1cnc2c(c1)N(S(=O)(=O)c1cccc3c(=O)[nH]cc(Cl)c13)CC2]

1-((4-chloro-1-oxo-1,2-dihydroisoquinolin-5-yl)sulfonyl)-2,3-dihydro-1H-pyrrolo[3,2-b]pyridine-6-carbonitrile

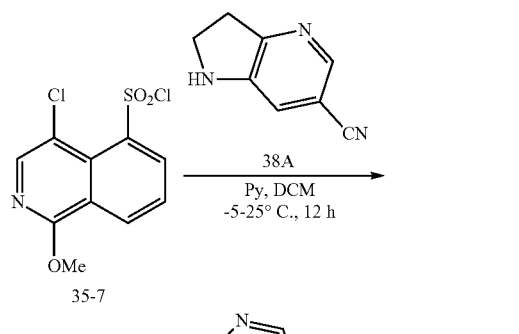

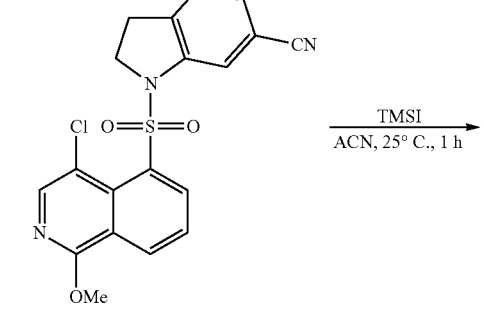

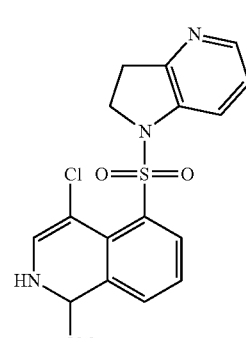

Example 40

Compound 40-2: To a mixture of 2,3-dihydro-1H-pyrrolo[3,2-b]pyridine-6-carbonitrile (17.89 mg, 123.23 μmol, 1.2 eq) 38A and pyridine (24.37 mg, 308.07 μmol, 24.87 μL, 3 eq) was added dropwise a solution of 4-chloro-1-methoxy-isoquinoline-5-sulfonyl chloride 35-7 (30 mg, 102.69 μmol, 1 eq) in DCM (2 mL) at −5° C. The mixture was degassed and purged with $N_2$ 3 times, and the mixture was stirred at 25° C. for 12 hr under $N_2$ atmosphere. LC-MS showed ~50% of desired compound was detected. The reaction mixture was concentrated under reduced pressure to remove DCM (2 mL). The residue was purified by prep-TLC (SiO$_2$, PE: EA=1:1). Compound 40-2, 1-[(4-chloro-1-methoxy-5-isoquinolyl) sulfonyl]-2,3-dihydropyrrolo[3,2-b]pyridine-6-carbonitrile (30 mg, 74.84 μmol, 72.88% yield), was obtained as a white solid.

EXAMPLE 40: To a mixture of 1-[(4-chloro-1-methoxy-5-isoquinolyl)sulfonyl]-2,3-dihydropyrrolo[3,2-b]pyridine-6-carbonitrile 40-2 (30 mg, 74.84 μmol, 1 eq) and TMSI (59.90 mg, 299.37 μmol, 40.75 μL, 4 eq) in acetonitrile (2 mL) was stirred at 25° C. for 1 hr under $N_2$ atmosphere. The reaction mixture was quenched by addition of $H_2O$ (4 mL) at 0° C., and then extracted with EtOAc (4 mL×2). The combined organic layers were washed with brine (8 mL), dried over Na$_2$SO$_4$, filtered and concentrated under reduced pressure to give a residue. The residue was purified by prep-HPLC (column: Welch Ultimate AQ-C18 150×30 mm×5 μm; mobile phase: [water(0.1% TFA)-ACN];B %: 15%-45%,12 min). EXAMPLE 40, 1-[(4-chloro-1-oxo-2H-isoquinolin-5-yl) sulfonyl]-2,3-dihydropyrrolo[3,2-b]pyridine-6-carbonitrile (7 mg, 17.55 μmol, 23.45% yield, 97% purity), was obtained as a yellow solid. LCMS (ESI+) m/z: 386.9.

Example 41

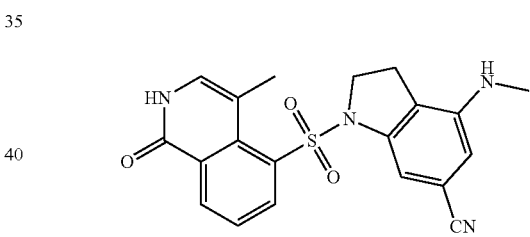

1-(4-methyl-1-oxo-1,2-dihydroisoquinolin-5-yl)sulfonyl)-4-(methylamino)indoline-6-carbonitrile

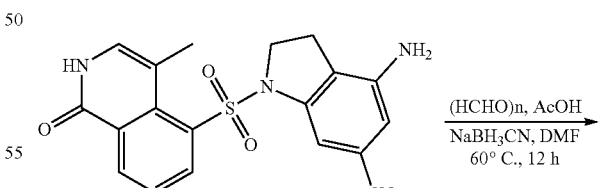

EXAMPLE 33

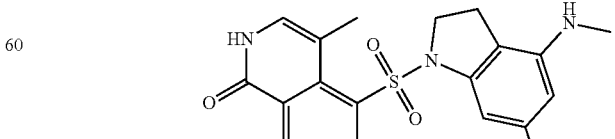

EXAMPLE 41

EXAMPLE 41: A mixture of 4-amino-1-[(4-methyl-1-oxo-2H-isoquinolin-5-yl)sulfonyl]indoline-6-carbonitrile (70 mg, 184 µmol, 1 eq), (HCHO)$_n$ (11 mg, 368.0 µmol, 2 eq), NaBH$_3$CN (23 mg, 368.0 µmol, 2 eq), glacial acetic acid (22 mg, 368.01 µmol, 21 µL, 2 eq) in DMF (1 mL) was stirred at 60° C. for 12 hr. under N$_2$ atmosphere. The reaction mixture was added saturated NaHCO$_3$(10 mL) and extracted with ethyl acetate (10 mL×3). The combined organic phase was dried with anhydrous Na$_2$SO$_4$, filtered and concentrated under reduced pressure. The residue was purified by prep-HPLC (column: Phenomenex luna C18 80×40 mm×3 µm; mobile phase: [water (0.04% HCl)-ACN]; B %: 37%-57%, 7 min) to give 4-(methylamino)-1-[(4-methyl-1-oxo-2H-isoquinolin-5-yl)sulfonyl]indoline-6-carbonitrile EXAMPLE 41 (5 mg, 13.2 µmol, 7.2% yield). Physical appearance: yellow solid. LCMS (ESI+) m/z: 395.0. $^1$H NMR (400 MHz, DMSO-d$_6$): δ 11.71 (br, 1H), 8.58 (d, J=8 Hz, 1H), 7.8 (d, J=8 Hz, 1H), 7.53 (t, J=8 Hz, 1H), 7.24 (d, J=5.2 Hz, 1H), 6.61 (s, 1H), 6.57 (s, 1H), 4.20 (t, J=8.4 Hz, 2H), 3.09 (t, J=8.8 Hz, 2H), 2.79 (s, 3H), 2.60 (s, 3H)

Example 42

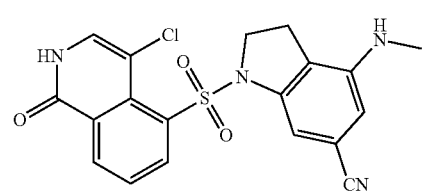 [SMILES: CNc1cc(C#N)cc2c1CCN2S(=O)(=O)c1cccc2c(=O)[nH]cc(Cl)c12]

1-((4-chloro-1-oxo-1,2-dihydroisoquinolin-5-yl)sulfonyl)-4-(methylamino)indoline-6-carbonitrile

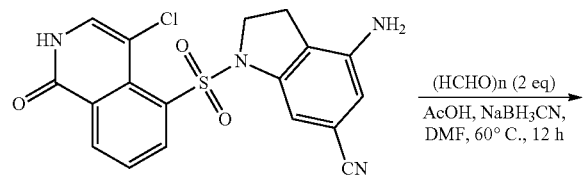

Example 36

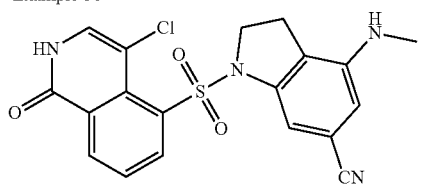

Example 42

EXAMPLE 42: A mixture of 4-amino-1-[(4-chloro-1-oxo-2H-isoquinolin-5-yl)sulfonyl]indoline-6-carbonitrile Example 36 (80 mg, 200 µmol, 1 eq), (HCHO)$_n$ (12 mg, 400 µmol, 2 eq), NaBH$_3$CN (25 mg, 400 µmol, 2 eq), glacial acetic acid (24 mg, 400 µmol, 23 µL, 2 eq) in DMF (1 mL) was stirred at 60° C. for 12 hr. The reaction mixture was added to saturated NaHCO$_3$(10 mL) and extracted with ethyl acetate (10 mL×3). The combined organic phase was dried with anhydrous Na$_2$SO$_4$, filtered and concentrated under reduced pressure. The residue was purified by prep-HPLC (column: Xtimate C18 100×30 mm×3 µm; mobile phase: [water (0.04% HCl)-ACN]; B %: 29%-49%, 9 min) to get 1-[(4-chloro-1-oxo-2H-isoquinolin-5-yl)sulfonyl]-4-(methylamino)indoline-6-carbonitrile, EXAMPLE 42 (18 mg, 42 µmol, 21% yield). Physical appearance: yellow solid. LCMS (ESI+) m/z: 415.0. $^1$H NMR (400 MHz, DMSO-d$_6$): δ 12.09 (br, 1H), 8.54 (d, J=8 Hz, 1H), 7.89 (d, J=8 Hz, 1H), 7.63-7.59 (m, 2H), 6.58 (s, 1H), 6.53 (s, 1H), 4.15 (t, J=8.8 Hz, 2H), 3.05 (t, J=8.8 Hz, 2H), 2.76 (s, 3H)

Example 43

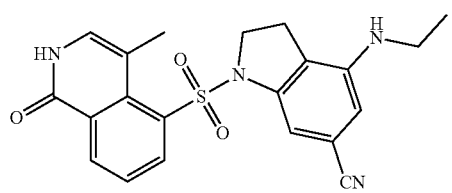 [SMILES: CCNc1cc(C#N)cc2c1CCN2S(=O)(=O)c1cccc2c(=O)[nH]cc(C)c12]

4-(ethyl amino)-1-((4-methyl-1-oxo-1,2-dihydroisoquinolin-5-yl)sulfonyl)indoline-6-carbonitrile

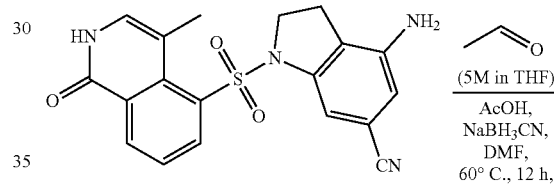

Example 33

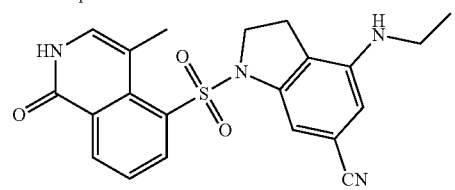

Example 43

EXAMPLE 43: A mixture of 4-amino-1-[(4-methyl-1-oxo-2H-isoquinolin-5-yl)sulfonyl]indoline-6-carbonitrile, Example 33 (50 mg, 131 µmol, 1 eq), acetaldehyde (5 M in THF, 395 µL, 15 eq), NaBH$_3$CN (25 mg, 394 µmol, 3 eq), glacial acetic acid (24 mg, 395 µmol, 23 µL, 3 eq) in DMF (1 mL) was stirred at 60° C. for 12 hr. in a sealed tube. The reaction mixture was added to sat. NaHCO$_3$(40 mL) and extracted with ethyl acetate (40 mL×3). The combined organic phase was dried with anhydrous Na$_2$SO$_4$, filtered and concentrated under reduced pressure. The residue was purified by prep-HPLC (column: Waters Xbridge Prep OBD C18 150×40 mm×10 µm; mobile phase: [water (10 mM NH$_4$HCO$_3$)-ACN]; B %: 35%-55%, 8 min) to give 4-(ethylamino)-1-[(4-methyl-1-oxo-2H-isoquinolin-5-yl)sulfonyl]indoline-6-carbonitrile IND-12202019-2 (4.3 mg, 8% yield). Physical appearance: yellow solid. LCMS (ESI+) m/z: 409.1. $^1$H NMR (400 MHz, DMSO-d$_6$): δ 8.57 (d, J=7.6 Hz, 1H), 7.81 (d, J=7.6 Hz, 1H), 7.53 (t, J=8 Hz, 1H), 7.23 (s, 1H), 6.65 (s, 1H), 6.54 (s, 1H), 5.84 (t, J=5.6 Hz, 1H), 4.18 (t, J=8.4 Hz, 2H), 3.22-3.12 (m, 2H), 3.09 (t, J=8.4 Hz, 2H), 2.59 (s, 3H), 1.19 (t, J=8.8 Hz, 3H)

Example 44

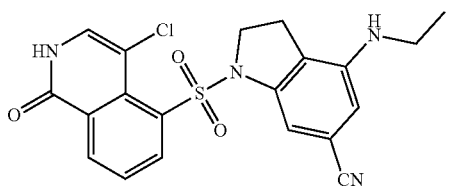 [SMILES: CCNc1cc(C#N)cc2c1CCN2S(=O)(=O)c1cccc2c(=O)[nH]cc(Cl)c12]

1-((4-chloro-1-oxo-1,2-dihydroisoquinolin-5-yl)sulfonyl)-4-(ethylamino)indoline-6-carbonitrile

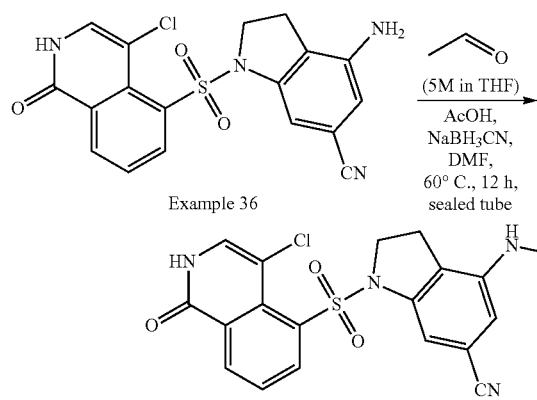

EXAMPLE 44: A mixture of 4-amino-1-[(4-chloro-1-oxo-2H-isoquinolin-5-yl)sulfonyl]indoline-6-carbonitrile Example 36 (80 mg, 200 µmol, 1 eq), acetaldehyde (5 M, 600 µL, 15 eq), NaBH$_3$CN (38 mg, 600 µmol, 3 eq), glacial acetic acid (36 mg, 600 µmol, 34.24 L, 3 eq) in DMF (1 mL) was stirred at 60° C. for 12 hr. in a sealed tube. The reaction mixture (combined with another batch of 20 mg scale) was added sat. NaHCO$_3$(20 mL) and extracted with ethyl acetate (20 mL×3). The combined organic phase was dried with anhydrous Na$_2$SO$_4$, filtered and concentrated under reduced pressure. The residue was purified by prep-HPLC (column: Waters Xbridge Prep OBD C18 150×40 mm×10 um; mobile phase: [water (10 mM NH$_4$HCO$_3$)-ACN]; B %: 35%-55%, 8 min) to get 1-[(4-chloro-1-oxo-2H-isoquinolin-5-yl)sulfonyl]-4-(ethylamino)indoline-6-carbonitrile, EXAMPLE 44 (17 mg, 16% yield). Physical appearance: yellow solid. LCMS (ESI+) m/z: 429.0. $^1$H NMR (400 MHz, DMSO-d$_6$): δ 11.90 (br, 1H), 8.55 (d, J=8 Hz, 1H), 7.91 (d, J=8 Hz, 1H), 7.64-7.60 (m, 2H), 6.63 (s, 1H), 6.51 (s, 1H), 5.82 (t, J=5.6 Hz, 1H), 4.15 (t, J=8.8 Hz, 2H), 3.21-3.12 (m, 2H), 3.09 (t, J=8.8 Hz, 2H), 1.18 (t, J=7.2 Hz, 3H)

Example 45

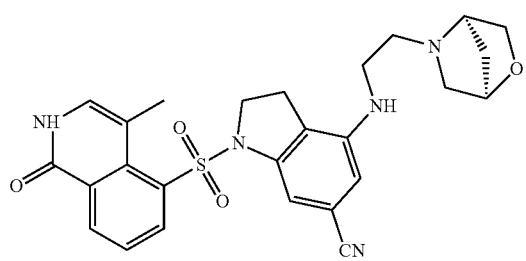 [SMILES: Cc1c[nH]c(=O)c2cccc(S(=O)(=O)N3CCc4c(NCCN5C[C@H]6C[C@@H]5CO6)cc(C#N)cc43)c12]

4-((2-((1R,4R)-2-oxa-5-azabicyclo[2.2.1]heptan-5-yl)ethyl)amino)-1-((4-methyl-1-oxo-1,2-dihydroisoquinolin-5-yl)sulfonyl)indoline-6-carbonitrile

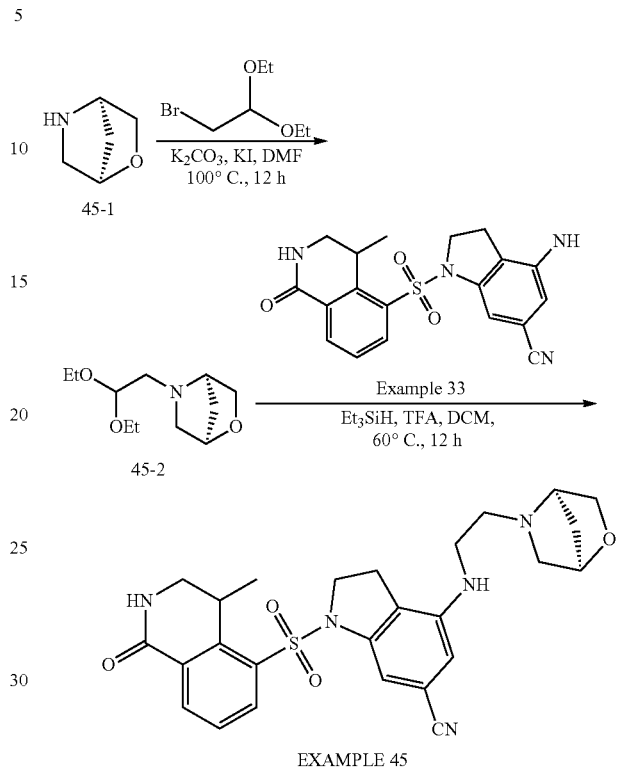

45-2: To a mixture of (1R,4R)-2-oxa-5-azabicyclo[2.2.1] heptane, 45-1 (1 g, 10.1 mmol, 1 eq) and 2-bromo-1,1-diethoxy-ethane (2.6 g, 13.11 mmol, 2 mL, 1.3 eq) in DMF (10 mL) was added K$_2$CO$_3$ (2.8 g, 20.2 mmol, 2 eq) and KI (167 mg, 1.01 mmol, 0.1 eq) under N$_2$. The mixture was stirred at 100° C. for 12 hours. The reaction mixture was filtered, and the filtrate was concentrated under reduced pressure. The residue was purified by column chromatography (SiO$_2$, Petroleum ether: Ethyl acetate=20:1 to 3:1) to give (1S,4S)-5-(2,2-diethoxyethyl)-2-oxa-5-azabicyclo [2.2.1]heptane 45-2 (1.73 g, 8.2 mmol, 81% yield). Physical appearance: yellow solid. LCMS (ESI+) m/z: 216.0. $^1$H NMR (400 MHz, CDCl$_3$): δ4.47 (t, J=5.2 Hz, 1H), 4.29 (s, 1H), 3.94 (d, J 7.6 Hz, 1H), 3.77-3.44 (m, 6H), 2.94 (dd, J=10 Hz, J=1.6 Hz, 1H), 2.74-2.63 (m, 2H), 2.54 (d, J=10 Hz, 1H), 1.77 (dd, J=9.6 Hz, J=2.0 Hz, 1H), 1.64 (d, J=9.6 Hz, 1H), 1.21-1.09 (m, 6H).

Example 45: To a mixture of 4-amino-1-[(4-methyl-1-oxo-2H-isoquinolin-5-yl)sulfonyl]indoline-6-carbonitrile Example 33 (80 mg, 210 µmol, 1 eq) and (1R,4R)-5-(2,2-diethoxyethyl)-2-oxa-5-azabicyclo[2.2.1]heptane 45-2 (136 mg, 631 µmol, 3 eq) in DCM (4 mL) was added TFA (336 mg, 3 mmol, 218 µL, 14 eq) and Et$_3$SiH (245 mg, 2.1 mmol, 336 µL, 10 eq). The mixture was stirred at 60° C. for 12 hr. The reaction mixture was added saturated NaHCO$_3$(15 mL) and extracted with DCM (15 mL×3). The combined organic phase was dried with anhydrous Na$_2$SO$_4$, filtered and concentrated under reduced pressure. The residue was purified by prep-HPLC (column: Xtimate C18 100×30 mm×3 µm; mobile phase: [water (0.04% HCl)-ACN]; B %: 14%-44%, 9 min) to give 1-[(4-methyl-1-oxo-2H-isoquinolin-5-yl)sulfonyl]-4-[2-[(1R,4R)-2-oxa-5-azabicyclo[2.2.1]heptan- 5-yl]ethylamino]indoline-6-carbonitrile, EXAMPLE 45 (5.14 mg, 9.5 μmol, 4.54% yield, 94% purity) as hydrochloride salt. Physical appearance: yellow solid. LCMS (ESI+) m/z: 506.1. $^1$H NMR (400 MHz, DMSO-d$_6$): δ 11.70 (d, J=5.6 Hz, 1H), 10.96 (m, ~0.5H), 10.44 (m, ~0.5H), 8.59 (d, J=8 Hz, 1H), 7.82 (d, J=8 Hz, 1H), 7.53 (t, J=8 Hz, 1H), 7.24 (d, J=5.6 Hz, 1H), 6.85-6.80 (m, 1H), 6.62 (s, 1H), 6.25-6.15 (m, 1H), 4.70-4.58 (m, 2H), 4.24-4.15 (m, 3H), 3.76-3.72 (m, 1H), 3.62-3.51 (m, 3H), 3.18 (t, J=8.8 Hz, 3H), 3.07-3.04 (m, 1H), 2.60 (s, 3H), 2.34-2.25 (m, 1H), 2.19-2.13 (m, 1H), 2.03-1.96 (m, 1H)

Example 46

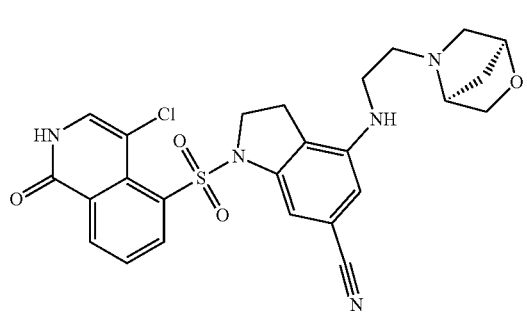 [SMILES: N#Cc1cc(NCCN2C[C@@H]3C[C@H]2CO3)c2c(c1)N(S(=O)(=O)c1cccc3c(=O)[nH]cc(Cl)c13)CC2]

4-((2-((1 S,4S)-2-oxa-5-azabicyclo[2.2.1]heptan-5-yl)ethyl)amino)-1-((4-chloro-1-oxo-1,2-dihydroisoquinolin-5-yl)sulfonyl)indoline-6-carbonitrile

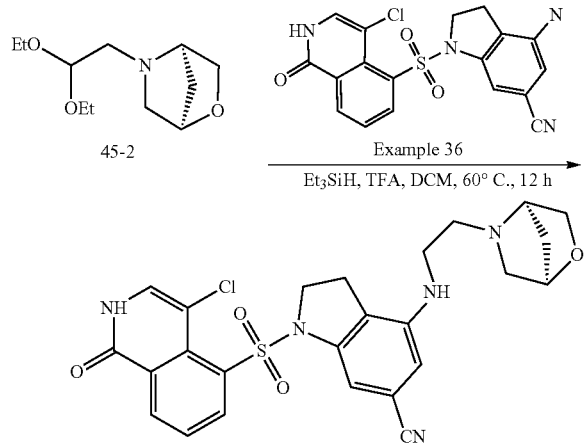

EXAMPLE 46

Example 46: To a mixture of 4-amino-1-[(4-chloro-1-oxo-2H-isoquinolin-5-yl)sulfonyl]indoline-6-carbonitrile Example 36 (80 mg, 210 μmol, 1 eq) and (1R,4R)-5-(2,2-diethoxyethyl)-2-oxa-5-azabicyclo[2.2.1]heptane 45-2 (136 mg, 631 μmol, 3 eq) in DCM (4 mL) was added TFA (336 mg, 2.94 mmol, 218 μL, 14 eq) and Et$_3$SiH (245 mg, 2.1 mmol, 336 μL, 10 eq). The mixture was stirred at 60° C. for 12 hr. The reaction mixture was added saturated NaHCO$_3$ (15 mL) and extracted with DCM (15 mL×3). The combined organic phase was dried with anhydrous Na$_2$SO$_4$, filtered and concentrated under reduced pressure. The residue was purified by prep-HPLC (column: Xtimate C18 100×30 mm×3 m; mobile phase: [water (0.04% HCl)-ACN]; B %: 14%-44%, 9 min) to give 1-[(4-methyl-1-oxo-2H-isoquinolin-5-yl)sulfonyl]-4-[2-[(1R,4R)-2-oxa-5-azabicyclo[2.2.1]heptan-5-yl]ethylamino]indoline-6-carbonitrile, EXAMPLE 46 (3.5 mg, 6.5 μmol, 3% yield, 91% purity) as hydrochloride salt. Physical appearance: yellow solid. LCMS (ESI+) m/z: 506.1.

Example 47

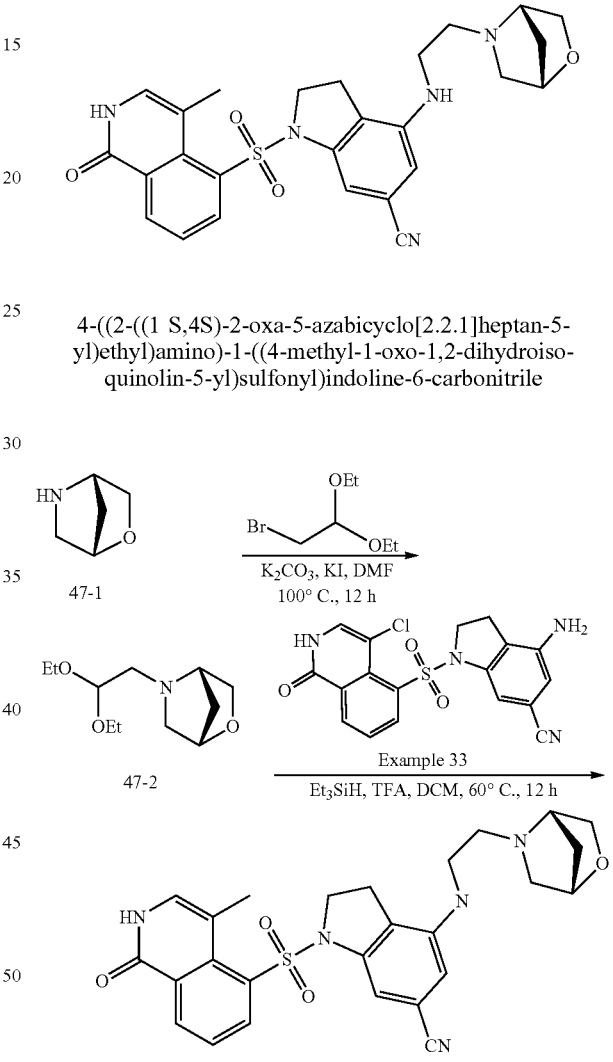

4-((2-((1 S,4S)-2-oxa-5-azabicyclo[2.2.1]heptan-5-yl)ethyl)amino)-1-((4-methyl-1-oxo-1,2-dihydroisoquinolin-5-yl)sulfonyl)indoline-6-carbonitrile

EXAMPLE 47

47-2: A mixture of (1S,4S)-2-oxa-5-azabicyclo[2.2.1]heptane 47-1 (2 g, 20.18 mmol, eq), 2-bromo-1,1-diethoxyethane (5.17 g, 26.23 mmol, 3.95 mL, 1.3 eq), K$_2$CO$_3$ (5.58 g, 40.35 mmol, 2 eq), KI (335 mg, 2.02 mmol, 0.1 eq) in DMF (20 mL) was degassed and purged with N$_2$ for 3 times, and then the mixture was stirred at 100° C. for 12 hr. under N$_2$ atmosphere. The reaction mixture was filtered, and the filtrate was concentrated under reduced pressure. The residue was purified by column chromatography (SiO$_2$, Petroleum ether: Ethyl acetate=20:1 to 3:1) to give (1S,4S)-5-(2,2-diethoxyethyl)-2-oxa-5-azabicyclo[2.2.1]heptane 47-2

(3.5 g, 16.26 mmol, 80.58% yield). Physical appearance: yellow oil. LCMS (ESI+) m/z: 216.0. $^1$H NMR (400 MHz, CDCl$_3$): δ4.53 (t, J=5.2 Hz, 1H), 4.29 (s, 1H), 4.01 (d, J=8.0 Hz, 1H), 3.72-3.52 (m, 6H), 3.00 (dd, J=10 Hz, J=1.6 Hz, 1H), 2.80-2.69 (m, 2H), 2.60 (d, J=10 Hz, 1H), 1.84 (dd, J=9.6 Hz, J=2.0 Hz, 1H), 1.70 (d, J=9.6 Hz, 1H), 1.21 (t, J=8.2 Hz, 6H).

Example 47: To a mixture of 4-amino-1-[(4-methyl-1-oxo-2H-isoquinolin-5-yl)sulfonyl]indoline-6-carbonitrile Example 33 (100 mg, 263 μmol, 1 eq), (1S,4S)-5-(2,2-diethoxyethyl)-2-oxa-5-azabicyclo[2.2.1]heptane 47-2 (170 mg, 790 μmol, 3 eq) in DCM (5 mL) was added TFA (420 mg, 3.68 mmol, 273 μL, 14 eq) and Et$_3$SiH (306 mg, 2.63 mmol, 420 μL, 10 eq), then the mixture was stirred at 60° C. for 12 hr. in a sealed tube. The reaction mixture was added sat. NaHCO$_3$(15 mL) and extracted with DCM (15 mL×3). The combined organic phase was dried with anhydrous Na$_2$SO$_4$, filtered and concentrated under reduced pressure. The residue was purified by prep-HPLC (column: Xtimate C18 100×30 mm×3 μm; mobile phase: [water (0.04% HCl)-ACN]; B %: 14%-34%, 9 min) to get 1-[(4-methyl-1-oxo-2H-isoquinolin-5-yl)sulfonyl]-4-[2-[(1S,4S)-2-oxa-5-azabicyclo[2.2.1]heptan-5-yl]ethylamino]indoline-6-carbonitrile EXAMPLE 47 (1.12 mg, 2.62 μmol, 1% yield). Physical appearance: yellow solid. LCMS (ESI+) m/z: 506.2. $^1$H NMR (400 MHz, DMSO-d$_6$): δ 11.70 (d, J=5.6 Hz, 1H), 10.98 (br, ~0.5H), 10.45 (br, ~0.5H), 8.58 (d, J=8 Hz, 1H), 7.81 (d, J=7.6 Hz, 1H), 7.52 (t, J=8 Hz, 1H), 7.24 (d, J=6 Hz, 1H), 6.83 (d, J=5.6 Hz, 1H), 6.61 (s, 1H), 6.25~6.15 (m, 1H), 4.69-4.58 (m, 2H), 4.23-4.14 (m, 3H), 3.77-3.72 (m, 1H), 3.60-3.50 (m, 3H), 3.17 (t, J=8.8 Hz, 3H), 3.07-3.03 (m, 1H), 2.60 (s, 3H), 2.36-2.28 (m, 1H), 2.19-2.09 (m, 1H), 2.02-1.92 (m, 1H)

Example 48

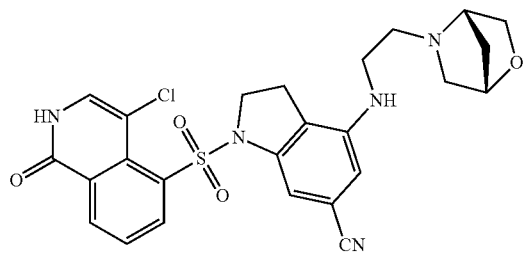 [SMILES: N#Cc1cc(NCCN2C[C@@H]3C[C@H]2CO3)c2c(c1)N(S(=O)(=O)c1cccc3c(=O)[nH]cc(Cl)c13)CC2]

4-((2-((1 S,4S)-2-oxa-5-azabicyclo[2.2.1]heptan-5-yl)ethyl)amino)-1-((4-chloro-1-oxo-1,2-dihydroisoquinolin-5-yl)sulfonyl)indoline-6-carbonitrile

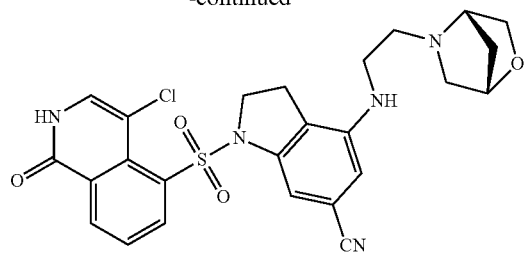

Example 48

Preparation of EXAMPLE 48: To a mixture of 4-amino-1-[(4-chloro-1-oxo-2H-isoquinolin-5-yl)sulfonyl]indoline-6-carbonitrile Example 36 (100 mg, 250 μmol, 1 eq), (1S, 4S)-5-(2,2-diethoxyethyl)-2-oxa-5-azabicyclo[2.2.1]heptane 47-2 (161 mg, 750 μmol, 3 eq) in DCM (5 mL) was added TFA (400 mg, 3.50 mmol, 258.60 μL, 14 eq) and Et$_3$SiH (290 mg, 2.5 mmol, 400 μL, 10 eq), then the mixture was stirred at 60° C. for 12 hr. in a sealed tube. The reaction mixture was added sat. NaHCO$_3$(15 mL) and extracted with DCM (15 mL×3). The combined organic phase was dried with anhydrous Na$_2$SO$_4$, filtered and concentrated under reduced pressure. The residue was purified by prep-HPLC (column: Xtimate C18 100×30 mm×3 μm; mobile phase: [water (0.04% HCl)-ACN]; B %: 14%-34%, 9 min) to get 1-[(4-chloro-1-oxo-2H-isoquinolin-5-yl)sulfonyl]-4-[2-[(1S,4S)-2-oxa-5-azabicyclo[2.2.1]heptan-5-yl]ethylamino]indoline-6-carbonitrile EXAMPLE 48 (3.33 mg, 6.33 μmol, 2.5% yield). Physical appearance: yellow solid. LCMS (ESI+) m/z: 526.1. $^1$H NMR (400 MHz, DMSO-d$_6$): δ 12.12 (br, 1H), 11.40 (br, ~0.5H), 10.94 (br, ~0.5H), 8.55 (d, J=8.8 Hz, 1H), 7.92 (d, J=8 Hz, 1H), 7.65-7.59 (m, 2H), 6.82 (d, J=6.4 Hz, 1H), 6.59 (d, J=4 Hz, 1H), 6.30-6.21 (m, 1H), 4.68-4.58 (m, 2H), 4.30-4.10 (m, 3H), 3.73-3.69 (m, 1H), 3.60-3.50 (m, 3H), 3.16 (t, J=8 Hz, 3H), 3.07-3.04 (m, 1H), 2.33-2.25 (m, 1H), 2.24-2.13 (m, 1H), 1.99-1.90 (m, 1H)

Example 49

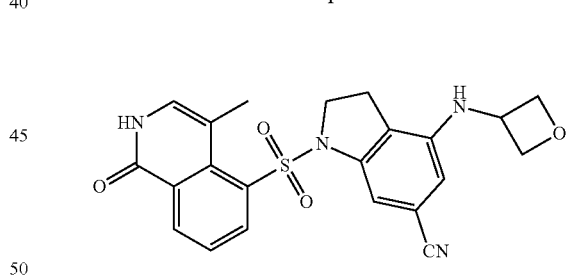

1-((4-methyl-1-oxo-1,2-dihydroisoquinolin-5-yl)sulfonyl)-4-(oxetan-3-ylamino)indoline-6-carbonitrile

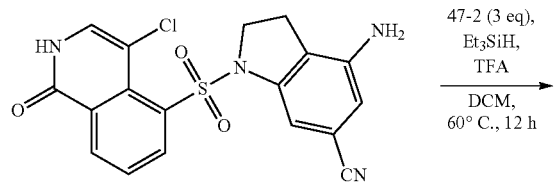

Example 36

47-2 (3 eq), Et$_3$SiH, TFA

DCM, 60° C., 12 h

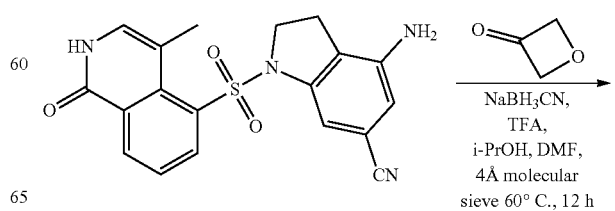

Example 33

NaBH$_3$CN, TFA, i-PrOH, DMF, 4Å molecular sieve 60° C., 12 h

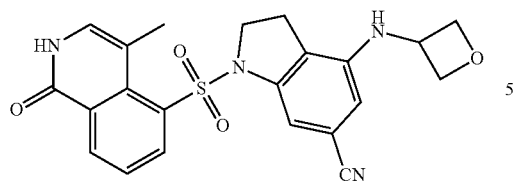

Example 49

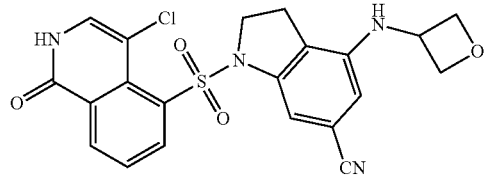

Example 50

EXAMPLE 49: A mixture of 4-amino-1-[(4-methyl-1-oxo-2H-isoquinolin-5-yl)sulfonyl]indoline-6-carbonitrile Example 33 (100 mg, 263 μmol, 1 eq), oxetan-3-one (380 mg, 5.3 mmol, 20 eq), NaBH$_3$CN (50 mg, 790 μmol, 3 eq), TFA (150 mg, 1.31 mmol, 97 μL, 5 eq) and 4 Å molecular sieve (20 mg, 250 μmol) in i-PrOH (5 mL) and DMF (5 mL) was stirred at 60° C. for 12 hr. under N$_2$ atmosphere. The reaction mixture was added sat. NaHCO$_3$(15 mL) and extracted with DCM (15 mL×3). The combined organic phase was dried with anhydrous Na$_2$SO$_4$, filtered and concentrated under reduced pressure. The residue was purified by prep-HPLC (column: Waters Xbridge Prep OBD C18 150×40 mm×10 m; mobile phase: [water (10 mM NH$_4$HCO$_3$)-ACN]; B %: 25%-45%, 8 min) to get 1-[(4-methyl-1-oxo-2H-isoquinolin-5-yl)sulfonyl]-4-(oxetan-3-ylamino)indoline-6-carbonitrile EXAMPLE 49 (21.1 mg, 48.3 μmol, 18% yield). Physical appearance: white solid. LCMS (ESI+) m/z: 437.0. $^1$H NMR (400 MHz, DMSO-d$_6$): δ 8.57 (dd, J=8 Hz, J=1.6 Hz, 1H), 7.83 (dd, J=7.6 Hz, J=1.2 Hz, 1H), 7.53 (t, J=8 Hz, 1H), 7.23 (s, 1H), 6.61 (s, 1H), 6.51 (d, J=6.4 Hz, 1H), 6.47 (s, 1H), 4.88 (t, J=6.4 Hz, 2H), 4.72-4.65 (m, 1H), 4.54 (t, J=6 Hz, 2H), 4.20 (t, J=8.8 Hz, 2H), 3.17 (t, J=8.8 Hz, 2H), 2.59 (s, 3H)

EXAMPLE 50: A mixture of 4-amino-1-[(4-chloro-1-oxo-2H-isoquinolin-5-yl)sulfonyl]indoline-6-carbonitrile Example 36 (100 mg, 249.48 μmol, 1 eq), oxetan-3-one (360 mg, 5 mmol, 20 eq), NaBH$_3$CN (47 mg, 750 μmol, 3 eq), TFA (142 mg, 1.25 mmol, 92 μL, 5 eq) and 4 Å molecular sieve (20 mg, 250 μmol) in i-PrOH (5 mL) and DMF (5 mL) was stirred at 60° C. for 12 hr. under N$_2$ atmosphere. The reaction mixture was added saturated NaHCO$_3$ solution (15 mL) and extracted with DCM (15 mL×3). The combined organic phase was dried with anhydrous Na$_2$SO$_4$, filtered and concentrated under reduced pressure. The residue was purified by prep-HPLC (column: Waters Xbridge Prep OBD C18 150×40 mm×10 μm; mobile phase: [water (10 mM NH$_4$HCO$_3$)-ACN]; B %: 25%-45%, 8 min) to get 1-[(4-chloro-1-oxo-2H-isoquinolin-5-yl)sulfonyl]-4-(oxetan-3-ylamino)indoline-6-carbonitrile EXAMPLE 50 (8.3 mg, 18 μmol, 7.3% yield). Physical appearance: white solid. LCMS (ESI+) m/z: 457.0. $^1$H NMR (400 MHz, DMSO-d$_6$): δ 8.57 (d, J=8 Hz, 1H), 7.92 (d, J=6.8 Hz, 1H), 7.66 (s, 1H), 7.60 (t, J=8 Hz, 1H), 6.58 (s, 1H), 6.50 (d, J=6.4 Hz, 1H), 6.45 (s, 1H), 4.87 (t, J=6.8 Hz, 2H), 4.70-4.65 (m, 1H), 4.53 (t, J=6 Hz, 2H), 4.17 (t, J=8.8 Hz, 2H), 3.14 (t, J=8.8 Hz, 2H) Indoline Reagents Indonline 2

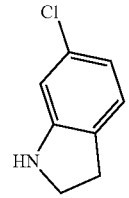

Example 50

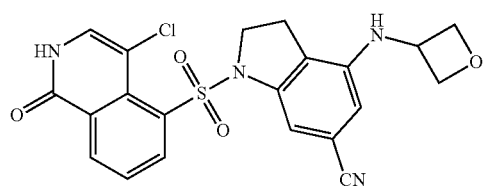 [SMILES: N#Cc1cc(NC2COC2)c2c(c1)N(S(=O)(=O)c1cccc3c(=O)[nH]cc(Cl)c13)CC2]

1-((4-chloro-1-oxo-1,2-dihydroisoquinolin-5-yl)sulfonyl)-4-(oxetan-3-ylamino)indoline-6-carbonitrile

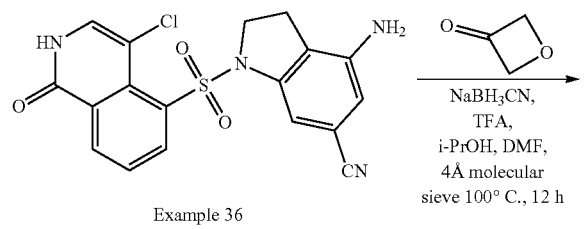

Example 36

6-Chloroindoline

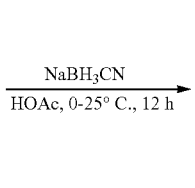 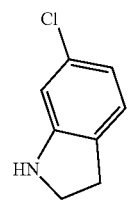

INDOLINE 2: To a mixture of 6-chloro-1H-indole (5 g, 32.98 mmol) in AcOH (80 mL) was added NaBH$_3$CN (6.84 g, 108 mmol) at 0° C., and then the mixture was stirred at 25° C. for 12 h under an N$_2$ atmosphere. The reaction mixture was quenched by the addition of ice water (20 mL)

at 0° C. and then saturated aq. NaOH was added to the mixture to adjust the pH to ~8. The mixture was extracted with EtOAc (250 mL×2). The combined organic layers were dried over anhydrous Na₂SO₄, filtered and concentrated under reduced pressure to give a residue. The residue was purified by column chromatography (SiO₂, petroleum ether: ethyl acetate=20:1 to 5:1). The title compound, 6-chloroindoline INDOLINE 2 (3 g, 19.5 mmol, 59.2% yield), was obtained as green oil.

Indonline 4

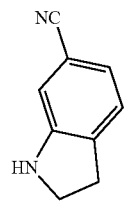

Indoline-6-carbonitrile

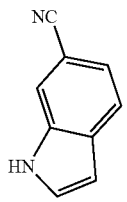 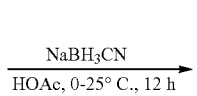 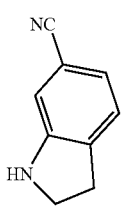

INDOLINE 4: To a mixture of 1H-indole-6-carbonitrile (5 g, 35.1 mmol) in AcOH (80 mL) was added NaBH₃CN (7.29 g, 116.0 mmol) at 0° C., and then the mixture was stirred at 25° C. for 12 h under an N₂ atmosphere. The reaction mixture was quenched by addition of ice water (20 mL) at 0° C. Saturated aq. NaOH was added to the mixture to adjust pH to ~8. The mixture was extracted with EtOAc (300 mL×2). The combined organic layers were dried over anhydrous Na₂SO₄, filtered and concentrated under reduced pressure to give a residue. The residue was purified by column chromatography (SiO₂, petroleum ether:ethyl acetate=10:1 to 5:1). The residue was purified by prep-HPLC (column: Xtimate C18 10μ×250 mm×50 mm; mobile phase:[A, water(10 mM NH₄HCO₃)—B, ACN]; B %: 20%-40%, 25 min). The title compound, indoline-6-carbonitrile INDOLINE 4 (1.9 g, 13.1 mmol, 37.4% yield), was obtained as a white solid.

Indonline 8

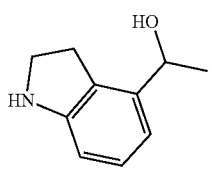

1-(Indolin-4-yl)ethan-1-ol

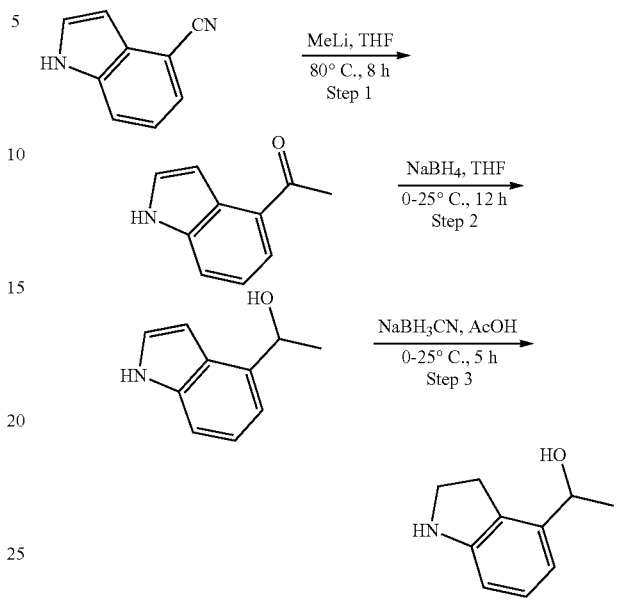

Step 1: To a solution of 1H-indole-4-carbonitrile (5 g, 35.1 mmol) in THF (20 mL) was added MeLi (1.8 M, 41.9 mL). The mixture was stirred at 80° C. for 8 h under an N₂ atmosphere. The reaction mixture was quenched by addition of H₂O (100 mL) at 0° C. The reaction mixture was extracted with DCM (400 mL×2). The combined organic layers were dried over anhydrous Na₂SO₄, filtered and concentrated under reduced pressure to give a residue. The residue was purified by column chromatography (SiO₂, petroleum ether:ethyl acetate=20:1 to 1:1). The title compound, 1-(1H-indol-4-yl) ethanone (2.5 g, 15.7 mmol, 44.6% yield), was obtained as a yellow solid.

Step 2: To a solution of 1-(1H-indol-4-yl)ethanone (2.4 g, 15.0 mmol) in THF (20 mL) was added NaBH₄ (2.28 g, 60.3 mmol) at 0° C. The mixture was stirred at 25° C. for 12 h under N₂ atmosphere. The reaction mixture was quenched by addition of H₂O (100 mL) at 0° C. The reaction mixture was extracted with DCM (250 mL×2). The combined organic layers were dried over anhydrous Na₂SO₄, filtered and concentrated under reduced pressure to give a residue. The residue was purified by column chromatography (SiO₂, petroleum ether:ethyl acetate=1:1). 1-(1H-Indol-4-yl)ethanol (1 g, 6.20 mmol, 41.1% yield) was obtained as a white solid.

INDOLINE 8, Step 3: To a mixture of 1-(1H-indol-4-yl) ethanol (1 g, 6.20 mmol) in AcOH (10 mL) was added NaBH₃CN (1.29 g, 20.4 mmol) at 0° C., and then the mixture was stirred at 25° C. for 5 h under an N₂ atmosphere. The reaction mixture was quenched by addition of ice water (15 mL) at 0° C., and then saturated aq. NaOH was added to the mixture to adjust the pH to ~8. The reaction mixture was extracted with DCM (100 mL×2). The combined organic layers were dried over anhydrous Na₂SO₄, filtered and concentrated under reduced pressure to give a residue. The residue was purified by column chromatography (SiO₂, petroleum ether:ethyl acetate=10:1 to 1:1). 1-Indolin-4-ylethanol INDOLINE 8 (250 mg, 1.53 mmol, 24.6% yield) was obtained as a white solid.

Indoline 10

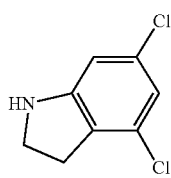 [SMILES: Clc1cc(Cl)c2c(c1)NCC2]

4,6-Dichloroindoline

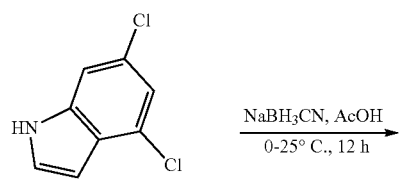

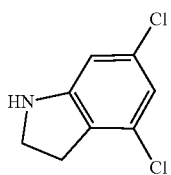

INDOLINE 10: To a mixture of 4,6-dichloro-1H-indole (0.5 g, 2.69 mmol) in AcOH (5 mL) was added NaBH₃CN (557 mg, 8.87 mmol) at 0° C., and then the mixture was stirred at 25° C. for 12 h under an N₂ atmosphere. The reaction mixture was quenched by the addition of ice water (20 mL) at 0° C., and then saturated aq. NaOH was added to the mixture to adjust the pH to ~8. The reaction mixture was extracted with DCM (100 mL×2). The combined organic layers were dried over anhydrous Na₂SO₄, filtered and concentrated under reduced pressure to give a residue. The residue was purified by column chromatography (SiO₂, petroleum ether:ethyl acetate=30:1 to 5:1). 4,6-Dichloroindoline INDOLINE 10 (0.1 g, 531.7 μmol, 19.7% yield) was obtained as yellow oil.

Indonline 13

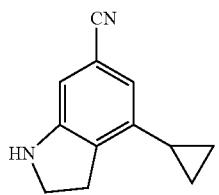

4-Cyclopropylindoline-6-carbonitrile

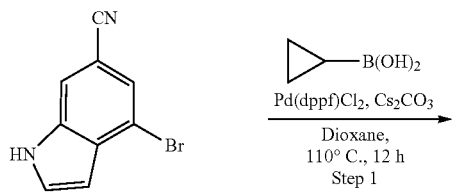

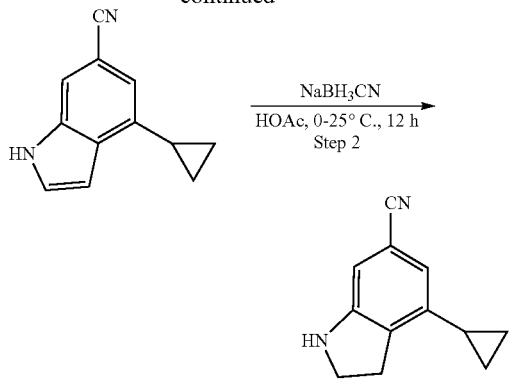

Step 1: A mixture of 4-bromo-1H-indole-6-carbonitrile (0.1 g, 452.3 μmol), cyclopropylboronic acid (77.7 mg, 904.7 μmol), Cs₂CO₃ (294.7 mg, 904.7 μmol), Pd(dppf)Cl₂ (33.1 mg, 45.2 μmol) in dioxane (5 mL) and H₂O (0.5 mL) was degassed and purged with N₂ 3 times. Then the mixture was stirred at 110° C. for 12 h under an N₂ atmosphere. The reaction mixture was diluted with H₂O (20 mL) and extracted with EtOAc (80 mL×2). The combined organic layers were dried over anhydrous Na₂SO₄, filtered and concentrated under reduced pressure to give a residue. The residue was purified by column chromatography (SiO₂, petroleum ether:ethyl acetate=20:1 to 5:1). 4-Cyclopropy 1-1H-indole-6-carbonitrile (50 mg, 274.3 μmol, 60.6% yield) was obtained as a yellow solid.

INDOLINE 13, Step 2: To a solution of 4-cyclopropyl-1H-indole-6-carbonitrile (50 mg, 274.3 μmol) in AcOH (3 mL) was added sodium; cyanoboranuide (56.90 mg, 905.4 μmol) at 0° C. The mixture was stirred at 25° C. for 12 h. The reaction mixture was quenched by the addition of ice water (5 mL) at 0° C., and then saturated aq. NaOH was added to the mixture to adjust pH to ~8. The reaction mixture was extracted with DCM (50 mL×2). The combined organic layers were dried over anhydrous Na₂SO₄, filtered and concentrated under reduced pressure to give a residue. The residue was purified by prep-TLC (SiO₂, petroleum ether: ethyl acetate=5:1). Compound 4-cyclopropylindoline-6-carbonitrile INDOLINE 13 (20 mg, 108.6 μmol, 39.5% yield) was obtained as a yellow solid.

Indonline 16

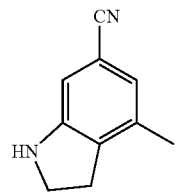

4-Methylindoline-6-carbonitrile

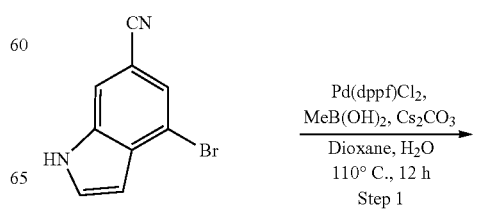

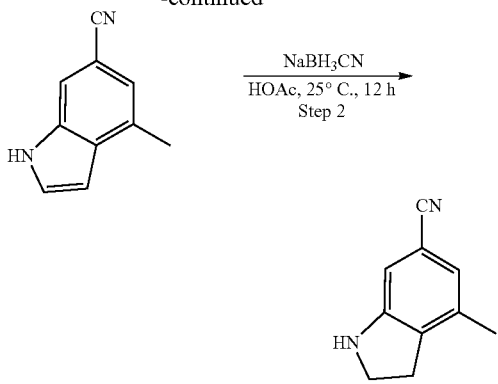

Step 1: To a mixture of 4-bromo-1H-indole-6-carbonitrile (1 g, 4.52 mmol) in dioxane (15 mL) and $H_2O$ (1.5 mL) was added methylboronic acid (541.5 mg, 9.05 mmol), $Cs_2CO_3$ (2.95 g, 9.05 mmol) and $Pd(dppf)Cl_2$ (331.0 mg, 452.3 μmol) in one portion. The mixture was heated to 110° C. and stirred for 12 h. The reaction mixture was diluted with $H_2O$ (300 mL) and extracted with EtOAc (150 mL×2). The combined organic layers were washed with brine (300 mL), dried over $Na_2SO_4$, filtered and concentrated under reduced pressure to give a residue. The residue was purified by column chromatography ($SiO_2$, petroleum ether:ethyl acetate=1:0 to 0:1). 4-Methyl-1H-indole-6-carbonitrile (600 mg, 3.34 mmol, 73.8% yield) was obtained as a light yellow solid.

INDOLINE 16, Step 2: To a solution of 4-methyl-1H-indole-6-carbonitrile (600 mg, 3.84 mmol) in HOAc (15 mL) was added $NaBH_3CN$ (1.45 g, 23.0 mmol). The mixture was stirred at 25° C. for 12 h. The reaction mixture was added saturated aq. $Na_2CO_3$ by pH to ~8.

The mixture was diluted with $H_2O$ (300 mL) and extracted with EtOAc (150 mL×3). The combined organic layers were washed with brine (300 mL), dried over $Na_2SO_4$, filtered and concentrated under reduced pressure to give a residue. The residue was purified by column chromatography ($SiO_2$, petroleum ether:ethyl acetate=1:0 to 0:1). 4-Methylindoline-6-carbonitrile (250 mg, 1.20 mmol, 31.2% yield) was obtained as a light yellow solid.

Indonline 18

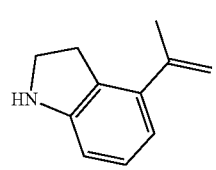

4-(Prop-1-en-2-yl)indoline

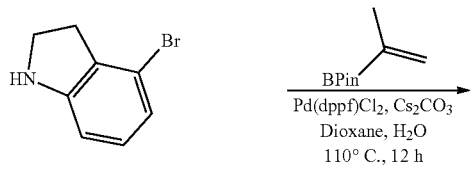

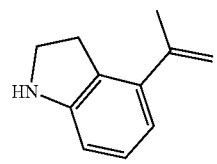

INDOLINE 18: A mixture of 4-bromoindoline (0.5 g, 2.52 mmol), 2-isopropenyl-4,4,5,5-tetramethyl-1,3,2-dioxaborolane (509.0 mg, 3.03 mmol), $Cs_2CO_3$ (1.23 g, 3.79 mmol), $Pd(dppf)Cl_2$ (184.7 mg, 252.4 μmol) in dioxane (10 mL) and $H_2O$ (2 mL) was degassed and purged with $N_2$ 3 times, and then the mixture was stirred at 110° C. for 12 h under an $N_2$ atmosphere. The reaction mixture was diluted with $H_2O$ (20 mL) and extracted with DCM (60 mL×3). The combined organic layers were washed with saturated brine (20 mL), dried over anhydrous $Na_2SO_4$, filtered and concentrated under reduced pressure to give a residue. The residue was purified by column chromatography ($SiO_2$, petroleum ether:ethyl acetate=1:0 to 10:1). 4-Isopropenylindoline (60 mg, 376.8 μmol, 14.9% yield) was obtained as a yellow solid.

Indonline 20

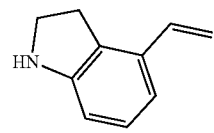

4-Vinylindoline

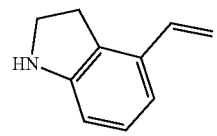

INDOLINE 20: To a mixture of 4-bromoindoline (1 g, 5.05 mmol) and 4,4,5,5-tetramethyl-2-vinyl-1,3,2-dioxaborolane (933 mg, 6.06 mmol) in dioxane (10 mL) and $H_2O$ (2 mL) as added $Pd(dppf)Cl_2$ (369 mg, 504.9 μmol) and $Cs_2CO_3$ (2.47 g, 7.57 mmol) at 15° C. under $N_2$. The mixture was heated to 110° C. and stirred for 12 hours. The residue was diluted with $H_2O$ (120 mL) and extracted with EtOAc (60 mL×2). The combined organic layers were washed with brine 120 mL, dried over $Na_2SO_4$, filtered and concentrated under reduced pressure to give a residue. The residue was purified by column chromatography ($SiO_2$, petroleum ether: ethyl acetate=1:0 to 10:1). 4-Vinylindoline INDOLINE 20 (400 mg, 2.45 mmol, 48.6% yield) was obtained as a yellow oil.

Indonline 22

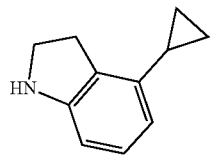 [SMILES: c1cc2c(c(C3CC3)c1)CCN2]

4-Cyclopropylindoline

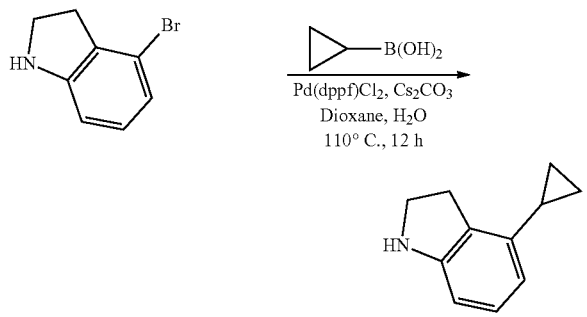

INDOLINE 22: To a solution of 4-bromoindoline (0.5 g, 2.52 mmol) in dioxane (10 mL) and H$_2$O (1 mL) was added cyclopropylboronic acid (433.6 mg, 5.05 mmol), dicesium; carbonate (1.65 g, 5.05 mmol) and cyclopentyl(diphenyl)phosphane;dichloropalladium;iron (184.7 mg, 252.4 µmol). The mixture was stirred at 110° C. for 12 h under an N$_2$ atmosphere. The reaction mixture was diluted with H$_2$O 15 mL and extracted with EtOAc (40 mL×2). The combined organic layers were washed with saturated brine 20 mL, dried over anhydrous Na$_2$SO$_4$, filtered and concentrated under reduced pressure to give a residue. The residue was purified by column chromatography (SiO$_2$, petroleum ether:ethyl acetate=1:0 to 10:1). 4-Cyclopropylindoline INDOLINE 22 (0.1 g, 628 mol, 24.8% yield) was obtained as yellow oil.

Example 51

This Example illustrates that exemplary compounds of the present invention inhibit ROCK1 and/or ROCK2 enzymatic activity.

Dose-response curves for compounds of the present invention were determined using a fluorescence coupling enzymatic assay using purified C-terminal truncated human ROCK1 catalytic domain (amino acids 1-477 of accession number NP_005397.1) fused to GST (Carna BioSciences, Catalog #01-109) and purified C-terminal truncated human ROCK2 enzyme kinase domain (amino acids 1-553 of accession number NP_004841.2) fused to GST (Carna BioSciences, Catalog #01-110). In addition, full length cGMP-dependent protein kinase 1 (PKG or PRKG1; amino acids 1-686 of accession number NP_006249.1) fused to GST (Carna BioSciences, Catalog #01-142), full length PKACa (PRKACA; amino acids 1-351 of accession number NP_002721.1) fused to GST (Carna BioSciences, Catalog #01-127), and C-terminal truncated human AKT1 catalytic domain (amino acids 104-480 of accession number NP_005154.1) fused to GST (Carna Biosciences, Catalog #01-101) were used as a control to measure any non-desired off-target kinase activity.

Briefly, compounds of the present invention were solubilized in DMSO and a series of 12, three-fold serial dilutions were made for each compound in 2.5% DMSO. The initial starting concentration for the serial dilutions of each compound was 10 µM or 100 µM. Control samples lacking compound, ROCK enzyme or ATP also were prepared and processed in parallel with compound test samples.

A 4 µL aliquot of each serial dilution of test compound diluted in H$_2$O with 2.5% DMSO was added to a well containing 4 µL of 10 nM purified N-truncated ROCK1 (4 nM final concentration), 10 nM purified N-truncated ROCK2 enzyme (4 nM final concentration), 1.25 nM AKT1 (0.5 nM final concentration), 25 pM PKACA (10 pM final concentration) or 20 nM PKG (8 nM final concentration), in reaction buffer containing 50 mM Hepes, pH 7.5, 1 mM EGTA, 10 mM MgCl$_2$, 2 mM DTT, and 0.01% Tween 20 (final concentration). To initiate the enzymatic reaction, 2 µL of a solution was added to each well to provide a final concentration of 50 nM Ulight-CREBTide peptide substrate (Perkin Elmer, Catalog # TRF0107) and 4 µM ATP for ROCK1 and AKT1 assays, 8 µM ATP for ROCK2 assays and 30 µM ATP for PKG assays, or 1 µM ATP for PKACA assays. The reaction mixtures were incubated at room temperature for one hour. After one hour, the reaction was stopped by the addition of a 10 µL solution of an Europium-labelled phospho-CREB (Ser133) antibody (Perkin Elmer, Catalog # TRF0200) in LANCE buffer supplemented with 20 mM EDTA. The stopped reaction mixtures were incubated at room temperature for 90 minutes. The TR-FRET 665/620 ratios were determined using a Clariostar monochromator plate reader instrument (BMG LabTech) in accordance with the manufacturer's instructions. The IC$_{50}$ value for each compound was determined from each dose-response curve using GraphPad Prism 7 software with a sigmodial dose response. The results for exemplary compounds of Formula (I) and Formula (II) are shown in Table 1. Key: A is IC$_{50}$≤100 nM; B is 100 nM<IC$_{50}$<1000 nM; C is 1,000<IC$_{50}$≤10,000 nM; D is IC$_{50}$>10,000 nM

TABLE 1

Inhibition of ROCK Activity by Exemplary Compounds of Formula (I)

| Example Number | ROCK1 | ROCK2 | PKACA | AKT1 | PKG |
|---|---|---|---|---|---|
| 1 | C | C | D | D | D |
| 2 | D | D | D | D | D |
| 3 | C | C | D | D | D |
| 4 | B | B | D | D | D |
| 5 | C | C | D | D | D |
| 6 | C | B | D | D | D |
| 7 | C | C | D | D | D |
| 8 | D | D | D | D | D |
| 9 | D | D | D | D | D |
| 10 | D | D | D | D | D |
| 11 | C | C | D | D | D |
| 12 | D | D | D | D | D |
| 13 | D | D | D | D | D |
| 14 | D | D | D | D | D |
| 15 | B | A | D | D | D |
| 16 | C | C | D | D | D |
| 17 | B | B | D | D | D |
| 18 | B | B | D | D | D |
| 19 | D | D | D | D | D |
| 20 | D | D | D | D | D |
| 21 | D | D | D | D | D |

TABLE 1-continued

Inhibition of ROCK Activity by Exemplary Compounds of Formula (I)

| Example Number | ROCK1 | ROCK2 | PKACA | AKT1 | PKG |
|---|---|---|---|---|---|
| 22 | A | A | C | D | D |
| 23 | B | B | D | D | D |
| 24 | C | C | D | D | D |
| 25 | C | C | D | D | D |
| 26 | B | B | D | D | D |
| 27 | A | A | C | C | D |
| 28 | B | B | D | D | D |
| 29 | A | A | C | C | D |
| 30 | A | A | C | C | D |
| 31 | A | A | C | D | D |
| 32 | A | A | D | D | C |
| 33 | A | A | D | D | D |
| 34 | C | C | D | D | D |
| 35 | A | A | D | D | C |
| 36 | A | A | D | D | C |
| 37 | B | B | D | D | D |
| 38 | B | B | D | D | D |
| 39 | B | B | D | D | D |
| 40 | A | A | D | D | D |
| 41 | B | B | D | D | D |
| 42 | B | A | D | D | D |
| 43 | C | B | D | D | D |
| 44 | C | C | D | D | D |
| 45 | A | A | B | A | C |
| 46 | N/A | N/A | N/A | N/A | N/A |
| 47 | N/A | N/A | N/A | N/A | N/A |
| 48 | N/A | N/A | N/A | N/A | N/A |
| 49 | N/A | N/A | N/A | N/A | N/A |
| 50 | N/A | N/A | N/A | N/A | N/A |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound selected from the group consisting of:

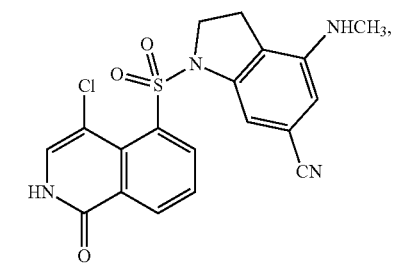

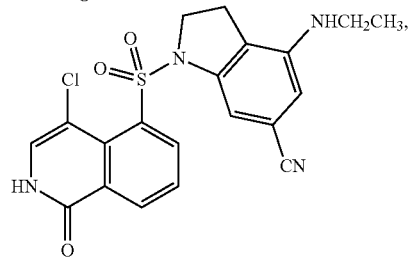

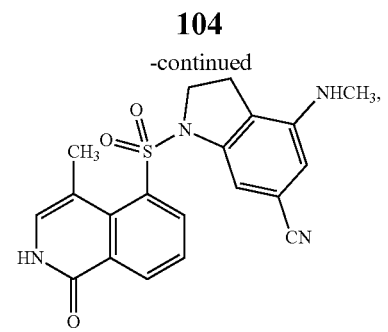

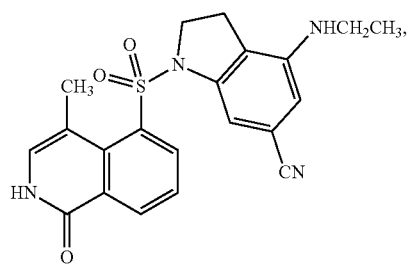

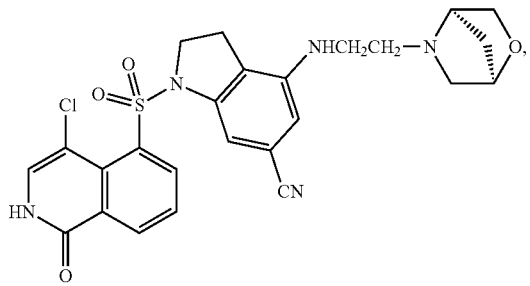

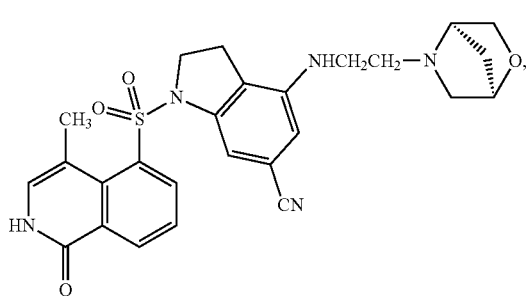

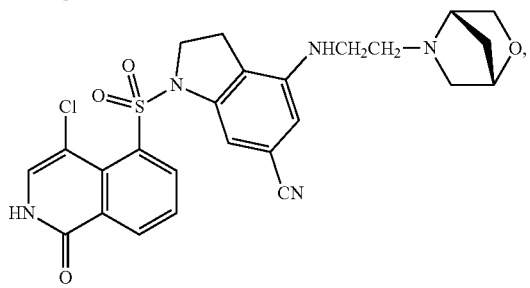

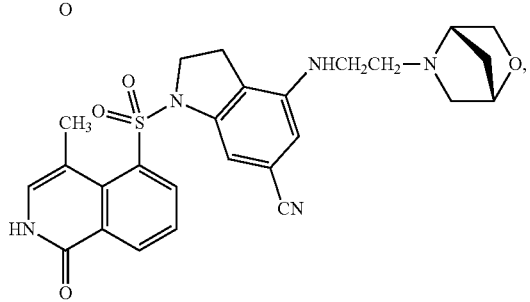

-continued

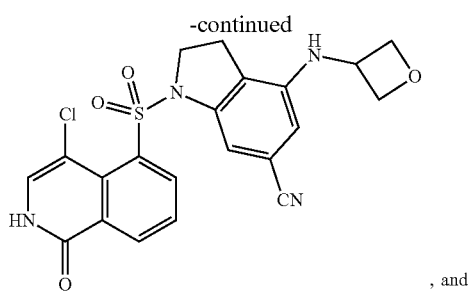

, and

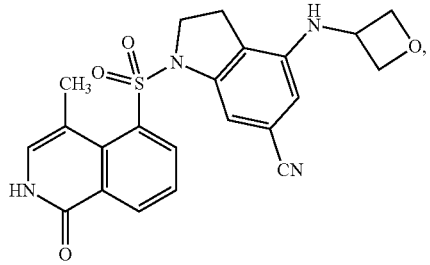

or a pharmaceutically acceptable salt thereof.

2. The compound of claim 1, wherein the compound is:

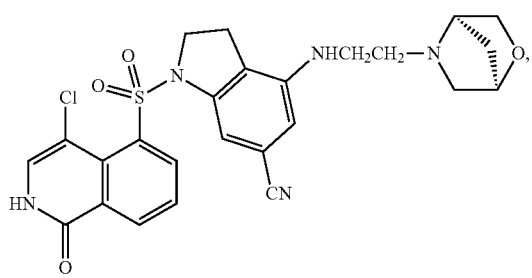

or a pharmaceutically acceptable salt thereof.

3. The compound of claim 1, wherein the compound is:

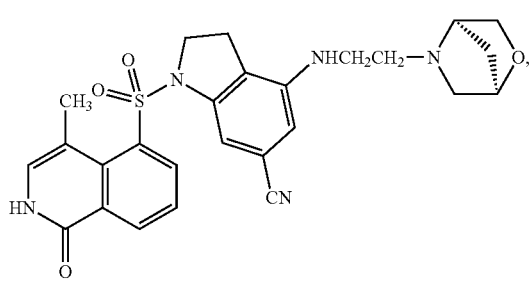

or a pharmaceutically acceptable salt thereof.

4. The compound of claim 1, wherein the compound is:

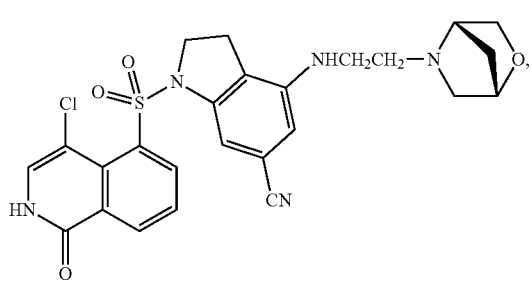

or a pharmaceutically acceptable salt thereof.

5. The compound of claim 1, wherein the compound is:

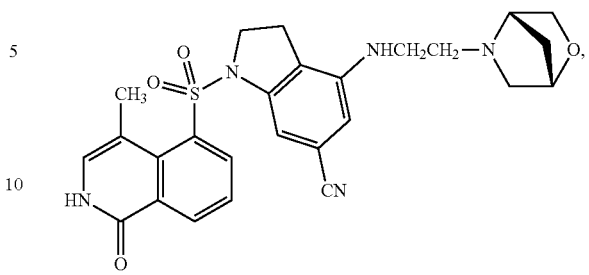

or a pharmaceutically acceptable salt thereof.

6. A pharmaceutical composition comprising a pharmaceutically acceptable excipient and a therapeutically effective amount of a compound of claim 1, or a pharmaceutically acceptable salt thereof.

7. A method for inhibiting rho-associated protein kinase activity in a cell, wherein the method comprises contacting the cell with a therapeutically effective amount of a compound of claim 1, or a pharmaceutically acceptable salt thereof.

8. The method of claim 7, wherein the cell is contacted in vivo.

9. The method of claim 7, wherein the therapeutically effective amount of the compound ranges from 0.01 mg/kg to 300 mg/kg per day.

10. The method of claim 9, wherein the therapeutically effective amount of the compound ranges from 0.1 mg/kg to 100 mg/kg per day.

11. A method for treating cerebral cavernous malformation syndrome in a patient, wherein the method comprises administering to the patient in need thereof a therapeutically effective amount of a compound of claim 1, or a pharmaceutically acceptable salt thereof, or a pharmaceutical composition of claim 6.

12. The method of claim 11, wherein the therapeutically effective amount of the compound ranges from 0.01 mg/kg to 300 mg/kg per day.

13. The method of claim 12, wherein the therapeutically effective amount of the compound ranges from 0.1 mg/kg to 100 mg/kg per day.

14. A method for treating a cardiovascular disease associated with increased vasotension in a patient, wherein the method comprises administering to the patient in need thereof a therapeutically effective amount of a compound of claim 1, or a pharmaceutically acceptable salt thereof, or a pharmaceutical composition of claim 6;
wherein the cardiovascular disease associated with increased vasotension is selected from the group consisting of angina, atherosclerosis, cerebral vasospasm, coronary vasospasm, erectile dysfunction, hypertension, and ischemic stroke.

15. The method of claim 14, wherein the cardiovascular disease associated with increased vasotension is hypertension.

16. A method for treating a disease involving elevated non-vascular smooth muscle contractility in a patient, wherein the method comprises administering to the patient in need thereof a therapeutically effective amount of a compound of claim 1, or a pharmaceutically acceptable salt thereof, or a pharmaceutical composition of claim 6;
wherein the disease involving elevated non-vascular smooth muscle contractility is selected from the group consisting of asthma and glaucoma.

17. The method of claim 16, wherein the disease involving elevated non-vascular smooth muscle contractility is asthma.

\* \* \* \* \*